United States Patent
Mitsudera et al.

(10) Patent No.: US 9,854,803 B2
(45) Date of Patent: Jan. 2, 2018

(54) NOXIOUS ARTHROPOD CONTROL AGENT CONTAINING AMIDE COMPOUND

(71) Applicant: SUMITOMO CHEMICAL COMPANY, LIMITED, Tokyo (JP)

(72) Inventors: Hiromasa Mitsudera, Takarazuka (JP); Ayano Kowata, Takarazuka (JP); Kazuya Ujihara, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/329,561

(22) PCT Filed: Jul. 21, 2015

(86) PCT No.: PCT/JP2015/070651
§ 371 (c)(1),
(2) Date: Jan. 26, 2017

(87) PCT Pub. No.: WO2016/017466
PCT Pub. Date: Feb. 4, 2016

(65) Prior Publication Data
US 2017/0215424 A1 Aug. 3, 2017

(30) Foreign Application Priority Data
Jul. 29, 2014 (JP) .................................. 2014-153625

(51) Int. Cl.
| | | |
|---|---|---|
| A01N 43/80 | (2006.01) | |
| A01N 43/72 | (2006.01) | |
| A01N 43/08 | (2006.01) | |
| A01N 43/16 | (2006.01) | |
| A61K 31/351 | (2006.01) | |
| A61K 31/42 | (2006.01) | |
| A61K 31/5355 | (2006.01) | |
| C07D 407/12 | (2006.01) | |
| C07D 413/12 | (2006.01) | |
| C07D 261/04 | (2006.01) | |

(52) U.S. Cl.
CPC ............ *A01N 43/80* (2013.01); *A01N 43/08* (2013.01); *A01N 43/16* (2013.01); *A01N 43/72* (2013.01); *A61K 31/351* (2013.01); *A61K 31/42* (2013.01); *A61K 31/5355* (2013.01); *C07D 261/04* (2013.01); *C07D 407/12* (2013.01); *C07D 413/12* (2013.01)

(58) Field of Classification Search
CPC ........ A01N 43/80; A01N 43/72; A01N 43/08; A01N 43/16
See application file for complete search history.

(56) References Cited

U.S. PATENT DOCUMENTS

| | | | |
|---|---|---|---|
| 4,876,275 A | 10/1989 | Himmele et al. | |
| 6,645,984 B2 * | 11/2003 | Braun ................ | A01N 43/80 504/100 |
| 2003/0078287 A1 | 4/2003 | Elbe et al. | |
| 2013/0178502 A1 | 7/2013 | Soergel et al. | |
| 2015/0344466 A1 | 12/2015 | Mitsudera et al. | |

FOREIGN PATENT DOCUMENTS

| | | |
|---|---|---|
| CA | 2072229 A1 | 12/1992 |
| EP | 0 520 371 A2 | 12/1992 |
| JP | 63-258871 A | 10/1988 |
| JP | 9-143171 A | 6/1997 |
| JP | 2000-516917 A | 12/2000 |
| JP | 2013-542918 A | 11/2013 |
| WO | WO 2013/003505 A1 | 1/2013 |
| WO | WO 2014/119696 A1 | 8/2014 |

OTHER PUBLICATIONS

Chemical Abstracts Registry No. 91567-55-4, indexed in the Registry file on STN CAS Online on Nov. 16, 1984.*
International Search Report issued in PCT/JP2015/070651 (PCT/ISA/210), dated Oct. 27, 2015.
Written Opinion of the International Searching Authority (Form PCT/ISA/237) for International Application No. PCT/JP2015/070651, dated Oct. 27, 2015.

* cited by examiner

*Primary Examiner* — Laura L. Stockton
(74) *Attorney, Agent, or Firm* — Birch, Stewart, Kolasch & Birch, LLP

(57) ABSTRACT

An object of the present invention is to provide a compound having the controlling activity on a noxious arthropod, and a noxious arthropod controlling agent containing an amide compound of formula (I):

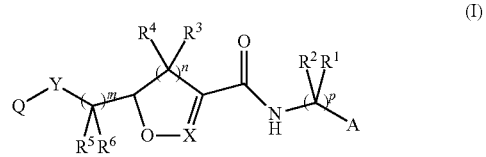

wherein X represents a nitrogen atom or a CH group, p represents 0 or 1, A represents a tetrahydrofuranyl group or the like, $R^1$, $R^2$, $R^3$, $R^4$, $R^5$, $R^6$ and $R^7$ represent a hydrogen atom or the like, n represents 1 or 2,
Y represents an oxygen atom or the like, m represents any integer of 0 to 7, and Q represents a C1-8 chain hydrocarbon group optionally having a phenyl group or the like, has the excellent noxious arthropod controlling effect.

6 Claims, No Drawings

NOXIOUS ARTHROPOD CONTROL AGENT CONTAINING AMIDE COMPOUND

TECHNICAL FIELD

The present invention relates to a noxious arthropod controlling agent containing an amide compound.

BACKGROUND ART

For controlling a noxious arthropod, varied noxious arthropod controlling agents have been developed so far, and have been used. Patent Document 1 describes certain amide compounds.

PRIOR ART DOCUMENT

Patent Document

Patent Document 1: JP-A-9-143171

DISCLOSURE OF THE INVENTION

Problems to be Solved by the Invention

An object of the present invention is to provide a noxious arthropod controlling agent having excellent controlling efficacy.

Means for Solving the Problems

In order to find out a noxious arthropod controlling agent having excellent controlling efficacy, the present inventors have intensively studied, and as the result, found that an amide compound of following formula (I) (hereinafter, referred to as the present amide compound in some cases) has excellent efficacy against noxious arthropod and hence it is useful as an active ingredient of a noxious arthropod controlling agent, and thereby completed the present invention.

That is, the present invention embraces followings:
[1] A noxious arthropod controlling agent containing an amide compound of formula (I):

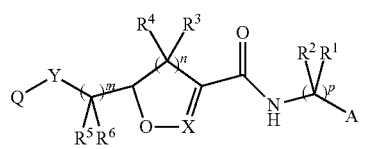

wherein
X represents a nitrogen atom or a CH group,
p represents 0 or 1,
A represents
a phenyl group optionally having one or more atoms or groups selected from Group F,
a C3-C6 cycloalkyl group optionally having one or more atoms or groups selected from Group F,
a pyridyl group optionally having one or more atoms or groups selected from Group F,
a 3 to 7-membered saturated heterocyclic group optionally having one or more atoms or groups selected from Group F, wherein a hetero atom or atoms constituting the heterocycle is one or more atoms selected from the group consisting of an oxygen atom and a sulfur atom, and the hetero atoms are not adjacent to each other, or
a C1-C5 alkyl group optionally having one or more groups selected from the group consisting of a hydroxyl group and a C1-C3 alkoxy group, wherein when A is a C1-C5 alkyl group optionally having one or more groups selected from the group consisting of a hydroxyl group and a C1-C3 alkoxy group, p is 1,
$R^1$ and $R^2$ are the same or different, and independently represent a C1-C3 alkyl group or a hydrogen atom,
$R^3$ and $R^4$ are the same or different, and independently represent a C1-C3 alkyl group optionally having one or more halogen atoms, or
a hydrogen atom,
n represents 1 or 2,
$R^5$ and $R^6$ are the same or different, and independently represent
a C1-C4 alkyl group optionally having one or more halogen atoms, a halogen atom, or a hydrogen atom,
Y represents a single bond, or an oxygen atom,
when Y represents a single bond, m represents 0, and Q represents a C1-C8 chain hydrocarbon group having one or more atoms or groups selected from Group C, or
a C3-C8 chain hydrocarbon group,
when Y represents an oxygen atom, m represents an integer of 0 to 7, and
Q represents a C1-8 chain hydrocarbon group optionally having one or more atoms or groups selected from Group D, or one group selected from Group E,
Group C consisting of
a C3-C8 cycloalkyl group optionally having one or more atoms or groups selected from Group B,
an indanyl group optionally having one or more atoms or groups selected from Group B,
a 1,2,3,4-tetrahydronaphthyl group optionally having one or more atoms or groups selected from Group B,
a phenyl group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B,
a benzothienyl group optionally having one or more atoms or groups selected from Group B,
a 1,3-benzodioxolyl group optionally having one or more atoms or groups selected from Group B,
a 1,4-benzodioxanyl group optionally having one or more atoms or groups selected from Group B,
a halogen atom, a C1-C4 alkoxycarbonyl group optionally having one or more halogen atoms,
a cyano group, a nitro group, a carboxyl group, a hydroxyl group,
and a —$CONR^9R^{10}$ group;
Group D consisting of
a C3-C8 cycloalkyl group optionally having one or more atoms or groups selected from Group B,
an indanyl group optionally having one or more atoms or groups selected from Group B, a 1,2,3,4-tetrahydronaphthyl group optionally having one or more atoms or groups selected from Group B,
a phenyl group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B,
a benzothienyl group optionally having one or more atoms or groups selected from Group B,
a 1,3-benzodioxolyl group optionally having one or more atoms or groups selected from Group B,
a 1,4-benzodioxanyl group optionally having one or more atoms or groups selected from Group B,
a phenoxy group optionally having one or more atoms or groups selected from Group B,
a halogen atom,
a C1-C4 alkoxycarbonyl group optionally having one or more halogen atoms,
a cyano group, a nitro group, a carboxyl group, a hydroxyl group,
and a —CONR$^9$R$^{10}$ group;
Group E consisting of
a C3-C8 cycloalkyl group optionally having one or more atoms or groups selected from Group B,
an indanyl group optionally having one or more atoms or groups selected from Group B,
a 1,2,3,4-tetrahydronaphthyl group optionally having one or more atoms or groups selected from Group B,
a phenyl group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B, and
a benzothienyl group optionally having one or more atoms or groups selected from Group B,
Group B consisting of
a C1-C4 alkyl group optionally having one or more halogen atoms,
a C1-C4 alkyl group having one or more benzyloxy groups,
a C1-C4 alkoxy group optionally having one or more halogen atoms,
a C1-C4 alkylthio group optionally having one or more halogen atoms,
a C1-C4 alkylsulfinyl group optionally having one or more halogen atoms,
a C1-C4 alkylsulfonyl group optionally having one or more halogen atoms,
a C1-C4 alkoxycarbonyl group optionally having one or more halogen atoms,
a vinyl group optionally having one or more atoms or groups selected from Group F,
an ethynyl group optionally having an atom or a group selected from Group F,
a phenyl group, a phenoxy group, a cyano group, a nitro group,
a carboxyl group, a hydroxyl group,
a —CONR$^9$R$^{10}$ group, wherein R$^9$ and R$^{10}$ are the same or different,
and independently represent a C1-C4 alkyl group optionally having one or more halogen atoms, or a hydrogen atom,
a methoxymethyl group, and a halogen atom;
Group F consisting of a C1-C4 alkyl group optionally having one or more halogen atoms,
a C1-C4 alkoxy group optionally having one or more halogen atoms,
and a halogen atom,
and an inert carrier.
[2] The noxious arthropod controlling agent as defined in [1], wherein in the formula (I),
p is 1,
A is
a phenyl group optionally having one or more atoms or groups selected from Group F,
a pyridyl group optionally having one or more atoms or groups selected from Group F,
a tetrahydrofuranyl group optionally having one or more atoms or groups selected from Group F,
a tetrahydropyranyl group optionally having one or more atoms or groups selected from Group F, or
a C1-C5 alkyl group optionally having one or more groups selected from the group consisting of a hydroxyl group and a C1-C3 alkoxy group,
R$^1$ is a hydrogen atom,
R$^2$ is a methyl group or a hydrogen atom,
R$^3$ and R$^4$ are a hydrogen atom,
R$^5$ and R$^6$ are a hydrogen atom, and wherein
when Y is a single bond, m is 0, and
Q is a C1-C8 alkyl group having one or more groups selected from Group G, or a C3-C8 alkyl group, and wherein
when Y is an oxygen atom, m is an integer of 1 to 7, and
Q is a C1-C8 alkyl group having one or more groups selected from Group G, or one group selected from Group G,
Group G consisting of
a phenyl group optionally having one or more atoms or groups selected from Group H, and
a naphthyl group optionally having one or more atoms or groups selected from Group H,
Group H consisting of
a C1-C4 alkyl group, a C1-C4 alkoxy group and a halogen atom.
[3] The noxious arthropod controlling agent as defined in [2], wherein in the formula (I), X is a nitrogen atom, and n is 1.
[4] The noxious arthropod controlling agent as defined in [2], wherein in the formula (I), X is a nitrogen atom, and n is 2.
[5] The noxious arthropod controlling agent as defined in [2], wherein in the formula (I), X is a CH group, and n is 2.
[6] The noxious arthropod controlling agent as defined in [1], wherein in the formula (I),
R$^1$ is a hydrogen atom,
R$^2$ is a methyl group or a hydrogen atom,
R$^3$ and R$^4$ are a hydrogen atom, a group represented by Q-Y—(CR$^5$R$^6$)$_m$ is a Q$^a$-CH$_2$—O—CH$_2$ group, a Q$^a$-CH$_2$—CH$_2$—CH$_2$ group, a Q$^a$-O—CH$_2$ group or a Q$^a$-CH$_2$ group, wherein Q$^a$ is a phenyl group optionally having one or more atoms or groups selected from Group H, or a naphthyl group optionally having one or more atoms or groups selected from Group H, Group H consisting of a C1-C4 alkyl group, a C1-C4 alkoxy group and a halogen atom.

[7] A method for controlling a noxious arthropod comprising applying an effective amount of the amide compound of formula (I) as defined in [1] to a noxious arthropod or a habitat of a noxious arthropod.

[8] Use of the amide compound of formula (I) as defined in any one of the preceeding items [1] to [7].

Effect of the Invention

Due to its excellent controlling efficacy against noxioius arthropod the present controlling agent is useful for controlling a noxious arthropod.

MODE FOR CARRYING OUT THE INVENTION

As for the amide compound disclosed in the present specification, isomers derived from an asymmetric carbon atom, and isomers derived from a double bond exist as the case may be, and such amide compound include those respective isomers and an mixture thereof in an optional ratio.

In the present specification, examples of the "halogen atom" include, for example, a fluorine atom, a chlorine atom, a bromine atom, and an iodine atom.

In the present specification, examples of the 3 to 7-membered saturated heterocyclic group, wherein the hetero atom or atoms constituting the heterocycle is one or more atoms selected from the group consisting of an oxygen atom and a sulfur atom, and the hetero atoms are not adjacent to each other, include an oxolanyl group, an oxetan-2-yl group, an oxetan-3-yl group, a tetrahydrofuran-2-yl group (also referred to as oxolan-2-yl group, a tetrahydrofuran-3-yl group (also referred to as oxolan-3-yl group), a 1,3-dioxolan-2-yl group, a 1,3-dioxolan-4-yl group, a tetrahydropyran-2-yl group (also referred to as oxan-2-yl group), a tetrahydropyran-3-yl group (also referred to as oxan-3-yl group), a tetrahydropyran-4-yl group (also referred to as oxan-4-yl group), a 1,3-dioxan-4-yl group, a 1,3-dioxan-5-yl group, a 1,4-dioxan-2-yl group, an oxepan-2-yl group, an oxepan-3-yl group, an oxepan-4-yl group, a 1,3-dioxepan-4-yl group, a 1,3-dioxepan-5-yl group, a 1,4-dioxepan-2-yl group, a 1,4-dioxepan-5-yl group, a 1,4-dioxepan-6-yl group, a thiolanyl group, a thioxetan-2-yl group, a thiolan-2-yl group, a thiolan-3-yl group, a 1-oxo-3-thiolan-2-yl group, a 1-oxo-3-thiolan-4-yl group, a thian-2-yl group, a thian-3-yl group, a thian-4-yl group, a 1,4-oxathian-2-yl group and the like.

In the present specification, examples of the C1-C5 alkyl group optionally having one or more groups selected from the group consisting of a hydroxy group and a C1-C3 alkoxy group include, for example, a 1-methylethyl group, a 1-methoxymethyl group, a 1-methoxyethyl group, a 1-methoxy-1-methylethyl group, a 1,1-dimethoxymethyl group, a 2-methoxy-1,1-dimethylethyl group, a 2-methoxy-1-(methoxymethyl)ethyl group, a 1-hydroxyethyl group, a 2-hydroxy-1,1-dimethylethyl group and the like.

In the present invention, examples of the tetrahydrofuranyl group optionally having one or more atoms or groups selected from Group F include, for example, a 3-tetrahydrofuranyl group.

Examples of the tetrahydropyranyl group optionally having one or more atoms or groups selected from Group F include, for example, a 3-tetrahydropyranyl group, and a 4-tetrahydropyranyl group.

Examples of the C1-C3 hydrocarbon group optionally having one or more halogen atoms include, for example, a methyl group, an ethyl group, a propyl group, an isopropyl group, an iodomethyl group, a bromomethyl group, a chloromethyl group, a fluoromethyl group, a difluoromethyl group, a chlorodifluoromethyl group, a trichloromethyl group, a trifluoromethyl group, a 1-fluoroethyl group, a 2-fluoroethyl group, a 1-fluoropropyl group, a 2-fluoropropyl group, a 3-fluoropropyl group, a 1-fluoro-1-methylethyl group, a 1-chloroethyl group, a 1-chloropropyl group, a 1-chloro-1-methylethyl group, a 1-bromoethyl group, a 1-bromopropyl group, a 1-bromo-1-methylethyl group, a 2,2,2-trifluoroethyl group, a 1,1,2,2-tetrafluoroethyl group and a 1,1,2,2,2-pentafluoroethyl group.

Examples of the C1-8 chain hydrocarbon group having one or more atoms or groups selected from Group C and the C1-C8 chain hydrocarbon group optionally having one or more atoms or groups selected from Group D include, for example:

a benzyl group, a phenyldifluoromethyl group, a 1-phenylethyl group, a 1,1-difluoro-1-phenylethyl group, a 2,2,2-trifluoro-1-phenylethyl group, a 1,2,2,2-tetrafluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 7-phenylheptyl group, a 1,1-difluoro-7-phenylheptyl group, a 8-phenyloctyl group, a 1,1-difluoro-8-phenyloctyl group, a 4-cyanobenzyl group, a 4-nitrobenzyl group, a 4-carboxylbenzyl group, a 4-hydroxylbenzyl group, a 4-(N-methylcarbamido)benzyl group, a 4-(N,N-dimethylcarbamido)benzyl group, a 4-methylbenzyl group, a 4-trifluoromethylbenzyl group,
a 4-methoxybenzyl group, a 4-trifluoromethoxybenzyl group,
a 4-methylthiobenzyl group, a 4-methylsulfinylbenzyl group,
a 4-methylsulfonylbenzyl group, a 4-methoxycarbonylbenzyl group, a 4-vinylbenzyl group, a 4-(2',2'-difluorovinyl)benzyl group, a 4-ethynylbenzyl group, 4-(2'-fluoroethynyl)benzyl group, a 4-fluorobenzyl group, a 4-chlorobenzyl group,
a 3,4-dichlorobenzyl group, a (4'-cyanophenyl)difluoromethyl group,
a (1-naphthyl)methyl group,
a (1-naphthyl)difluoromethyl group,
a 1-(1-naphthyl)ethyl group,
a 2,2,2-trifluoro-1-(1-naphthyl)ethyl group,
a 1,2,2,2-tetrafluoro-1-(1-naphthyl)ethyl group,
a 2-(1-naphthyl)ethyl group,
a 1,1-difluoro-2-(1-naphthyl)ethyl group,
a 2,2-difluoro-2-(1-naphthyl)ethyl group,
a 1,1,2,2-tetrafluoro-2-(1-naphthyl)ethyl group,
a 3-(1-naphthyl)propyl group,
a 1,1-difluoro-3-(1-naphthyl)propyl group,
a 2,2-difluoro-3-(1-naphthyl)propyl group,
a 3,3-difluoro-3-(1-naphthyl)propyl group,
a 1,1,2,2,3,3-hexafluoro-3-(1-naphthyl)propyl group,
a 4-(1-naphthyl)butyl group,
a 1,1-difluoro-4-(1-naphthyl)butyl group,
a 2,2-difluoro-4-(1-naphthyl)butyl group,
a 3,3-difluoro-4-(1-naphthyl)butyl group,
a 4,4-difluoro-4-(1-naphthyl)butyl group,
a 1,1,2,2,3,3,4,4-octafluoro-3-4-(1-naphthyl)butyl group,
a 5-(1-naphthyl)pentyl group,
a 1,1-difluoro-5-(1-naphthyl)pentyl group,
a 2,2-difluoro-5-(1-naphthyl)pentyl group,
a 3,3-difluoro-5-(1-naphthyl)pentyl group,
a 4,4-difluoro-5-(1-naphthyl)pentyl group,
a 5,5-difluoro-5-(1-naphthyl)pentyl group,
a 6-(1-naphthyl)hexyl group,
a 1,1-difluoro-6-(1-naphthyl)hexyl group,
a 7-(1-naphthyl)heptyl group,
a 1,1-difluoro-7-(1-naphthyl)heptyl group,
a 8-(1-naphthyl)octyl group,
a 1,1-difluoro-8-(1-naphthyl)octyl group,
a (6-cyano-1-naphthyl)methyl group,
a (6-nitro-1-naphthyl)methyl group,
a (6-carboxyl-1-naphthyl)methyl group,
a (6-hydroxyl-1-naphthyl)methyl group,
a [6-(N-methylcarbamido)-1-naphthyl]methyl group,
a [6-(N,N-dimethylcarbamido)-1-naphthyl]methyl group,
a (6-methyl-1-naphthyl)methyl group,
a (6-trifluoromethyl-1-naphthyl)methyl group,
a (6-methoxy-1-naphthyl)methyl group,
a (6-trifluoromethoxy-1-naphthyl)methyl group,
a (6-methylthio-1-naphthyl)methyl group,
a (6-methylsulfinyl-1-naphthyl)methyl group,
a (6-methylsulfonyl-1-naphthyl)methyl group,
a (6-methoxycarbonyl-1-naphthyl)methyl group,
a (6-vinyl-1-naphthyl)methyl group,
a [6-(2,2-difluorovinyl)-1-naphthyl]methyl group,
a (6-ethynyl-1-naphthyl)methyl group,
a [6-(2-fluoroethynyl)-1-naphthyl]methyl group,
a (6-fluoro-1-naphthyl)methyl group,
a (6-chloro-1-naphthyl)methyl group,
a (6-cyano-1-naphthyl)-difluoromethyl group,
a (2-naphthyl)methyl group,
a (2-naphthyl)difluoromethyl group,
a 1-(2-naphthyl)ethyl group,
a 2,2,2-trifluoro-1-(2-naphthyl)ethyl group,
1,2,2,2-tetrafluoro-1-(2-naphthyl)ethyl group,
a 2-(2-naphthyl)ethyl group,
a 1,1-difluoro-2-(2-naphthyl)ethyl group,
a 2,2-difluoro-2-(2-naphthyl)ethyl group,
a 1,1,2,2-tetrafluoro-2-(2-naphthyl)ethyl group,
a 3-(2-naphthyl)propyl group,
a 1,1-difluoro-3-(2-naphthyl)propyl group,
a 2,2-difluoro-3-(2-naphthyl)propyl group,
a 3,3-difluoro-3-(2-naphthyl)propyl group,
a 1,1,2,2,3,3-hexafluoro-3-(2-naphthyl)propyl group,
a 4-(2-naphthyl)butyl group,
a 1,1-difluoro-4-(2-naphthyl)butyl group,
a 2,2-difluoro-4-(2-naphthyl)butyl group,
a 3,3-difluoro-4-(2-naphthyl)butyl group,
a 4,4-difluoro-4-(2-naphthyl)butyl group,
a 1,1,2,2,3,3,4,4-octafluoro-3-4-(2-naphthyl)butyl group,
a 5-(2-naphthyl)pentyl group,
a 1,1-difluoro-5-(2-naphthyl)pentyl group,
a 2,2-difluoro-5-(2-naphthyl)pentyl group,
a 3,3-difluoro-5-(2-naphthyl)pentyl group,
a 4,4-difluoro-5-(2-naphthyl)pentyl group,
a 5,5-difluoro-5-(2-naphthyl)pentyl group,
a 6-(2-naphthyl)hexyl group,
a 1,1-difluoro-6-(2-naphthyl)hexyl group,
a 7-(2-naphthyl)heptyl group,
a 1,1-difluoro-7-(2-naphthyl)heptyl group,
a 8-(2-naphthyl)octyl group,
a 1,1-difluoro-8-(2-naphthyl)octyl group,
a (6-cyano-2-naphthyl)methyl group,
a (6-nitro-2-naphthyl)methyl group,
a (6-carboxyl-2-naphthyl)methyl group,
a (6-hydroxyl-2-naphthyl)methyl group,
a [6-(N-methylcarbamido)-2-naphthyl]methyl group,
a [6-(N,N-dimethylcarbamido)-2-naphthyl]methyl group,
a (6-methyl-2-naphthyl)methyl group,
a (6-trifluoromethyl-2-naphthyl)methyl group,
a (6-methoxy-2-naphthyl)methyl group,
a (6-trifluoromethoxy-2-naphthyl)methyl group,
a (6-methylthio-2-naphthyl)methyl group,
a (6-methylsulfinyl-2-naphthyl)methyl group,
a (6-methylsulfonyl-2-naphthyl)methyl group,
a (6-methoxycarbonyl-2-naphthyl)methyl group,
a (6-vinyl-2-naphthyl)methyl group,
a [6-(2,2-difluorovinyl)-2-naphthyl]methyl group,
a (6-ethynyl-2-naphthyl)methyl group,
a [6-(2-fluoroethynyl)-2-naphthyl]methyl group,
a (6-fluoro-2-naphthyl)methyl group,
a (6-chloro-2-naphthyl)methyl group,
a (6-cyano-1-naphthyl)-difluoromethyl group,
a (2-pyridyl)methyl group, a 1-(2-pyridyl)ethyl group,
a 2-(2-pyridyl)ethyl group, a 3-(2-pyridyl)propyl group,
a 4-(2-pyridyl)butyl group, a 5-(2-pyridyl)pentyl group,
a 6-(2-pyridyl)hexyl group, a 7-(2-pyridyl)heptyl group,
a 8-(2-pyridyl)octyl group,
a (4-cyano-2-pyridyl)methyl group,
a (4-nitro-2-pyridyl)methyl group,
a (4-carboxyl-2-pyridyl)methyl group,
a (4-hydroxyl-2-pyridyl)methyl group,
a [4-(N-methylcarbamido)-2-pyridyl]methyl group,
a [4-(N,N-dimethylcarbamido)-2-pyridyl]methyl group,
a (4-methyl-2-pyridyl)methyl group,
a (4-trifluoromethyl-2-pyridyl)methyl group,
a (4-methoxy-2-pyridyl)methyl group,
a (4-trifluoromethoxy-2-pyridyl)methyl group,
a (4-methylthio-2-pyridyl)methyl group, a (4-methylsulfinyl-2-pyridyl)methyl group,
a (4-methylsulfonyl-2-pyridyl)methyl group,
a (4-methoxycarbonyl-2-pyridyl)methyl group,
a (4-vinyl-2-pyridyl)methyl group,
a [4-(2,2-difluorovinyl)-2-pyridyl]methyl group,
a (4-ethylnyl-2-pyridyl)methyl group,
a [4-(2-fluoroethylnyl)-2-pyridyl]methyl group,
a (4-fluoro-2-pyridyl)methyl group,
a (4-chloro-2-pyridyl)methyl group,
a (5-cyano-2-pyridyl)methyl group,
a (6-cyano-2-pyridyl)methyl group,
a (3-pyridyl)methyl group, a (5-cyano-3-pyridyl)methyl group,
a (5-nitro-3-pyridyl)methyl group,
a (5-carboxyl-3-pyridyl)methyl group,
a (5-hydroxyl-3-pyridyl)methyl group,
a [5-(N-methylcarbamido)-3-pyridyl]methyl group,
a [5-(N,N-dimethylcarbamido)-3-pyridyl]methyl group,
a (5-methyl-3-pyridyl)methyl group,
a (5-trifluoromethyl-3-pyridyl)methyl group,
a (5-methoxy-3-pyridyl)methyl group,
a (5-trifluoromethoxy-3-pyridyl)methyl group,
a (5-methylthio-3-pyridyl)methyl group,
a (5-methylsulfinyl-3-pyridyl)methyl group,
a (5-methylsulfonyl-3-pyridyl)methyl group,
a (5-methoxycarbonyl-3-pyridyl)methyl group,
a (5-vinyl-3-pyridyl)methyl group,
a [5-(2,2-difluorovinyl)-3-pyridyl]methyl group,
a 5-ethylnyl-3-pyridyl)methyl group,
a [5-(2-fluoroethynyl)-3-pyridyl]methyl group,
a (5-fluoro-3-pyridyl)methyl group,
a (5-chloro-3-pyridyl)methyl group,
(6-cyano-3-pyridyl)methyl group,
a (4-pyridyl)methyl group, a (2-cyano-4-pyridyl)methyl group,
a (2-nitro-4-pyridyl)methyl group,
a (2-carboxyl-4-pyridyl)methyl group,
a (2-hydroxyl-4-pyridyl)methyl group,
a [2-(N-methylcarbamido)-4-pyridyl]methyl group,
a [2-(N,N-dimethylcarbamido)-4-pyridyl]methyl group,
a (2-methyl-4-pyridyl)methyl group,
a (2-trifluoromethyl-4-pyridyl)methyl group,
a (2-methoxy-4-pyridyl)methyl group,
a (2-trifluoromethoxy-4-pyridyl)methyl group,
a (2-methylthio-4-pyridyl)methyl group,
a (2-methylsulfinyl-4-pyridyl)methyl group,
a (2-methylsulfonyl-4-pyridyl)methyl group,
a (2-methoxycarbonyl-4-pyridyl)methyl group,
a (2-vinyl-4-pyridyl)methyl group,
a [2-(2,2-difluorovinyl)-4-pyridyl]methyl group,
a (2-ethynyl-4-pyridyl)methyl group,
a [2-(2-fluoroethynyl)-4-pyridyl]methyl group,
a (2-fluoro-4-pyridyl)methyl group,
a (2-chloro-4-pyridyl)methyl group,
a (6-cyano-4-pyridyl)methyl group,
a (2-quinolyl)methyl group,
a (6-cyano-2-quinolyl)methyl group,
a (6-nitro-2-quinolyl)methyl group,
a (6-carboxyl-2-quinolyl)methyl group,
a (6-hydroxyl-2-quinolyl)methyl group,
a [6-(N-methyl carbamido)-2-quinolyl]methyl group,
a [6-(N,N-dimethylcarbamido)-2-quinolyl]methyl group,
a (6-methyl-2-quinolyl)methyl group,
a (6-trifluoromethyl-2-quinolyl)methyl group,
a (6-methoxy-2-quinolyl)methyl group,
a (6-trifluoromethoxy-2-quinolyl)methyl group,
a (6-methylthio-2-quinolyl)methyl group,
a (6-methylsulfinyl-2-quinolyl)methyl group,
a (6-methylsulfonyl-2-quinolyl)methyl group,
a (6-methoxycarbonyl-2-quinolyl)methyl group,
a (6-vinyl-2-quinolyl)methyl group,
a [6-(2,2-difluorovinyl)-2-quinolyl]methyl group,
a (6-ethynyl-2-quinolyl)methyl group,
a [6-(2-fluoroethynyl)-2-quinolyl]methyl group,
a (6-fluoro-2-quinolyl)methyl group,
a (6-chloro-2-quinolyl)methyl group,
a (6-cyano-3-quinolyl)methyl group,
a (6-cyano-4-quinolyl)methyl group,
a (3-quinolyl)methyl group, a (4-quinolyl)methyl group,
a (2-furyl)methyl group, a (4-cyano-2-furyl)methyl group,
a (4-nitro-2-furyl)methyl group,
a (4-carboxyl-2-furyl)methyl group,
a (4-hydroxyl-2-furyl)methyl group,
a [4-(N-methylcarbamido)-2-furyl]methyl group,
a [4-(N,N-dimethylcarbamido)-2-furyl]methyl group,
a (4-methyl-2-furyl)methyl group,
a (4-trifluoromethyl-2-furyl)methyl group,
a (4-methoxy-2-furyl)methyl group,
a (4-trifluoromethoxy-2-furyl)methyl group,
a (4-methylthio-2-furyl)methyl group,
a (4-methylsulfinyl-2-furyl)methyl group,
a (4-methylsulfonyl-2-furyl)methyl group,
a (4-methoxycarbonyl-2-furyl)methyl group,
a (4-vinyl-2-furyl)methyl group,
a [4-(2,2-difluorovinyl)-2-furyl]methyl group,
a (4-ethynyl-2-furyl)methyl group,
a [4-(2-fluoroethynyl)-2-furyl]methyl group,
a (4-fluoro-2-furyl)methyl group,
a (4-chloro-2-furyl)methyl group,
a (3-furyl)methyl group, a (4-cyano-3-furyl)methyl group,
a (4-nitro-3-furyl)methyl group,
a (4-carboxyl-3-furyl)methyl group,
a (4-hydroxyl-3-furyl)methyl group,
a [4-(N-methylcarbamido)-3-furyl]methyl group,
a [4-(N,N-dimethylcarbamido)-3-furyl]methyl group,
a (4-methyl-3-furyl)methyl group,
a (4-trifluoromethyl-3-furyl)methyl group,
a (4-methoxy-3-furyl)methyl group,
a (4-trifluoromethoxy-3-furyl)methyl group,
a (4-methylthio-3-furyl)methyl group,
a (4-methylsulfinyl-3-furyl)methyl group,
a (4-methylsulfonyl-3-furyl)methyl group,
a (4-methoxycarbonyl-3-furyl)methyl group,
a (4-vinyl-3-furyl)methyl group,
a [4-(2,2-difluorovinyl)-3-furyl]methyl group,
a (4-ethynyl-3-furyl)methyl group,
a [4-(2-fluoroethynyl)-3-furyl]methyl group,
a (4-fluoro-3-furyl)methyl group,
a (4-chloro-3-furyl)methyl group,
a (2-thienyl)methyl group, a (4-cyano-2-thienyl)methyl group,
a (4-nitro-2-thienyl)methyl group,
a (4-carboxyl-2-thienyl)methyl group,
a (4-hydroxyl-2-thienyl)methyl group,
a [4-(N-methylcarbamido)-2-thienyl]methyl group,
a [4-(N,N-dimethylcarbamido)-2-thienyl]methyl group,
a (4-methyl-2-thienyl)methyl group,
a (4-trifluoromethyl-2-thienyl)methyl group,
a (4-methoxy-2-thienyl)methyl group,
a (4-trifluoromethoxy-2-thienyl)methyl group,
a (4-methylthio-2-thienyl)methyl group,
a (4-methylsulfinyl-2-thienyl)methyl group,
a (4-methylsulfonyl-2-thienyl)methyl group,
a (4-methoxycarbonyl-2-thienyl)methyl group, a (4-vinyl-2-thienyl)methyl group,
a [4-(2,2-difluorovinyl)-2-thienyl]methyl group,
a (4-ethynyl-2-thienyl)methyl group,
a [4-(2-fluoroethynyl)-2-thienyl]methyl group,
a (4-fluoro-2-thienyl)methyl group,
a (4-chloro-2-thienyl)methyl group,
a (3-thienyl)methyl group, a (4-cyano-3-thienyl)methyl group,
a (4-nitro-3-thienyl)methyl group,
a (4-carboxyl-3-thienyl)methyl group,
a (4-hydroxyl-3-thienyl)methyl group,
a [4-(N-methylcarbamido)-3-thienyl]methyl group,
a [4-(N,N-dimethylcarbamido)-3-thienyl]methyl group,
a (4-methyl-3-thienyl)methyl group,
a (4-trifluoromethyl-3-thienyl)methyl group,
a (4-methoxy-3-thienyl)methyl group,
a (4-trifluoromethoxy-3-thienyl)methyl group,
a (4-methylthio-3-thienyl)methyl group,
a (4-methylsulfinyl-3-thienyl)methyl group,
a (4-methylsulfonyl-3-thienyl)methyl group,
a (4-methoxycarbonyl-3-thienyl)methyl group,
a (4-vinyl-3-thienyl)methyl group,
a [4-(2,2-difluorovinyl)-3-thienyl]methyl group,
a (4-ethynyl-3-thienyl)methyl group,
a [4-(2-fluoroethynyl)-3-thienyl]methyl group,
a (4-fluoro-3-thienyl)methyl group,
a (4-chloro-3-thienyl)methyl group,
a (2-benzofuranyl)methyl group,
a (5-cyano-2-benzofuranyl)methyl group,
a (5-nitro-2-benzofuranyl)methyl group,
a (5-carboxyl-2-benzofuranyl)methyl group,
a (5-hydroxyl-2-benzofuranyl)methyl group,
a [5-(N-methylcarbamido)-2-benzofuranyl]methyl group,
a [5-(N,N-dimethylcarbamido)-2-benzofuranyl]methyl group,
a (5-methyl-2-benzofuranyl)methyl group,
a (5-trifluoromethyl-2-benzofuranyl)methyl group,
a (5-methoxy-2-benzofuranyl)methyl group,
a (5-trifluoromethoxy-2-benzofuranyl)methyl group,
a (5-methylthio-2-benzofuranyl)methyl group,
a (5-methylsulfinyl-2-benzofuranyl)methyl group,
a (5-methylsulfonyl-2-benzofuranyl)methyl group,
a (5-methoxycarbonyl-2-benzofuranyl)methyl group,
a (5-vinyl-2-benzofuranyl)methyl group,
a [5-(2,2-difluorovinyl)-2-benzofuranyl]methyl group,
a (5-ethynyl-2-benzofuranyl)methyl group,
a [5-(2-fluoroethynyl)-2-benzofuranyl]methyl group,
a (5-fluoro-2-benzofuranyl)methyl group,
a (5-chloro-2-benzofuranyl)methyl group,
a (5-benzofuranyl)methyl group,
a (3-cyano-5-benzofuranyl)methyl group,
a (3-nitro-5-benzofuranyl)methyl group,
a (3-carboxyl-5-benzofuranyl)methyl group,
a (3-hydroxyl-5-benzofuranyl)methyl group,
a [3-(N-methylcarbamido)-5-benzofuranyl]methyl group,
a [3-(N,N-dimethylcarbamido)-5-benzofuranyl]methyl group,
a (3-methyl-5-benzofuranyl)methyl group,
a (3-trifluoromethyl-5-benzofuranyl)methyl group,
a (3-methoxy-5-benzofuranyl)methyl group,
a (3-trifluoromethoxy-5-benzofuranyl)methyl group,
a (3-methylthio-5-benzofuranyl)methyl group,
a (3-methylsulfinyl-5-benzofuranyl)methyl group,
a (3-methylsulfonyl-5-benzofuranyl)methyl group,
a (3-methoxycarbonyl-5-benzofuranyl)methyl group,
a (3-vinyl-5-benzofuranyl)methyl group,
a [3-(2,2-difluorovinyl)-5-benzofuranyl]methyl group,
a (3-ethynyl-5-benzofuranyl)methyl group,
a [3-(2-fluoroethynyl)-5-benzofuranyl]methyl group,
a (3-fluoro-5-benzofuranyl)methyl group,
a (3-chloro-5-benzofuranyl)methyl group,
a (2-benzothienyl)methyl group,
a (5-cyano-2-benzothienyl)methyl group,
a (5-nitro-2-benzothienyl)methyl group,
a (5-carboxyl-2-benzothienyl)methyl group,
a (5-hydroxyl-2-benzothienyl)methyl group,
a [5-(N-methylcarbamido)-2-benzothienyl]methyl group,
a [5-(N,N-dimethylcarbamido)-2-benzothienyl]methyl group,
a (5-methyl-2-benzothienyl)methyl group,
a (5-trifluoromethyl-2-benzothienyl)methyl group,
a (5-methoxy-2-benzothienyl)methyl group,
a (5-trifluoromethoxy-2-benzothienyl)methyl group,
a (5-methylthio-2-benzothienyl)methyl group,
a (5-methylsulfinyl-2-benzothienyl)methyl group,
a (5-methylsulfonyl-2-benzothienyl)methyl group,
a (5-methoxycarbonyl-2-benzothienyl)methyl group,
a (5-vinyl-2-benzothienyl)methyl group,
a [5-(2,2-difluorovinyl)-2-benzothienyl]methyl group,
a (5-ethynyl-2-benzothienyl)methyl group,
a [5-(2-fluoroethynyl)-2-benzothienyl]methyl group,
a (5-fluoro-2-benzothienyl)methyl group,
a (5-chloro-2-benzothienyl)methyl group,
a (5-benzothienyl)methyl group,
a (3-cyano-5-benzothienyl)methyl group,
a (3-nitro-5-benzothienyl)methyl group,
a (3-carboxyl-5-benzothienyl)methyl group,
a (3-hydroxyl-5-benzothienyl)methyl group,
a [3-(N-methylcarbamido)-5-benzothienyl]methyl group,
a [3-(N,N-dimethylcarbamido)-5-benzothienyl]methyl group,
a (3-methyl-5-benzothienyl)methyl group,
a (3-trifluoromethyl-5-benzothienyl)methyl group,
a (3-methoxy-5-benzothienyl)methyl group,
a (3-trifluoromethoxy-5-benzothienyl)methyl group,
a (3-methylthio-5-benzothienyl)methyl group,
a (3-methylsulfinyl-5-benzothienyl)methyl group,
a (3-methylsulfonyl-5-benzothienyl)methyl group,
a (3-methoxycarbonyl-5-benzothienyl)methyl group,
a (3-vinyl-5-benzothienyl)methyl group,
a [3-(2,2-difluorovinyl)-5-benzothienyl]methyl group,
a (3-ethynyl-5-benzothienyl)methyl group,
a [3-(2-fluoroethynyl)-5-benzothienyl]methyl group,
a (3-fluoro-5-benzothienyl)methyl group,
a (3-chloro-5-benzothienyl)methyl group,
a fluoromethyl group, a 1-fluoroethyl group,
a 1,1-difluoroethyl group, a 2-fluoroethyl group,
a 2,2-difluoroethyl group, a 2,2,2-trifluoroethyl group,
a 3-fluoropropyl group, a 3,3,3-trifluoropropyl group,
a 4-fluorobutyl group, a 4,4,4-trifluorobutyl group,
a 3,3,4,4,4-pentafluorobutyl group, a 5-fluoropentyl group,
a 6-fluorohexyl group, a 7-fluoroheptyl group,
a 8-fluorooctyl group,
a chloromethyl group, a bromomethyl group,
a (methoxycarbonyl)methyl group, a cyanomethyl group,
a nitromethyl group, a (carboxy)methyl group,
a hydroxymethyl group and the like.

Examples of the one group selected from Group E include, for example:
a phenyl group, a 4-cyanophenyl group, a 4-nitrophenyl group,
a 4-carboxylphenyl group, a 4-hydroxylphenyl group,
a 4-(N-methylcarbamido)phenyl group,
a 4-(N,N-dimethylcarbamido)phenyl group, a 4-methylphenyl group, a 4-trifluoromethylphenyl group, a 4-methoxyphenyl group, a 4-trifluoromethoxyphenyl group,
a 4-methylthiophenyl group, a 4-methylsulfinylphenyl group,
a 4-methylsulfonylphenyl group,
a 4-methoxycarbonylphenyl group, a 4-vinylphenyl group, a 4-(2,2-difluorovinyl)phenyl group, a 4-ethynylphenyl group,
a 4-(2-fluoroethynyl)phenyl group, a 4-fluorophenyl group, a 4-chlorophenyl group, a 3,4-dichlorophenyl group,
a 1-naphthyl group, a 6-cyano-1-naphthyl group,
a 6-nitro-1-naphthyl group, a 6-carboxyl-1-naphthyl group,
a 6-hydroxyl-1-naphthyl group,
a 6-(N-methylcarbamido)-1-naphthyl group,
a 6-(N,N-dimethylcarbamido)-1-naphthyl group,
a 6-methyl-1-naphthyl group,
a 6-trifluoromethyl-1-naphthyl group,
a 6-methoxy-1-naphthyl group,
a 6-trifluoromethoxy-1-naphthyl group,
a 6-methylthio-1-naphthyl group,
a 6-methylsulfinyl-1-naphthyl group,
a 6-methylsulfonyl-1-naphthyl group,
a 6-methoxycarbonyl-1-naphthyl group,
a 6-vinyl-1-naphthyl group,
a 6-(2,2-difluorovinyl)-1-naphthyl group,
a 6-ethynyl-1-naphthyl group,
a 6-(2-fluoroethynyl)-1-naphthyl group,
a 6-fluoro-1-naphthyl group, a 6-chloro-1-naphthyl group,
a 2-naphthyl group, a 6-cyano-2-naphthyl group,
a 6-nitro-2-naphthyl group, a 6-carboxyl-2-naphthyl group,
a 6-hydroxyl-2-naphthyl group,
a 6-(N-methylcarbamido)-2-naphthyl group,
a 6-(N,N-dimethylcarbamido)-2-naphthyl group,
a 6-methyl-2-naphthyl group,
a 6-trifluoromethyl-2-naphthyl group,
a 6-methoxy-2-naphthyl group,
a 6-trifluoromethoxy-2-naphthyl group,
a 6-methylthio-2-naphthyl group,
a 6-methylsulfinyl-2-naphthyl group,
a 6-methylsulfonyl-2-naphthyl group,
a 6-methoxycarbonyl-2-naphthyl group,
a 6-vinyl-2-naphthyl group,
a 6-(2,2-difluorovinyl)-2-naphthyl group,
a 6-ethynyl-2-naphthyl group,
a 6-(2-fluoroethynyl)-2-naphthyl group,
a 6-fluoro-2-naphthyl group, a 6-chloro-2-naphthyl group,
a 2-pyridyl group, a 3-pyridyl group, a 4-pyridyl group,
a 2-quinolyl group, a 3-quinolyl group, a 4-quinolyl group,
a 2-furyl group, a 3-furyl group, a 2-thienyl group,
a 3-thienyl group and the like.

Examples of the phenyl group optionally having one or more atoms or groups selected from Group H include, for example:
a 2-fluorophenyl group, a 3-fluorophenyl group,
a 4-fluorophenyl group, a 3-chlorophenyl group,
a 4-chlorophenyl group, a 4-bromophenyl group,
a 3-methylphenyl group, a 4-methylphenyl group,
a 4-methoxyphenyl group, a 2-fluoro-4-chlorophenyl group,
a 3-fluoro-4-chlorophenyl group, a 2,4-difluorophenyl group,
a 2,3-difluorophenyl group, a 3,4-difluorophenyl group,
a 3,5-difluorophenyl group, and a 2,3,4-trifluorophenyl group.

Examples of the present amide compound, which is useful as an active ingredient of the noxious arthropod controlling agent of the present invention include, for example, the following amide compounds:

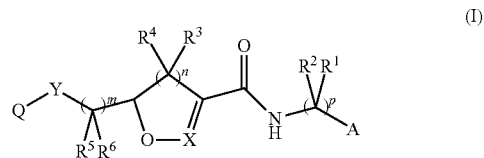

an amide compound in which X is a nitrogen atom in the formula (I);
an amide compound in which X is a CH group in the formula (I);
an amide compound in which p is 0 in the formula (I);
an amide compound in which p is 1 in the formula (I);
an amide compound in which $R^1$ is a C1-C3 alkyl group in the formula (I);
an amide compound in which $R^1$ is a hydrogen atom in the formula (I);
an amide compound in which $R^2$ is a C1-C3 alkyl group in the formula (I);
an amide compound in which $R^2$ is a hydrogen atom in the formula (I);
an amide compound in which $R^3$ is a C1-C3 alkyl group optionally having one or more halogen atoms in the formula (I);
an amide compound in which $R^3$ is a hydrogen atom in the formula (I);
an amide compound in which $R^4$ is a C1-C3 alkyl group optionally having one or more halogen atoms in the formula (I);
an amide compound in which $R^4$ is a hydrogen atom in the formula (I);
an amide compound in which n is 1 in the formula (I);
an amide compound in which n is 2 in the formula (I);
an amide compound in which $R^5$ is a C1-C4 alkyl group optionally having one or more halogen atoms in the formula (I);
an amide compound in which $R^5$ is a halogen atom in the formula (I);
an amide compound in which $R^5$ is a hydrogen atom in the formula (I);
an amide compound in which $R^6$ is a C1-C4 alkyl group optionally having one or more halogen atoms in the formula (I);
an amide compound in which $R^6$ is a halogen atom in the formula (I);
an amide compound in which $R^6$ is a hydrogen atom in the formula (I);
an amide compound in which Y is a single bond in the formula (I);
an amide compound in which Y is an oxygen atom in the formula (I);
an amide compound in which X is a nitrogen atom, $R^1$ is a hydrogen atom, and $R^2$ is a hydrogen atom in the formula (I):
an amide compound in which X is a CH group, $R^1$ is a hydrogen atom, and $R^2$ is a hydrogen atom in the formula (I);
an amide compound in which X is a nitrogen atom, n is 1, $R^1$ is a hydrogen atom, and $R^2$ is a hydrogen atom in the formula (I);

an amide compound in which X is a nitrogen atom, n is 2, $R^1$ is a hydrogen atom, and $R^2$ is a hydrogen atom in the formula (I);

an amide compound in which X is a CH group, n is 1, $R^1$ is a hydrogen atom, and $R^2$ is a hydrogen atom in the formula (I);

an amide compound in which X is a CH group, n is 2, $R^1$ is a hydrogen atom, and $R^2$ is a hydrogen atom in the formula (I);

an amide compound in which X is a nitrogen atom, $R^3$ is a hydrogen atom, and $R^4$ is a hydrogen atom in the formula (I);

an amide compound in which X is a CH group, $R^3$ is a hydrogen atom, and $R^4$ is a hydrogen atom in the formula (I);

an amide compound in which X is a nitrogen atom, n is 1, $R^3$ is a hydrogen atom, and $R^4$ is a hydrogen atom in the formula (I);

an amide compound in which X is a nitrogen atom, n is 2, $R^3$ is a hydrogen atom, and $R^4$ is a hydrogen atom in the formula (I);

an amide compound in which X is a CH group, n is 1, $R^3$ is a hydrogen atom, and $R^4$ is a hydrogen atom in the formula (I);

an amide compound in which X is a CH group, n is 2, $R^3$ is a hydrogen atom, and $R^4$ is a hydrogen atom in the formula (I);

an amide compound in which X is a nitrogen atom, $R^1$ is a hydrogen atom, $R^2$ is a hydrogen atom, $R^3$ is a hydrogen atom, and $R^4$ is a hydrogen atom in the formula (I);

an amide compound in which X is a CH group, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, n is 1, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, n is 2, $R^1$ is a hydrogen atom, $R^2$ is a hydrogen atom, $R^3$ is a hydrogen atom, and $R^4$ is a hydrogen atom in the formula (I);

an amide compound in which X is a CH group, n is 1, $R^1$ is a hydrogen atom, $R^2$ is a hydrogen atom, $R^3$ is a hydrogen atom, and $R^4$ is a hydrogen atom in the formula (I);

an amide compound in which X is a CH group, n is 2, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, p is 1, $R^1$ is a hydrogen atom, $R^2$ is a hydrogen atom, $R^3$ is a hydrogen atom, and $R^4$ is a hydrogen atom in the formula (I);

an amide compound in which X is a CH group, p is 1, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, p is 1, n is 1, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, p is 1, n is 2, $R^1$ is a hydrogen atom, $R^2$ is a hydrogen atom, $R^3$ is a hydrogen atom, and $R^4$ is a hydrogen atom in the formula (I);

an amide compound in which X is a CH group, p is 1, n is 1, $R^1$ is a hydrogen atom, $R^2$ is a hydrogen atom, $R^3$ is a hydrogen atom, and $R^4$ is a hydrogen atom in the formula (I);

an amide compound in which X is a CH group, p is 1, n is 2, $R^1$ is a hydrogen atom, $R^2$ is a hydrogen atom, $R^3$ is a hydrogen atom, and $R^4$ is a hydrogen atom in the formula (I);

an amide compound in which X is a nitrogen atom, p is 1, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a CH group, p is 1, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a nitrogen atom, p is 1, n is 1, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a nitrogen atom, p is 1, n is 2, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a CH group, p is 1, n is 1, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a CH group, p is 1, n is 2, $R^1$ is a hydrogen atom, $R^2$ is a hydrogen atom, $R^3$ is a hydrogen atom, $R^4$ is a hydrogen atom, and Y is a single bond in the formula (I);

an amide compound in which X is a nitrogen atom, p is 1, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a CH group, p is 1, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a nitrogen atom, p is 1, n is 1, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a nitrogen atom, p is 1, n is 2, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a CH group, p is 1, n is 1, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a CH group, p is 1, n is 2, $R^1$ is a hydrogen atom, $R^2$ is a hydrogen atom, $R^3$ is a hydrogen atom, $R^4$ is a hydrogen atom, and Y is an oxygen atom in the formula (I);

an amide compound in which X is a nitrogen atom, p is 1, n is 1, $R^1$ is a hydrogen atom, $R^2$ is a hydrogen atom, $R^3$ is a hydrogen atom, $R^4$ is a hydrogen atom, Y is an oxygen atom, and Q is a C1-C8 chain hydrocarbon group optionally having one or more atoms or groups selected from Group D in the formula (I);

an amide compound in which X is a nitrogen atom, p is 1, n is 1, $R^1$ is a hydrogen atom, $R^2$ is a hydrogen atom, $R^3$ is a hydrogen atom, $R^4$ is a hydrogen atom, Y is an oxygen atom, and Q is a C1-C8 chain hydrocarbon group optionally having a phenyl group optionally having one or more atoms or groups selected from Group D in the formula (I);

an amide compound in which X is a nitrogen atom, p is 1, n is 1, $R^1$ is a hydrogen atom, $R^2$ is a hydrogen atom, $R^3$ is a hydrogen atom, $R^4$ is a hydrogen atom, Y is an oxygen atom, and Q is a C1-C8 chain hydrocarbon group optionally having a naphthyl group optionally having one or more atoms or groups selected from Group D in the formula (I);
an amide compound in which X is a nitrogen atom, p is 0, $R^1$ is a hydrogen atom, $R^2$ is a hydrogen atom, $R^3$ is a hydrogen atom, and $R^4$ is a methyl group in the formula (I).

Then, a process for producing the present amide compound will be illustrated.

The present amide compound can be produced, for example, according to the following (Production Process 1) to (Production Process 4).

(Production Process 1)

The present amide compound can be produced by reacting Compound (1) and Compound (2) in the presence of a condensing agent.

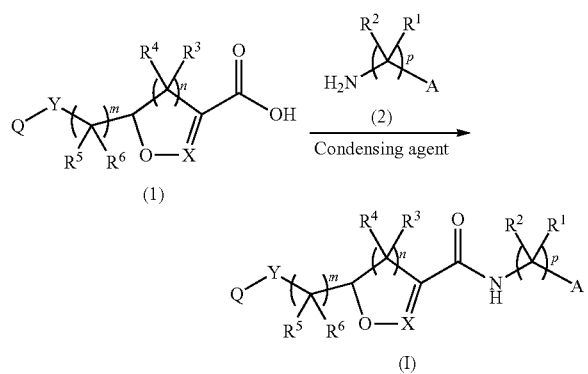

wherein X, Y, Q, $R^1$, $R^2$, $R^3$, $R^4$, $R^5$, $R^6$, m, n and p are as defined above.

The reaction is usually performed in a solvent in the presence of a condensing agent, if necessary, in the presence of a base.

Examples of the condensing agent used in the reaction include, for example, dicyclohexylcarbodiimide, 1-ethyl-3-(3-dimethylaminopropyl)carbodiimide hydrochloride, benzotriazol-1-yloxytris(dimethylamino)phosphonium hexafluorophosphate and (benzotriazol-1-yloxy)tripyrrolidinophosphonium hexafluorophosphate.

Examples of the base used in the reaction include, for example, carbonates such as sodium carbonate, potassium carbonate and the like, tertiary amines such as triethylamine, diisopropylethylamine, 1,8-diazabicyclo[5.4.0]undeca-7-ene, 1,5-diazabicyclo[4.3.0]non-5-ene and the like, and nitrogen-containing aromatic compounds such as pyridine, 4-dimethylaminopyridine and the like.

Examples of the solvent used in the reaction include, for example, aromatic hydrocarbons such as benzene, toluene and the like, hydrocarbons such as hexane and the like, ethers such as diethyl ether, tetrahydrofuran and the like, halogenated hydrocarbons such as dichloromethane, chloroform, 1,2-dichloroethane, chlorobenzene and the like, acid amides such as N,N-dimethylformamide and the like, and esters such as ethyl acetate, butyl acetate and the like.

The reaction can be also performed by, if necessary, adding 1-hydroxybenzotriazole, 1-hydroxy-7-azabenzotriazole, N-hydroxysuccinic acid imide or the like usually in an optional amount ranging from 0.01 mole to 1 mole, preferably 0.05 mole to 0.2 mole per mole of the compound (1).

A reaction time of the reaction is usually in a range of 5 minutes to 72 hours.

A reaction temperature of the reaction is usually in a range of −20° C. to 100° C. (provided that when a boiling point of a solvent to be used is lower than 100° C., −20° C. to a boiling point of a solvent).

In the reaction, a molar ratio between Compound (1) and Compound (2) that may be used can be optional. Preferred is equimolar or nearly equimolar amount, and is, for example, 1 mole to 3 moles of Compound (2) per mole of Compound (1).

The condensing agent is used in the reaction in an optional amount usually ranging from 1 mole to an excessive amount, preferably 1 mole to 3 moles, per mole of Compound (1).

The base used can be used in the reaction in an optional amount ranging from usually 1 mole to an excessive amount, preferably 1 mole to 3 moles, per mole of Compound (1).

After completion of the reaction, the present amide compound can be isolated by performing ordinary post-treatment operation such as organic solvent extraction, concentration and the like after pouring of the reaction mixture into water. In addition, the isolated present amide compound can be also purified by operation such as chromatography, recrystallization, distillation and the like.

(Production Process 2)

The present amide compound can be produced by reacting Compound (3) and Compound (2) in the presence of a base.

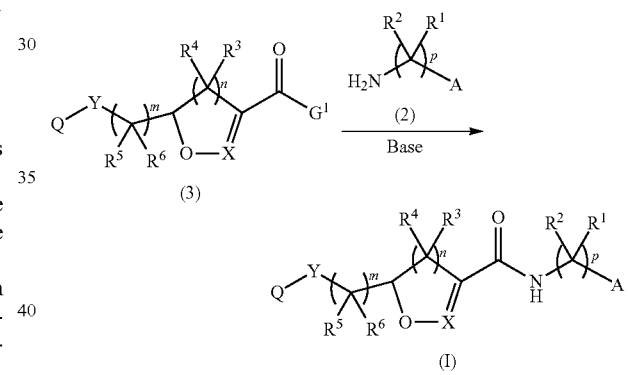

wherein $G^1$ represents a leaving group (e.g. chlorine atom, bromine atom etc.), and X, Y, Q, $R^1$, $R^2$, $R^3$, $R^4$, $R^5$, $R^6$, m, n and p are as defined above.

The reaction is performed in the presence of a base usually in a solvent.

Examples of the base used in the reaction include, for example, carbonates such as sodium carbonate, potassium carbonate and the like, tertiary amines such as triethylamine, diisopropylethylamine, 1,8-diazabicyclo[5.4.0]undeca-7-ene, 1,5-diazabicyclo[4.3.0]non-5-ene and the like, and nitrogen-containing aromatic compounds such as pyridine, 4-dimethylaminopyridine and the like.

Examples of the solvent used in the reaction include, for example, ethers such as 1,4-dioxane, tetrahydrofuran, ethylene glycol dimethyl ether, tert-butyl methyl ether and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile, butyronitrile and the like, acid amides such as N,N-dimethylformamide and the like, sulfoxides such as dimethyl sulfoxide and the like and a mixture thereof.

A reaction time of the reaction is usually in a range of 5 minutes to 72 hours.

A reaction temperature of the reaction is usually in a range of −20 to 100° C.

In the reaction, a molar ratio between Compound (3) and Compound (2) can be optional. Preferred is equimolar or nearly equimolar, and is specifically, 0.5 to 3 moles of Compound (2), per mole of Compound (3).

The base in the reaction can be used in an optional amount ranging usually 1 mole to an excessive amount, preferably 1 to 3 moles, per mole of Compound (3).

After completion of the reaction, the present amide compound can be isolated by performing ordinary post-treatment operation such as organic solvent extraction, concentration and the like after pouring of the reaction mixture into water. In addition, the isolated present amide compound can be also purified by operation such as chromatography, recrystallization, distillation and the like.

(Production Process 3)

The present amide compound can be also produced by reacting Compound (4) and Compound (5) in the presence of a base.

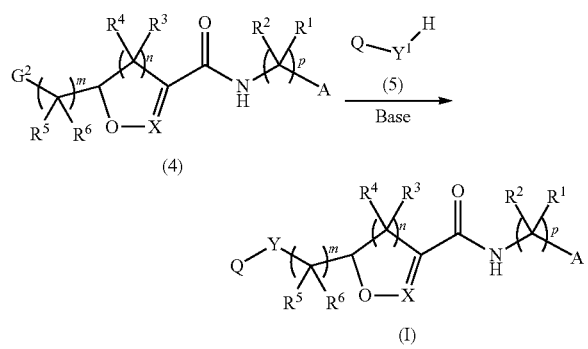

wherein $G^2$ represents a leaving group (e.g. chlorine atom, bromine atom, iodine atom, methanesulfonyloxy group, trifluoromethanesulfonyloxy group or 4-toluenesulfonyloxy group), $Y^1$ represents an oxygen atom or a sulfur atom, and X, Q, $R^1$, $R^2$, $R^3$, $R^4$, $R^5$, $R^6$, m, n and p are as defined above.

The reaction is performed in the presence of a base usually in a solvent.

Examples of the base used in the reaction include, for example, alkali metals such as sodium, potassium and the like, alkyllithiums such as n-butyllithium and the like, metal hydrides such as sodium hydride, potassium hydride and the like, carbonates such as sodium carbonate, potassium carbonate and the like, alkali metal alkoxides such as potassium-t-butoxide and the like, tertiary amines such as triethylamine, diisopropylethylamine, 1,8-diazabicyclo[5.4.0]undeca-7-ene, 1,5-diazabicyclo[4.3.0]non-5-ene and the like, and nitrogen-containing aromatic compounds such as pyridine, 4-dimethylaminopyridine and the like.

Examples of the solvent used in the reaction include, for example, ethers such as 1,4-dioxane, tetrahydrofuran, ethylene glycol dimethyl ether, tert-butyl methyl ether and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile, butyronitrile and the like, acid amides such as N,N-dimethylformamide and the like, sulfoxides such as dimethyl sulfoxide and the like and a mixture thereof.

A reaction time of the reaction is usually in a range of 5 minutes to 72 hours.

A reaction temperature of the reaction is usually in a range of −20 to 100° C.

In the reaction, a molar ratio between Compound (4) and Compound (5) can be optional. Preferred is an equimolar or nearly equimolar, and specifically, 0.5 to 3 moles of Compound (5), per mole of Compound (4).

The base is used in the reaction in an optional amount ranging usually 1 mole to an excessive amount, preferably 1 to 3 mole, per mole of Compound (5).

After completion of the reaction, the present amide compound can be isolated by performing ordinary post-treatment operation such as organic solvent extraction, concentration and the like after pouring of the reaction mixture into water. In addition, the isolated present amide compound can be also purified by operation such as chromatography, recrystallization, distillation and the like.

(Production Process 4)

The present amide compound (I-a) can be also produced by the following scheme, for example, in accordance with the process described in European Journal of Organic Chemistry, 4852-4860, (2006).

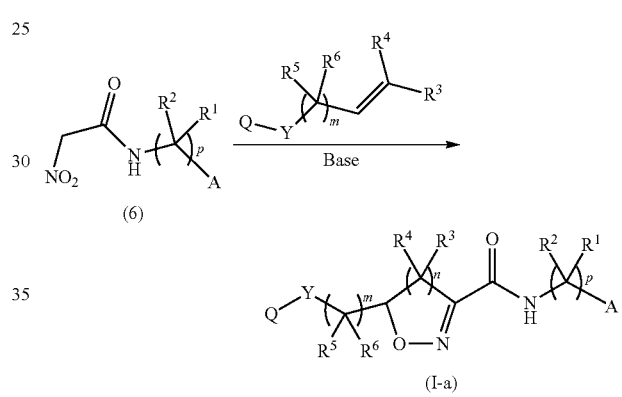

wherein Y, Q, $R^1$, $R^2$, $R^3$, $R^4$, $R^5$, $R^6$, m and p are as defined above.

Then, a process for producing a production intermediate of the present amide compound will be illustrated.

(Reference Production Process 1)

Compound (1) can be produced by subjecting Compound (8) to a hydrolysis reaction in the presence of a base.

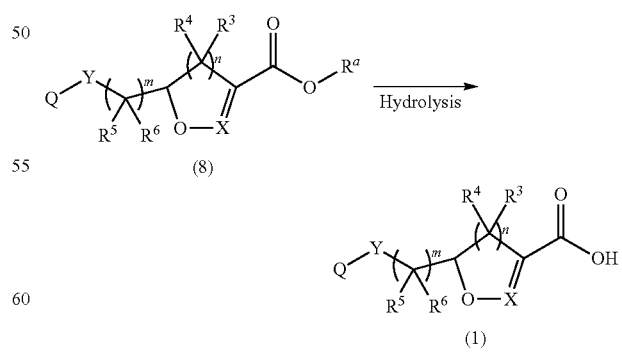

wherein $R^a$ represents a methyl group or an ethyl group, and X, Y, Q, $R^3$, $R^4$, $R^5$, $R^6$, m and n are as defined above.

The reaction is performed in the presence of a base in the presence of water and an organic solvent.

Examples of the base used in the reaction include, for example, alkali metal hydroxides such as lithium hydroxide, sodium hydroxide, potassium hydroxide and the like.

Examples of the solvent used in the reaction include, for example, ethers such as 1,4-dioxane, tetrahydrofuran, ethylene glycol dimethyl ether, tert-butyl methyl ether and the like, aromatic hydrocarbons such as toluene, xylene and the like, halogenated hydrocarbons such as chlorobenzene and the like, nitriles such as acetonitrile, butyronitrile and the like, alcohols such as methanol, ethanol, propanol and the like and a mixture thereof.

A reaction time of the reaction is usually in a range of 5 minutes to 72 hours.

A reaction temperature of the reaction is usually in a range of 0° C. to 100° C. (provided that when a boiling point of a solvent to be used is lower than 100° C., 0° C. to a boiling point of a solvent).

The base is used in the reaction in an optional amount ranging usually 1 mole to an excessive amount, preferably 1 mole to 5 moles, per mole of Compound (8).

After completion of the reaction, Compound (1) can be obtained by pouring the reaction mixture into water, washing the resultant with an organic solvent, neutralizing the aqueous layer with acidic water (hydrochloric acid etc.), and performing ordinary post-treatment operation such as organic solvent extraction, concentration and the like. Alternatively, the resulting Compound (1) can be usually used in a reaction in a next step without purification, and if necessary, Compound (1) can be also purified by operation such as chromatography, recrystallization and the like.

(Reference Production Process 2)

Compound (3) can be produced, for example, by reacting Compound (1) and a halogenating agent.

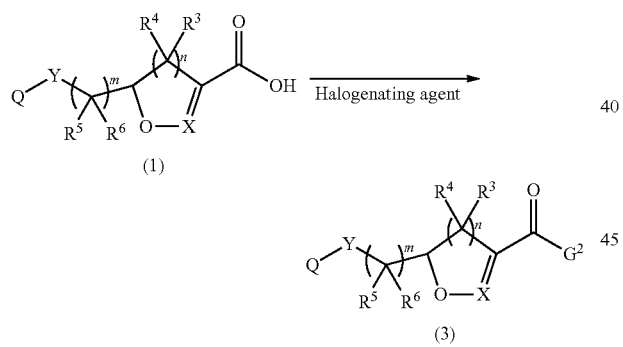

wherein $G^2$ represents a chlorine atom or a bromine atom, and X, Y, Q, $R^3$, $R^4$, $R^5$, $R^6$, m and n are as defined above.

The reaction is performed in a solvent, if necessary.

Examples of the halogenating agent used in the reaction include, for example, thionyl chloride, oxalyl chloride or phosphorus oxychloride.

Examples of the solvent used in the reaction include, for example, ethers such as 1,4-dioxane, tetrahydrofuran, ethylene glycol dimethyl ether, tert-butyl methyl ether and the like, aliphatic hydrocarbons such as hexane, heptane and the like, aromatic hydrocarbons such as toluene, xylene and the like, halogenated hydrocarbons such as chlorobenzene and the like and a mixture thereof.

A reaction time of the reaction is usually in a range of 5 minutes to 24 hours.

A reaction temperature of the reaction is usually in a range of 0 to 100° C.

The halogenating agent is used in the reaction in an optional amount ranging usually 1 mole to an excessive amount, preferably 1 to 5 moles, per mole of Compound (1).

After completion of the reaction, Compound (3) can be isolated by performing post-treatment operation such as concentration of the reaction mixture as it is. The isolated Compound (3) is usually used in a reaction of a next step without purification, and if necessary, purified by distillation or the like.

(Reference Production Process 3)

Compound (8-a) can be also produced by the following scheme, in accordance with the process described, for example, in Bioorganic and Medicinal Chemistry Letters, 18, 5211, (2008).

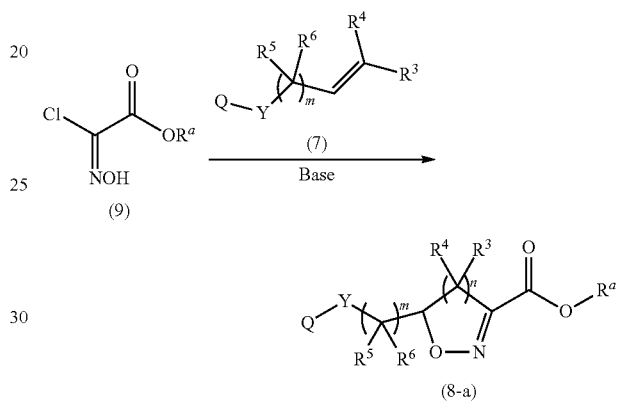

wherein $R^a$ represents a methyl group or an ethyl group, and Y, Q, $R^3$, $R^4$, $R^5$, $R^6$ and m are as defined above.

(Reference Production Process 4)

Compound (8-a) can be also produced by the following scheme, in accordance with the process described, for example, in European Journal of Organic Chemistry, 4852-4860, (2006).

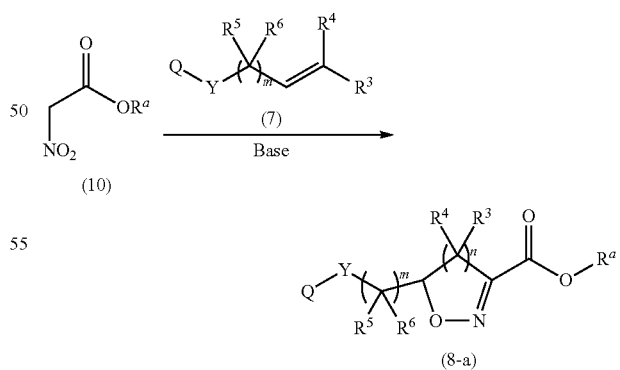

wherein $R^a$ represents a methyl group or an ethyl group, and X, Y, Q, $R^3$, $R^4$, $R^5$, $R^6$ and m are as defined above.

(Reference Production Process 5)

Compound (8) can be produced, for example, by reacting Compound (11) and Compound (5) in the presence of a base.

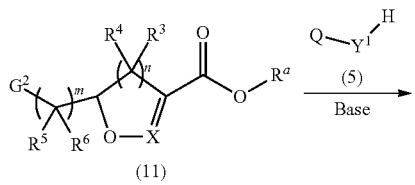

(11)

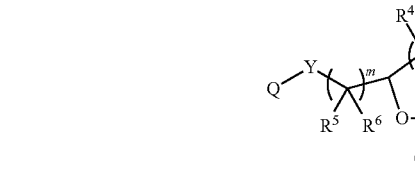

(8)

wherein $G^2$ represents a leaving group (e.g. chlorine atom, bromine atom, iodine atom, methanesulfonyloxy group, trifluoromethanesulfonyloxy group or 4-toluenesulfonyoxy group), $Y^1$ represents an oxygen atom or a sulfur atom, $R^a$ represents a methyl group or an ethyl group, and X, Q, $R^3$, $R^4$, $R^5$, $R^6$, m, and n are as defined above.

The reaction is performed in the presence of a base usually in a solvent.

Examples of the base used in the reaction include alkali metals such as sodium, potassium and the like, alkyllithiums such as n-butyllithium and the like, metal hydrides such as sodium hydride, potassium hydride and the like, carbonates such as sodium carbonate, potassium carbonate and the like, alkali metal alkoxides such as potassium-t-butoxide and the like, tertiary amines such as triethylamine, diisopropylethylamine, 1,8-diazabicyclo[5.4.0]undeca-7-ene, 1,5-diazabicyclo[4.3.0]non-5-ene and the like, and nitrogen-containing aromatic compounds such as pyridine, 4-dimethylaminopyridine and the like.

Examples of the solvent used in the reaction include, for example, ethers such as 1,4-dioxane, tetrahydrofuran, ethylene glycol dimethyl ether, tert-butyl methyl ether and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile, butyronitrile and the like, acid amides such as N,N-dimethylformamide and the like, sulfoxides such as dimethyl sulfoxide and the like and a mixture thereof.

A reaction time of the reaction is usually in a range of 5 minutes to 72 hours.

A reaction temperature of the reaction is usually in a range of −20 to 100° C.

In the reaction, a molar ratio between a compound of formula (11) and a compound of formula (5) can be optional. Preferred is equimolar or nearly equimolar amount, and is specifically 0.5 to 3 moles of the compound of formula (5) per mole of the compound of formula (11).

The base can be used in the reaction in an optional amount ranging usually 1 mole to an excessive amount, preferably 1 to 3 moles per mole of the compound of formula (5).

After completion of the reaction, Compound (8) can be isolated by performing ordinary post-treatment operation such as organic solvent extraction, concentration and the like after pouring of the reaction mixture into water. In addition, the isolated Compound (8) can be also purified by operation such as chromatography, recrystallization, distillation and the like.

(Reference Production Process 6)

Compound (1) can be also produced by converting Compound (11) into Compound (8) in accordance with the process described in Reference Production Process 5, and thereafter, subjecting this to a hydrolysis reaction without purification in accordance with the process described in Reference Production Process 1.

Step 1

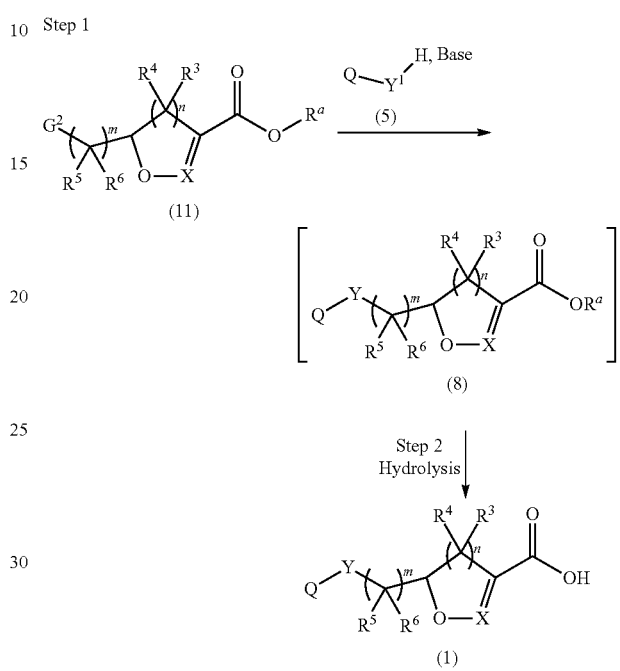

wherein $G^2$, $Y^1$, Q, $R^a$, $R^3$, $R^4$, $R^5$, $R^6$, m and n are as defined above.

(Reference Production Process 7)

Compound (11-a) can be also produced by the following scheme in accordance with the process described, for example, in Journal of Chemical Society, Parkin Trans 1, 206-215 (2001).

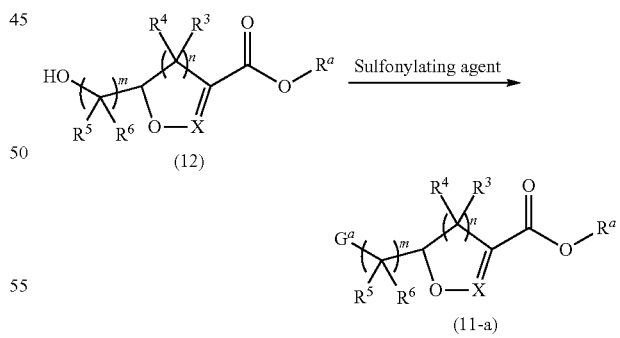

wherein $G^a$ represents a leaving group (e.g. methanesulfonyloxy group, trifluoromethanesulfonyloxy group or 4-toluenesulfonyloxy group), and $R^a$, $R^3$, $R^4$, $R^5$, $R^6$, m and n are as defined above.

(Reference Production Process 8)

Compound (11-b) can be also produced by the following scheme in accordance with the process described, for example, in Chemistry-A European Journal, 993-1005 (2001).

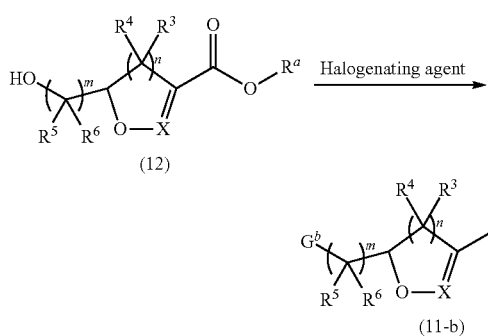

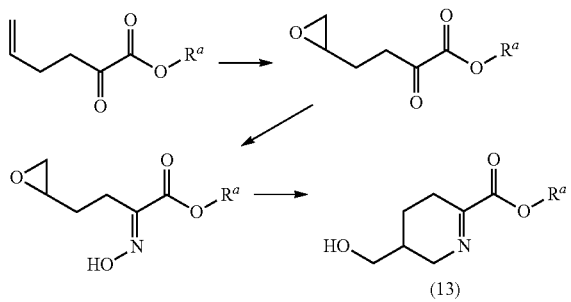

wherein $G^b$ represents a chlorine atom, a bromine atom, or an iodine atom, and $R^a$, $R^3$, $R^4$, $R^5$, $R^6$, m and n are as defined above.

(Reference Production Process 9)

Compound (13) can be also produced by the following scheme in accordance with the process described, for example, in Tetrahedron Letters, 48 (2007), 5201-5204.

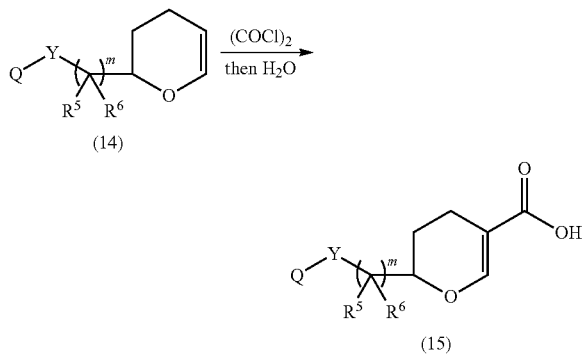

wherein $R^a$ represents a methyl group or an ethyl group.

(Reference Production Process 10)

Compound (15) can be also produced by the following scheme in accordance with the process described, for example, in Journal of Heterocyclic Chemistry 47 (2010), 1171-1175.

wherein Q, Y, $R^5$, $R^6$ and m are as defined above.

The noxious arthropod on which the present amide compound has a control effect includes noxious insects and noxious mites. More specifically, examples are as described below.

Hemiptera: Delphacidae such as *Laodelphax striatellus*, *Nilaparvatalugens* and *Sogatella furcifera*;

Deltocephalidae such as *Nephotettix cincticeps* and *Nephotettix virescens*;

Aphididae such as *Aphis gossypii* and *Myzus persicae*;

Pentatomidae such as *Nezara antennata*, *Riptortus clavetus*, *Eysarcoris lewisi*, *Bemisia argentifolii*, *Eysarcoris parvus*, *Plautia stali*, *Halyomorpha mista*, *Stenotus rubrovittatus* and *Trigonotylus ruficornis*;

Aleyrodidae such as *Trialeurodes vaporariorum* and *Bemisia argentifolii*;

Coccidae such as *Aonidiella aurantii*, *Comstockaspis perniciosa*, *Unaspis citri*, *Ceroplastes rubens* and *Icerya purchasi*;

Tingidae;

Cimicoidea such as *Cimex lectularius*;

Psyliidae, etc.;

Lepidoptera: Pyralidae such as *Chilo suppressalis*, *Cnaphalocrocis medinalis*, *Notarcha derogata* and *Plodia interpunctella*;

Noctuidae such as *Spodoptera litura*, *Pseudaletia separata*, *Trichoplusia* spp., *Heliothis* spp., and *Helicoverpa* spp.;

Pieridae such as *Pieris rapae*;

Tortricidae such as *Adoxophyes* spp., *Grapholita molesta* and *Cydia pomonella*;

Carposinidae such as *Carposina niponensis*;

Lyonetiidae such as *Lyonetia* spp.;

Lymantriidae such as *Lymantria* spp. and *Euproctis* spp.;

Yponomeutidae such as *Plutella xylostella*;

Gelechiidae such as *Pectinophora gossypiella*;

Arctiidae such as *Hyphantria cunea*;

Tineidae such as *Tinea translucens* and *Tineolabisselliella*, etc.;

Diptera: Culices such as *Culex pipiens pallens*, *Culex tritaeniorhynchus* and *Culex quinquefasciatus*;

Aedes spp. such as *Aedes aegypti* and *Aedes albopictus*;

Anopheles spp. such as *Anopheles sinensis*;

Chironomidae;

Muscidae such as *Musca domestica* and *Muscina stabulans*;

Calliphoridae;

Sarcophagidae;

Fanniidae;

Anthomyiidae such as *Delia platura* and *Delia antiqua*;

Agromyzidae such as *Liriomyza trifolii*;

Tephritidae;

Drosophilidae;

Phoridae such as *Megaselia spiracularis*;

Psychodidae such as *Clogmia albipunctata*;

Simuliidae;

Tabanidae, Stomoxys, etc.;

Coleoptera: *Diabrotica* spp. such as *Diabrotica virgifera virgifera* and *Diabrotica undecimpunctata howardi*;

Scarabaeidae such as *Anomala cuprea* and *Anomala rufocuprea*;

Curculionidae such as *Sitophilus zeamais*, *Lissorhoptrus oryzophilus* and *Callosobruchuys chienensis*;

Heteromera such as *Tenebrio molitor* and *Tribolium castaneum*;

Chrysomelidae such as *Oulema oryzae*, *Aulacophora femoralis*, *Phyllotreta striolata* and *Leptinotarsa decemlineata*;

Dermestidae such as *Dermestes maculates*;

Anobiidae;

*Epilachna* such as *Epilachna vigintioctopunctata*;

Lyctidae, Bostrychidae, Ptinidae, Cerambycidae, *Paederus fuscipes*, etc.;

Blattodea: *Blattella germanica, Periplaneta fuliginosa, Periplaneta americana, Periplaneta brunnea, Blatta orientalis*, etc.;
Thysanoptera: *Thrips palmi, Thrips tabaci, Frankliniella occidentalis, Frankliniella intonsa*, etc.;
Hymenoptera: Formicidae such as *Monomorium pharaosis, Formica fusca japonica, Ochetellus glaber, Pristomyrmex pungens* and *Pheidole noda;*
Vespidae;
Bethylidae;
Tenthredinidae such as *Athalia japonica*, etc.;
Orthoptera: Gryllotalpidae, Acrididae, Grylloidea, etc.;
Siphonaptera: *Ctenocephalides felis, Ctenocephalides canis, Pulex irritans, Xenopsylla cheopis*, etc.;
Anoplura: *Pediculus humanus corporis, Phthirus pubis, Haematopinus eurysternus, Dalmalinia ovis, Haematopinus suis*, etc.;
Termitidae: Subterranean termites such as *Reticulitermes speratus, Coptotermes formosanus, Reticulitermes flavipes, Reticulitermes hesperus, Reticulitermes virginicus, Reticulitermes tibialis* and *Heterotermes aureus;*
Drywood termites such as *Incisitermes minor;*
Dampwood termites such as *Zootermopsis nevadensis*, etc.;
Acari: Tetranychidae such as *Tetranychus urticae, Tetranychus kanzawai, Panonychus citri, Panonychus ulmi* and *Oligonychus* spp.;
Eriophyidae such as *Aculops lycopers, Aculops pelekassi* and *Aculus schlechtendali;*
Tarsonemidae such as *Polyphagotarsonemus latu;*
Tenuipalpidae;
Tuckerellidae;
Ixodidae such as *Haemaphysalis longicornis, Haemaphysalis flava, Dermacentor variabilis, Haemaphysalis flava, Dermacentor taiwanicus, Ixodes ovatus, Ixodes persulcatus, Ixodes scapularis, Boophilus microplus, Amblyomma americanum* and *Rhipicephalus sanguineus;*
Acaridae such as *Tyrophagus putrescentiae;*
Pyroglyphidae such as *Dermatophagoides farinae* and *Dermatophagoides pteronyssinus;*
Cheyletidae such as *Cheyletus eruditus, Cheyletus malaccensis* and *Cheyletus moorei;*
Dermanyssidae such as *Ornithonyssus bacoti, Ornithonyssus sylvairum* and *Dermanyssus gallinae;*
Trombiculidae such as *Leptotrombidium akamushi*, etc.;
Araneae: *Chiracanthium japonicum, Latrodectus hasseltii*, etc.;
Chilopoda: *Thereuonema hilgendorfi, Scolopendra subspinipes*, etc.;
Diplopoda: *Oxidus gracilis, Nedyopus tambanus*, etc.;
Isopoda: *Armadillidium vulgare*, etc.;

The noxious arthropod controlling agent of the present invention contains the present amide compound and an inert carrier. The inert carrier represents a bulking agent, a diluent or the like which is used in the epidemic prevention and agricultural fields. The noxious arthropod controlling agent of the present invention is usually formulated into a formulation such as an emulsifiable concentrate, an oil solution, a dust formulation, a granule, a wettable powder, a flowable, a microcapsule, an aerosol, a fumigant, a poisonous bait, a resin formulation or the like, by mixing the present amide compound with an inert carrier such as a solid carrier, a liquid carrier, a gaseous carrier and the like and, if necessary, adding a surfactant, and other auxiliaries for formulation. These formulations usually contain the present amide compound at 0.01 to 95% by weight.

Examples of the solid carrier which is used in the formulation include, for example, fine powder and granules of clay materials (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.) and the like.

Examples of the liquid carrier include, for example, water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc).

Examples of the gaseous carrier include, for example, fluorocarbon, butane gas, LPG (liquefied petroleum gas), dimethyl ether, and carbon dioxide.

Examples of the surfactant include, for example, nonionic surfactants such as polyoxyethylene alkyl ether, polyoxyethylene alkylaryl ether and polyethylene glycol fatty acid ester, and anionic surfactants such as alkylsulfonates, alkylbenzene sulfonates and alkylsulfates.

The other auxiliaries for formulation include fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

The noxious arthropod can be controlled, for example, by applying the noxious arthropod controlling agent of the present invention directly to the noxious arthropod and/or to a habitat of the noxious arthropod.

A method for controlling the noxious arthropod is not particularly limited as far as the amide compound is in a form which can be substantially applied, and is performed, for example, by applying an effective amount of the present amide compound to the noxious arthropod or a habitat of the noxious arthropod. The amide compound is usually used in a form of the noxious arthropod controlling agent.

The habitat where noxious arthropod inhabits includes paddy fields, fields, orchards, non-agricultural lands, houses and the like.

The application can be carried out by the application method similar to the conventional one, as long as the present amide compound can be brought into contact with or ingested by a noxious arthropod.

Examples of the application method include, for example, spraying treatment, soil treatment, seed treatment and water culture medium treatment.

When the noxious arthropod controlling agent of the present invention is used for controlling noxious arthropod in the field of agriculture, the application amount of the amide compound is usually 1 to 10000 g per 10000 m$^2$. When the noxious arthropod controlling agent of the present invention is formulated into an emulsifiable concentrate, a wettable powder, a flowable or the like, the noxious arthropod controlling agent is usually diluted with water so as to have a concentration of the active ingredient of 0.01 to 10000 ppm, and dust formulations, granules and the like are usually applied as they are.

These formulations and formulation solutions diluted with water may be directly treated by being sprayed on a noxious arthropod or a plant such as crops which should be protected from a noxious arthropod, and also may be treated on a soil in order to control a noxious arthropod that inhabits in the soil of cultivated land.

Also, the resin formulation processed into a sheet or string can be also treated by a method such as winding it around crops, spreading it in the vicinity of crops, or spreading it to the soil around crop roots.

When the noxious arthropod controlling agent of the present invention is used in controlling the noxious arthropod that inhabits in the house, the application amount of the amide compound is usually 0.01 to 1000 mg per m$^2$ of an area to be treated, in the case of using it on a planar area, and it is usually 0.01 to 500 mg per m$^2$ of a space to be treated, in the case of using it in a space. When the noxious arthropod controlling agent of the present invention is formulated into an emulsifiable concentrate, a wettable powder, a flowable or the like, the noxious arthropod controlling agent is usually diluted with water so as to have the active ingredient at a concentration of 0.1 to 1000 ppm and applied, and oil formulations, aerosols, fumigants, poisonous baits and the like are applied as they are.

The present amide compound can be used in the farmland where the following crops are grown.

Crops; corn, rice, wheat, barley, rye, oat, sorghum, cotton, soybean, peanut, buckwheat, beet, rapeseed, sunflower, sugar cane, tobacco, etc.

Vegetables; Solanaceous vegetables (eggplant, tomato, pimento, pepper, potato, etc.), Cucurbitaceous vegetables (cucumber, pumpkin, zucchini, watermelon, melon, etc.), Cruciferous vegetables (Japanese radish, white turnip, horseradish, kohlrabi, Chinese cabbage, cabbage, leaf mustard, broccoli, cauliflower, etc.), Asteraceous vegetables (burdock, crown daisy, artichoke, lettuce, etc.), Liliaceous vegetables (green onion, onion, garlic, asparagus, etc.), Ammiaceous vegetables (carrot, parsley, celery, parsnip, etc.), Chenopodiaceous vegetables (spinach, Swiss chard, etc.), lamiaceous vegetables (*Perilla frutescens*, mint, basil, etc.), strawberry, sweet potato, *Dioscorea japonica, colocasia*, etc.

Flowers;

Ornamental foliage plants;

Fruit; pomaceous fruits (apple, pear, Japanese pear, Chinese quince, quince, etc.), stone fruits (peach, plum, nectarine, *Prunus mume*, cherry fruit, apricot, prune, etc.), citrus plants (Citrus unshu, orange, lemon, lime, grapefruits, etc.), nuts (chestnut, walnuts, hazelnuts, almond, pistachio, cashew nuts, macadamia nuts, etc.), berry fruits (blueberry, cranberry, raspberry, etc.), grape, kaki persimmon, olive, Japanese plum, banana, coffee, date palm, coconuts, etc.;

Trees other than fruit trees; tea, mulberry, flowering plant, roadside trees (ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Pieca, Taxus cuspidate*), etc.

The crops also include genetically modified crops.

The noxious arthropod controlling agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos, diazinon, DCIP (dichlorodiisopropyl ether), dichlofenthion, dichlorvos, dimethoate, dimethylvinphos, disulfoton, EPN, ethion, ethoprophos, etrimfos, fenthion, fenitrothion, fosthiazate, formothion, Hydrogen phosphide, isofenphos, isoxathion, malathion, mesulfenfos, methidathion, monocrotophos, naled, oxydeprofos, parathion, phosalone, phosmet, pirimiphos-methyl, pyridafenthion, quinalphos, phenthoate, profenofos, propaphos, prothiofos, pyraclorfos, salithion, sulprofos, tebupirimfos, temephos, tetrachlorvinphos, terbufos, thiometon, trichlorphon, vamidothion, phorate, and cadusafos.

(2) Carbamate Compounds alanycarb, bendiocarb, benfuracarb, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, oxamyl, pirimicarb, propoxur, XMC, thiodicarb, xylylcarb, and aldicarb.

(3) Pyrethroid Compounds acrinathrin, allethrin, beta-cyfluthrin, bifenthrin, cycloprothrin, cyfluthrin, cyhalothrin, cypermethrin, deltamethrin, esfenvalerate, etofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, and dimefluthrin.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof.

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide
machine oil and nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, and cyantraniliprole.

Active Ingredients of Miticide
acequinocyl, amitraz, benzoximate, bifenaate, bromopropylate, chinomethionat, chlorbenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, spiromesifen, spirotetramat, amidoflumet, and cyenopyrafen.

Active Ingredients of Nematicide
DCIP, fosthiazate, levamisol hydrochloride (levamisol), methylisothiocyanate, morantel tartarate, and imicyafos.

Active Ingredients of Fungicide
Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;
Cyclic amine fungicidal compounds such as fenpropimorph, tridemorph, and fenpropidin;
Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil; and tiadinil.

Active Ingredients of Plant Growth Regulator
ethephon, chlormequat-chloride, mepiquat-chloride, Gibberellin A, a representative of which is Gibberellin A3, abscisic acid, Kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, and 5-(trifluoromethyl)benzo[b]thiophene-2-carboxylic acid.

Active Ingredients of Herbicide
(1) Phenoxy Fatty Acid Herbicidal Compounds
2,4-PA, MCP, MCPB, phenothiol, mecoprop, fluroxypyr, triclopyr, clomeprop, and naproanilide.
(2) Benzoate Herbicidal Compounds
2,3,6-TBA, dicamba, clopyralid, picloram, aminopyralid, quinclorac, and quinmerac.
(3) Urea Herbicidal Compounds
diuron, linuron, chlortoluron, isoproturon, fluometuron, isouron, tebuthiuron, methabenzthiazuron, cumyluron, daimuron, and methyl-daimuron.
(4) Triazine Herbicidal Compounds
atrazine, ametoryn, cyanazine, simazine, propazine, simetryn, dimethametryn, prometryn, metribuzin, triaziflam, and indaziflam.
(5) Bipyridinium Herbicidal Compounds
paraquat, and diquat.
(6) Hydroxybenzonitrile Herbicidal Compounds
bromoxynil, and ioxynil.
(7) Dinitroaniline Herbicidal Compounds
pendimethalin, prodiamine, and trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPIC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.
(12) Diphenyl Ether Herbicidal Compounds
acifluorfen-sodium, bifenox, oxyfluorfen, lactofen, fomesafen, chlomethoxynil, and aclonifen.
(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds
benzofenap, pyrazolate, pyrazoxyfen, topramezone, and pyrasulfotole.
(15) Triketone Herbicidal Compounds
isoxaflutole, benzobicyclon, sulcotrione, mesotrione, tembotrione, and tefuryltrione.
(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.
(20) Sulfonamide Herbicidal Compounds
flumetsulam, metosulam, diclosulam, florasulam, cloransulam-methyl, penoxsulam, and pyroxsulam.

(21) Pyrimidinyloxybenzoate herbicidal compounds
pyrithiobac-sodium, bispyribac-sodium, pyriminobac-methyl, pyribenzoxim, pyriftalid, and pyrimisulfan.
(22) Other herbicidal compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist
piperonyl butoxide, sesamex, sulfoxide, N-(2-ethylhexyl)-8,9,10-trinorborn-5-ene-2,3-dicarboximide (MGK 264), N-decylimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

Hereinbelow, the present invention will be further illustrated by production examples, formulation examples, test examples, and the like. However, the present invention is not limited to these examples.

First, the production examples of the present amide compounds are shown below.

Production Example 1

Tetrahydrofuran-3-ylmethylamine hydrochloride (0.55 g, 4.0 mmol) was added to chloroform (Amylene-added product) (4 mL). After 5-butyl-4,5-dihydroisoxazole-3-carboxylic acid (0.68 g, 4.00 mmol) and 1-ethyl-3-(3-dimethylaminopropyl)carbodiimide hydrochloride (0.77 g, 4.0 mmol) were added to the mixed liquid at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.48 g of N-(tetrahydrofuran-3-ylmethyl)-5-butyl-4,5-dihydroisoxazole-3-carboxamide (hereinafter, referred to as present amide compound (1)) of following formula:

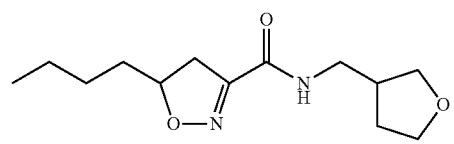

(1)

MS (ESI) m/z [M+H]⁺; 255.

Production Example 2

Tetrahydrofuran-3-ylmethylamine hydrochloride (5.50 g, 39.8 mmol) was dissolved in 70 mL of chloroform (Amylene-added product), triethylamine (5.6 mL, 39.8 mmol) was added, and the mixture was stirred at room temperature for 30 minutes. To the mixed liquid were added 5-pentyl-4,5-dihydroisoxazole-3-carboxylic acid (6.15 g, 33.2 mmol), 1-ethyl-3-(3-dimethylaminopropyl)carbodiimide hydrochloride (7.70 g, 39.8 mmol) and 1-hydroxybenzotriazole (0.45 g, 3.32 mmol) at room temperature, and the mixture was stirred at room temperature overnight. Thereafter, 83 mL of 1N hydrochloric acid was added to the reaction mixture, followed by extraction with ethyl acetate. The organic layer was washed with an aqueous saturated sodium bicarbonate solution, then, washed with an aqueous saturated sodium chloride solution, dried with anhydrous magnesium sulfate, and filtered, and the filtrate was concentrated under reduced pressure. The resulting residue was subjected to silica gel column chromatography to obtain 5.0 g of N-(tetrahydrofuran-3-ylmethyl)-5-pentyl-4,5-dihydroisoxazole-3-carboxyamide (hereinafter, referred to as present amide compound (2)) of following formula:

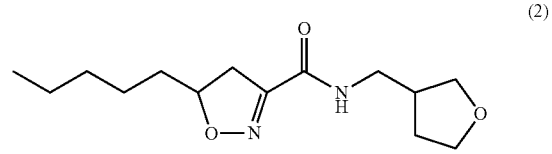 [SMILES: CCCCCC1CC(C(=O)NCC2CCOC2)=NO1]

(2)

¹H-NMR (CDCl₃) δ: 6.85-6.69 (1H, m, br), 4.83-4.72 (1H, m), 3.90 (1H, td, J=8.3, 5.4 Hz), 3.84 (1H, dd, J=8.8, 7.0 Hz), 3.75 (1H, dd, J=15.4, 7.9 Hz), 3.55 (1H, dd, J=8.8, 5.4 Hz), 3.37 (2H, t, J=6.7 Hz), 3.27 (1H, dd, J=17.7, 10.9 Hz), 2.87 (1H, dd, J=17.7, 8.4 Hz), 2.57-2.46 (1H, m), 2.10-2.02 (1H, m), 1.79-1.70 (1H, m), 1.68-1.54 (2H, m), 1.48-1.26 (6H, m) 0.90 (3H, dd, J=8.3, 5.5 Hz).

Production Example 3

Tetrahydrofuran-3-ylmethylamine hydrochloride (0.33 g, 2.40 mmol) was added to chloroform (Amylene-added product) (5 mL). After to the mixed liquid were added 5-benzyl-4,5-dihydroisoxazole-3-carboxylic acid (0.41 g, 2.00 mmol), 1-hydroxybenzotriazole (0.03 g, 0.24 mmol) and 1-ethyl-3-(3-dimethylaminopropyl)carbodiimide hydrochloride (0.46 g, 2.4 mmol) at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.50 g of N-(tetrahydrofuran-3-ylmethyl)-5-benzyl-4,5-dihydroisoxazole-3-carboxamide (hereinafter, referred to as present amide compound (3)) of following formula:

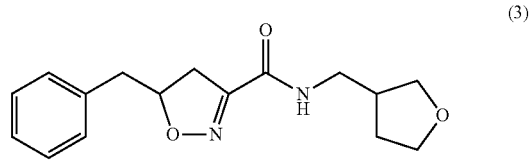 [SMILES: O=C(NCC1CCOC1)C1=NOC(Cc2ccccc2)C1]

(3)

MS (ESI) m/z [M+H]⁺: 289.

Production Example 4

Tetorahydrofuran-3-ylmethylamine hydrochloride (2.26 g, 32.9 mmol) was dissolved in 34 mL of chloroform (Amylene-added product), triethylamine (2.3 mL, 32.9 mmol) was added, and the mixture was stirred at room temperature for 30 minutes. To the mixed liquid were added 5-phenethyl-4,5-dihydroisoxazole-3-carboxylic acid (3.00 g, 27.4 mmol), 1-ethyl-3-(3-dimethylaminopropyl)carbodiimide hydrochloride (3.15 g, 32.9 mmol) and 1-hydroxybenzotriazole (0.19 g, 2.74 mmol) at room temperature, and the mixture was stirred at room temperature overnight. Thereafter, 40 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 3.00 g of N-(tetrahydrofuran-3-ylmethyl)-5-phenethyl-4,5-dihydroisoxa zole-3-carboxamide (hereinafter, referred to as present amide compound (4)) of following formula:

(4)

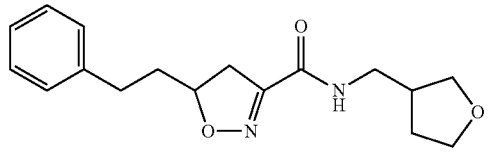

$^1$H-NMR (CDCl$_3$) δ: 7.33-7.27 (2H, m), 7.25-7.20 (2H, m), 7.20-7.17 (1H, m), 6.81-6.71 (1H, m, br), 4.80-4.72 (1H, m), 3.90 (1H, td, J=8.3, 5.4 Hz), 3.84 (1H, dd, J=8.8, 7.0 Hz), 3.75 (1H, td, J=7.9, 7.3 Hz), 3.55 (1H, dd, J=8.8, 5.2 Hz), 3.37 (2H, dt, J=9.3, 3.3 Hz), 3.28 (1H, ddd, J=17.7, 10.8, 0.7 Hz), 2.90 (1H, ddd, J=17.8, 8.3, 0.8 Hz), 2.82-2.68 (2H, m), 2.57-2.47 (1H, m), 2.12-2.02 (2H, m), 1.95-1.86 (1H, m), 1.65 (1H, dd, J=13.1, 7.5 Hz).

Production Example 5

Tetrahydrofran-3-ylmethylamine hydrochloride (0.33 g, 2.40 mmol) was added to chloroform (Amylene-added product) (5 mL). After to the mixed liquid were added 5-(phenoxymethyl)-4,5-dihydroisoxazole-3-carboxylic acid (0.44 g, 2.00 mmol), 1-hydroxybenzotriazole (0.03 g, 0.24 mmol) and 1-ethyl-3-(3-dimethylaminopropyl)carbodiimide hydrochloride (0.46 g, 2.4 mmol) at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.39 g of N-(tetrahydrofran-3-ylmethyl)-5-(phenoxymethyl)-4,5-dihydro isoxazole-3-carboxamide (hereinafter, referred to as present amide compound (5)) of following formula:

(5)

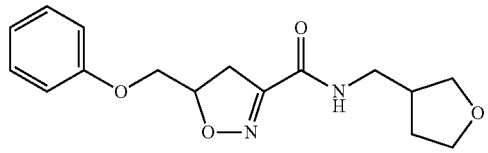

MS (ESI) m/z [M+H]$^+$: 305.

Production Example 6

Tetorahydrofuran-3-ylmethylamine hydrochloride (0.30 g, 2.24 mmol) was dissolved in 4.7 mL of chloroform (Amylene-added product), triethylamine (0.31 mL, 2.24 mmol) was added, and the mixture was stirred at room temperature for 30 minutes. To the mixed liquid were added 5-(2-phenoxyethyl)-4,5-dihydroisoxazole-3-carboxylic acid (0.44 g, 1.87 mmol), 1-ethyl-3-(3-dimethylaminopropyl) carbodiimide hydrochloride (0.43 g, 2.24 mmol) and 1-hydroxybenzotriazole (0.025 g, 0.19 mmol) at room temperature, and the mixture was stirred at room temperature overnight. Thereafter, 5.6 ml of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.38 g of N-(tetrahydrofran-3-ylmethyl)-5-(2-phenoxyethyl)-4,5-dihydroisoxazole-3-carboxamide (hereinafter, referred to as present amide compound (6)) of following formula:

(6)

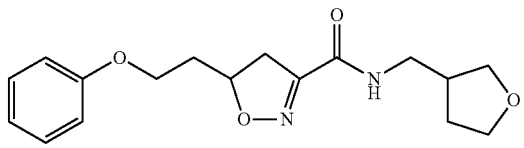

$^1$H-NMR (CDCl$_3$) δ: 7.29 (2H, dd, J=8.7, 7.6 Hz), 6.96 (1H, t, J=7.4 Hz), 6.89 (2H, dd, J=8.6, 1.0 Hz), 6.78-6.68 (1H, m, br), 5.09-5.01 (1H, m), 4.16-4.06 (3H, m), 3.89 (1H, td, J=8.1, 5.6 Hz), 3.84-3.80 (1H, m), 3.75 (1H, q, J=7.7 Hz), 3.53 (1H, dd, J=8.8, 5.4 Hz), 3.41-3.32 (3H, m), 3.07 (1H, ddd, J=17.8, 7.8, 0.9 Hz), 2.55-2.45 (1H, m), 2.22-2.07 (2H, m), 1.63 (1H, dd, J=13.2, 7.4 Hz).

Production Example 7

Tetrahydrofuran-3-ylmethylamine hydrochloride (0.24 g, 1.73 mmol) was dissolved in 2.0 mL of chloroform (Amylene-added product), triethylamine (0.24 mL, 1.73 mmol) was added, and the mixture was stirred at room temperature for 30 minutes. To the mixed liquid were added a solution of 5-(3-phenoxypropyl)-4,5-dihydroisoxazole-3-carboxylic acid (0.36 g, 1.44 mmol) in chloroform (1.6 mL), 1-ethyl-3-(3-dimethylaminopropyl) carbodiimide hydrochloride (0.33 g, 1.72 mmol) and 1-hydroxybenzotriazole (0.02 g, 0.14 mmol) at room temperature, and the mixture was stirred at room temperature for 1 hour. Thereafter, 4.3 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.24 g of N-(tetrahydrofran-3-ylmethyl)-5-(3-phenoxypropyl)-4, 5-dihydroisoxazole-3-carboxamide (hereinafter, referred to as present amide compound (7)) of following formula:

(7)

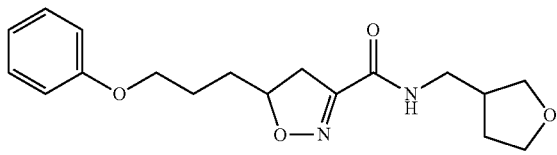

¹H-NMR (CDCl₃) δ: 7.31-7.27 (2H, m), 6.95 (1H, t, J=7.4 Hz), 6.89 (2H, dd, J=8.7, 1.0 Hz), 6.80-6.72 (1H, m, br), 4.91-4.82 (1H, m), 4.01 (2H, ddd, J=20.2, 9.2, 4.9 Hz), 3.90 (1H, td, J=8.3, 5.4 Hz), 3.84 (1H, dd, J=8.7, 6.9 Hz), 3.76 (1H, dd, J=15.3, 8.0 Hz), 3.55 (1H, dd, J=8.8, 5.4 Hz), 3.40-3.28 (3H, m), 2.93 (1H, dd, J=17.2, 8.4 Hz), 2.55-2.49 (1H, m), 2.11-2.02 (1H, m), 1.97-1.83 (4H, m), 1.66-1.56 (1H, m).

Production Example 8

Tetrahydrofuran-3-ylmethylamine hydrochloride (0.23 g, 1.64 mmol) was dissolved in 2.0 mL of chloroform (Amylene-added product), triethylamine (0.23 mL, 1.64 mmol) was added, and the mixture was stirred at room temperature for 30 minutes. To the mixed liquid were added a solution of 5-(4-phenoxybutyl)-4, 5-dihydroisoxazole-3-carboxylic acid (0.36 g, 1.37 mmol) in chloroform (1.4 mL), 1-ethyl-3-(3-dimethylaminopropyl)carbodiimide hydrochloride (0.31 g, 1.64 mmol) and 1-hydroxybenzotriazole (0.02 g, 0.14 mmol) at room temperature, and the mixture was stirred at room temperature for 1 hour. Thereafter, 4.1 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.14 g of N-(tetrahydrofuran-3-ylmethyl)-5-(4-phenoxybutyl)-4,5-dihydroisoxazole-3-carboxamide (hereinafter, referred to as present amide compound (8)) of following formula:

(8)

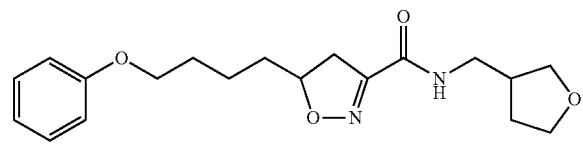

¹H-NMR (CDCl₃) δ: 7.32-7.24 (2H, m), 6.94 (1H, t, J=7.4 Hz), 6.89 (2H, dd, J=8.8, 0.9 Hz), 6.79-6.71 (1H, m, br), 4.84-4.76 (1H, m), 3.97 (2H, t, J=6.2 Hz), 3.90 (1H, td, J=8.3, 5.4 Hz), 3.84 (1H, dd, J=8.7, 6.9 Hz), 3.75 (1H, dd, J=15.3, 8.0 Hz), 3.55 (1H, dd, J=8.8, 5.4 Hz), 3.37 (2H, t, J=6.7 Hz), 3.30 (1H, dd, J=17.9, 10.9 Hz), 2.90 (1H, dd, J=17.7, 8.4 Hz), 2.55-2.48 (1H, m), 2.10-2.02 (1H, m), 1.87-1.77 (3H, m), 1.74-1.60 (4H, m).

Production Example 9

Tetrahydrofuran-3-ylmethylamine hydrochloride (0.24 g, 1.73 mmol) was dissolved in 3.6 mL of chloroform (Amylene-added product), triethylamine (0.24 mL, 1.73 mmol) was added, and the mixture was stirred at room temperature for 30 minutes. To the mixed liquid were added 5-(5-phenoxypentyl)-4,5-dihydroisoxazole-3-carboxylic acid (0.40 g, 1.44 mmol), 1-ethyl-3-(3-dimethylaminopropyl) carbodiimide hydrochloride (0.33 g, 1.73 mmol) and 1-hydroxybenzotriazole (0.02 g, 0.14 mmol) at room temperature, and the mixture was stirred at room temperature for 8 hours. Thereafter, 4.3 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.27 g of N-(tetrahydrofuran-3-ylmethyl)-5-(5-phenoxypentyl)-4, 5-dihydroisoxazole-3-carboxamide (hereinafter, referred to as present amide compound (9)) of following formula:

(9)

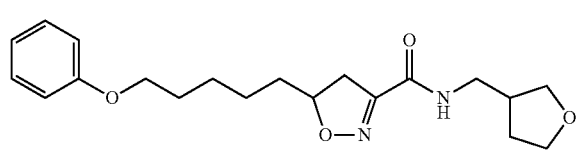

¹H-NMR (CDCl₃) δ: 7.33-7.27 (2H, m), 6.94 (1H, t, J=7.4 Hz), 6.89 (2H, dd, J=8.7, 1.0 Hz), 6.80-6.69 (1H, m, br), 4.85-4.72 (1H, m), 3.96 (2H, t, J=6.3 Hz), 3.90 (1H, td, J=8.2, 5.4 Hz), 3.84 (1H, dd, J=8.7, 6.9 Hz), 3.75 (1H, dd, J=15.5, 7.8 Hz), 3.55 (1H, dd, J=8.8, 5.2 Hz), 3.37 (2H, t, J=6.8 Hz), 3.28 (1H, dd, J=17.7, 10.9 Hz), 2.88 (1H, dd, J=17.7, 8.4 Hz), 2.55-2.48 (1H, m), 2.11-2.02 (1H, m), 1.85-1.71 (3H, m), 1.70-1.60 (2H, m), 1.56-1.41 (4H, m).

Production Example 10

Tetrahydrofuran-3-ylmethylamine hydrochloride (0.23 g, 1.65 mmol) was dissolved in 3.4 mL of chloroform (Amylene-added product), triethylamine 0.23 mL, 1.65 mmol) was added, and the mixture was stirred at room temperature for 30 minutes. To the mixed liquid were added 5-(6-phenoxyhexyl)-4,5-dihydroisoxazole-3-carboxylic acid (0.40 g, 1.37 mmol), 1-ethyl-3-(3-dimethylaminopropyl) carbodiimide hydrochloride (0.32 g, 1.65 mmol) and 1-hydroxybenzotriazole (0.02 g, 0.14 mmol) at room temperature, and the mixture was stirred at room temperature for 3 hours. Thereafter, 4.1 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.23 g of N-(tetrahydrofuran-3-ylmethyl)-5-(6-phenoxyhexyl)-4,5-dihydroisoxazole-3-carboxamide (hereinafter, referred to as present amide compound (10)) of following formula:

(10)

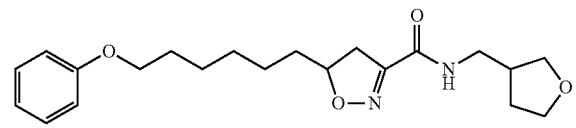

¹H-NMR (CDCl₃) δ: 7.31-7.24 (2H, m), 6.93 (1H, tt, J=7.4, 1.0 Hz), 6.90-6.88 (2H, m), 6.78-6.70 (1H, m, br), 4.81-4.73 (1H, m), 3.95 (2H, t, J=6.5 Hz), 3.89 (1H, td, J=8.3, 5.4 Hz), 3.84 (1H, dd, J=8.7, 6.9 Hz), 3.75 (1H, dd, J=15.2, 8.2 Hz), 3.55 (1H, dd, J=8.8, 5.4 Hz), 3.37 (2H, t, J=6.6 Hz), 3.28 (1H, ddd, J=17.8, 10.8, 0.6 Hz), 2.55-2.48 (1H, m), 2.10-2.02 (1H, m), 1.82-1.72 (4H, m), 1.68-1.62 (2H, m), 1.52-1.37 (6H, m).

Production Example 11

Tetrahydrofuran-3-ylmethylamine hydrochloride (0.33 g, 2.40 mmol) was added to chloroform (Amylene-added product) (5 mL). After to the mixed liquid were added 5-(benzyloxymethyl)-4,5-dihydroisoxazole-3-carboxylic acid (0.47 g, 2.00 mmol), 1-hydroxybenzotriazole (0.03 g, 0.24 mmol) and 1-ethyl-3-(3-dimethylaminopropyl)carbodiimide hydrochloride (0.46 g, 2.4 mmol) at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.19 g of N-(tetrahydrofuran-3-ylmethyl)-5-(benzyloxymethyl)-4,5-dihydroisoxazole-3-carboxamide (hereinafter, referred to as present amide compound (11)) of following formula:

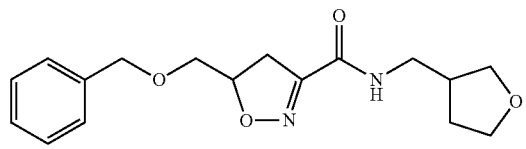

(11)

MS (ESI) m/z [M+H]⁺: 319.

Production Example 12

Tetrahydrofuran-3-ylmethylamine hydrochloride (0.25 g, 1.80 mmol) was dissolved in 1.8 mL of chloroform (Amylene-added product), triethylamine (0.25 mL, 1.80 mmol) was added, and the mixture was stirred at room temperature for 30 minutes. To the mixed liquid were added a solution of 5-(2-benzyloxyethyl)-4,5-dihydroisoxazole-3-carboxylic acid (0.38 g, 1.50 mmol) in chloroform (2.0 mL), 1-ethyl-3-(3-dimethylaminopropyl)carbodiimide hydrochloride (0.35 g, 1.80 mmol) and 1-hydroxybenzotriazole (0.02 g, 0.15 mmol) at room temperature, and the mixture was stirred at room temperature overnight. Thereafter, 5.6 ml of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.34 g of N-(tetrahydrofuran-3-ylmethyl)-5-(2-benzyloxyethyl)-4,5-dihydroisoxazole-3-carboxamide (hereinafter, referred to as present amide compound (12)) of following formula:

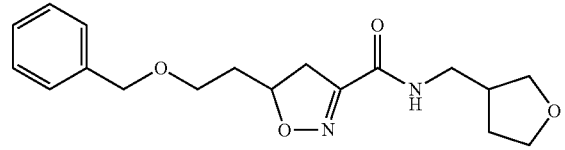

(12)

¹H-NMR (CDCl₃) δ: 7.38-7.28 (5H, m), 6.80-6.69 (1H, m, br), 5.00-4.92 (1H, m), 4.51 (2H, dd, J=15.0, 11.8 Hz), 3.89 (1H, td, J=8.2, 5.5 Hz), 3.83 (1H, dd, J=8.8, 7.0 Hz), 3.75 (1H, dd, J=15.5, 7.9 Hz), 3.61 (2H, dtd, J=16.4, 5.4, 3.1 Hz), 3.54 (1H, dd, J=8.7, 5.3 Hz), 3.36 (2H, t, J=6.8 Hz), 3.29 (1H, t, J=8.8 Hz), 2.96 (1H, dd, J=17.9, 8.2 Hz), 2.56-2.46 (1H, m), 2.10-1.99 (2H, m), 1.95-1.86 (1H, m), 1.69-1.64 (1H, m).

Production Example 13

Tetrahydrofuran-3-ylmethylamine hydrochloride (0.25 g, 1.82 mmol) was dissolved in 1.8 mL of chloroform (Amylene-added product), triethylamine (0.25 mL, 1.82 mmol) was added, and the mixture was stirred at room temperature for 30 minutes. To the mixed liquid were added a solution of 5-(3-benzyloxypropyl)-4,5-dihydroisoxazole-3-carboxylic acid (0.40 g, 1.52 mmol) in chloroform (2.0 mL), 1-ethyl-3-(3-dimethylaminopropyl)carbodiimide hydrochloride (0.35 g, 1.82 mmol) and 1-hydroxybenzotriazole (0.03 g, 0.15 mmol) at room temperature, and the mixture was stirred at room temperature overnight. Thereafter, 4.6 ml of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.32 g of N-(tetrahydrofuran-3-ylmethyl)-5-(3-benzyloxypropyl)-4,5-dihydroisoxazole-3-carboxamide (hereinafter, referred to as present amide compound (13)) of following formula:

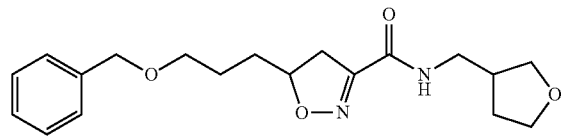

(13)

¹H-NMR (CDCl₃) δ: 7.37-7.29 (5H, m), 6.82-6.68 (1H, m, br), 4.85-4.73 (1H, m), 4.50 (2H, s), 3.89 (1H, td, J=8.1, 5.5 Hz), 3.83 (1H, dd, J=8.6, 7.0 Hz), 3.75 (1H, q, J=7.8 Hz), 3.56-3.48 (3H, m), 3.36 (2H, t, J=6.6 Hz), 3.28 (1H, dd, J=17.9, 10.8 Hz), 2.89 (1H, dd, J=17.6, 8.2 Hz), 2.56-2.46 (1H, m), 2.11-2.01 (1H, m), 1.87-1.63 (5H, m).

Production Example 14

Tetrahydrofuran-3-ylmethylamine hydrochloride (0.23 g, 1.69 mmol) was dissolved in 1.5 mL of chloroform (Amylene-added product), triethylamine (0.24 mL, 1.69 mmol) was added, and the mixture was stirred at room temperature for 30 minutes. To the mixed liquid were added a solution of 5-(4-benzyloxybutyl)-4,5-dihydroisoxazole-3-carboxylic acid (0.39 g, 1.41 mmol) in chloroform (2.0 mL), 1-ethyl-3-(3-dimethylaminopropyl)carbodiimide hydrochloride (0.32 g, 1.69 mmol) and 1-hydroxybenzotriazole (0.02 g, 0.14 mmol) at room temperature, and the mixture was stirred at room temperature for 1 hour. Thereafter, 4.2 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.32 g of N-(tetrahydrofuran-3-ylmethyl)-5-(4-benzyloxybutyl)-4,5-dihydroisoxazole-3-carboxamide (hereinafter, referred to as present amide compound (14)) of following formula:

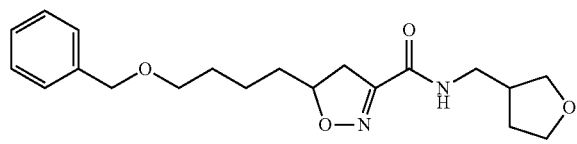

(14)

$^1$H-NMR (CDCl$_3$) δ: 7.38-7.27 (5H, m), 6.80-6.70 (1H, m, br), 4.80-4.72 (1H, m), 4.50 (2H, s), 3.89 (1H, td, J=8.3, 5.4 Hz), 3.83 (1H, dd, J=8.7, 6.9 Hz), 3.75 (1H, dd, J=15.5, 7.7 Hz), 3.54 (1H, dd, J=8.7, 5.3 Hz), 3.48 (2H, t, J=6.3 Hz), 3.36 (2H, t, J=6.8 Hz), 3.27 (1H, dd, J=17.6, 10.8 Hz), 2.87 (1H, dd, J=17.9, 8.5 Hz), 2.56-2.46 (1H, m), 2.10-2.02 (1H, m), 1.83-1.70 (1H, m), 1.70-1.42 (6H, m).

Production Example 15

Tetrahydrofuran-3-ylmethylamine hydrochloride (0.19 g, 1.38 mmol) was dissolved in 1.0 mL of chloroform (Amylene-added product), triethylamine (0.19 mL, 1.38 mmol) was added, and the mixture was stirred at room temperature for 30 minutes. To the mixed liquid were added a solution of 5-(5-benzyloxypentyl)-4,5-dihydroisoxazole-3-carboxylic acid (0.35 g, 1.19 mmol) in chloroform (2.0 mL), 1-ethyl-3-(3-dimethylaminopropyl)carbodiimide hydrochloride (0.26 g, 1.38 mmol) and 1-hydroxybenzotriazole (0.02 g, 0.12 mmol) at room temperature, and the mixture was stirred at room temperature overnight. Thereafter, 3.0 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.27 g of N-(tetrahydrofuran-3-ylmethyl)-5-(5-benzyloxypentyl)-4,5-dihydroisoxazole-3-carboxamide (hereinafter, referred to as present amide compound (15)) of following formula:

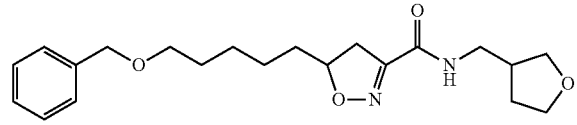

(15)

$^1$H-NMR (CDCl$_3$) δ: 7.39-7.28 (5H, m), 6.86-6.68 (1H, m, br), 4.80-4.72 (1H, m), 4.50 (2H, s), 3.89 (1H, td, J=8.1, 5.5 Hz), 3.83 (1H, dd, J=8.6, 7.0 Hz), 3.75 (1H, q, J=7.8 Hz), 3.55 (1H, dd, J=8.8, 5.4 Hz), 3.47 (2H, t, J=6.5 Hz), 3.37 (2H, t, J=6.6 Hz), 3.26 (1H, dd, J=17.4, 10.9 Hz), 2.86 (1H, dd, J=17.4, 8.4 Hz), 2.58-2.44 (1H, m), 2.10-2.02 (1H, m), 1.82-1.69 (1H, m), 1.69-1.53 (4H, m), 1.51-1.29 (4H, m).

Production Example 16

Tetrahydrofuran-3-ylmethylamine hydrochloride (0.17 g, 1.26 mmol) was dissolved in 1.0 mL of chloroform (Amylene-added product), triethylamine (0.17 mL, 1.26 mmol) was added, and the mixture was stirred at room temperature for 30 minutes. To the mixed liquid were added 5-(6-benzyloxyhexyl)-4,5-dihydroisoxazole-3-carboxylic acid (0.32 g, 1.06 mmol), 1-ethyl-3-(3-dimethylaminopropyl)carbodiimide hydrochloride (0.24 g, 1.26 mmol) and 1-hydroxybenzotriazole (0.01 g, 0.11 mmol) at room temperature, and the mixture was stirred at room temperature overnight. Thereafter, 2.7 mL of 1N hydrochloric acid was added to the reaction mixture, followed by extraction with chloroform. The organic layer was dried with anhydrous magnesium sulfate, and filtered, and the filtrate was concentrated under reduced pressure. The resulting residue was subjected to silica gel column chromatography to obtain 0.30 g of N-(tetrahydrofuran-3-ylmethyl)-5-(6-benzyloxyhexyl)-4,5-dihydroisoxazole-3-carboxamide (hereinafter, referred to as present amide compound (16)) of following formula:

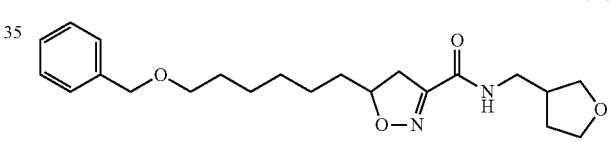

(16)

$^1$H-NMR (CDCl$_3$) δ: 7.38-7.28 (5H, m), 6.80-6.72 (1H, m, br), 4.80-4.71 (1H, m), 4.50 (2H, s), 3.89 (1H, td, J=8.3, 5.4 Hz), 3.83 (1H, dd, J=8.8, 7.0 Hz), 3.75 (1H, dd, J=15.5, 7.8 Hz), 3.54 (1H, dd, J=8.8, 5.2 Hz), 3.46 (2H, t, J=6.6 Hz), 3.37 (2H, q, J=6.9 Hz), 3.26 (1H, dd, J=17.7, 10.9 Hz), 2.86 (1H, dd, J=17.8, 8.5 Hz), 2.56-2.46 (1H, m), 2.10-2.02 (1H, m), 1.81-1.68 (1H, m), 1.67-1.56 (2H, m), 1.50-1.30 (8H, m).

Production Example 17

Tetrahydrofuran-3-ylmethylamine hydrochloride (0.25 g, 1.80 mmol) was dissolved in 1.7 mL of chloroform (Amylene-added product), triethylamine (0.25 mL, 1.80 mmol) was added, and the mixture was stirred at room temperature for 30 minutes. To the mixed liquid were added a solution of 5-phenethyloxymethyl-4,5-dihydroisoxazole-3-carboxylic acid (0.38 g, 1.50 mmol) in chloroform (3.7 mL), 1-ethyl-3-(3-dimethylaminopropyl)carbodiimide hydrochloride (0.34 g, 1.80 mmol) and 1-hydroxybenzotriazole (0.02 g, 0.15 mmol) at room temperature, and the mixture was stirred at room temperature overnight. Thereafter, 4.5 mL of 1N hydrochloric acid was added to the reaction mixture, followed by extraction with chloroform. The organic layer was washed with an aqueous saturated sodium bicarbonate solution, dried with anhydrous magnesium sulfate, and filtered, and the filtrate was concentrated under reduced pressure.

The resulting residue was subjected to silica gel column chromatography to obtain 0.37 g of N-(tetrahydrofuran-3-ylmethyl)-5-phenethyloxymethyl-4,5-dihydroisoxazole-3-carboxamide (hereinafter, referred to as present amide compound (17)) of following formula:

(17)

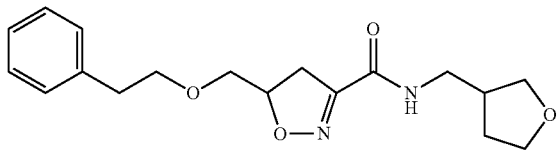

¹H-NMR (CDCl₃) δ: 7.32-7.27 (2H, m), 7.24-7.17 (3H, m), 6.82-6.70 (1H, m, br), 4.90 (1H, ddd, J=15.6, 8.1, 4.3 Hz), 3.89 (1H, td, J=8.2, 5.5 Hz), 3.83 (1H, dd, J=8.8, 7.0 Hz), 3.76 (1H, t, J=7.6 Hz), 3.73-3.66 (2H, m), 3.62-3.52 (3H, m), 3.43-3.31 (2H, m), 3.27-3.19 (1H, m), 3.13-3.06 (1H, m), 2.88 (2H, t, J=7.1 Hz), 2.57-2.47 (1H, m), 2.10-2.02 (1H, m), 1.67-1.59 (1H, m).

Production Example 18

Tetrahydrofuran-3-ylmethylamine hydrochloride (0.21 g, 1.51 mmol) was dissolved in 2.0 mL of chloroform (Amylene-added product), triethylamine (0.21 mL, 1.51 mmol) was added, and the mixture was stirred at room temperature for 30 minutes. To the mixed liquid were added a solution of 5-(3-phenethyloxypropy)-4,5-dihydroisoxazole-3-carboxylic acid (0.35 g, 1.26 mmol) in chloroform (1.0 mL), 1-ethyl-3-(3-dimethylaminopropyl)carbodiimide hydrochloride (0.29 g, 1.51 mmol) and 1-hydroxybenzotriazole (0.02 g, 0.13 mmol) at room temperature, and the mixture was stirred at room temperature overnight. Thereafter, 3.8 mL of 1N hydrochloric acid was added to the reaction mixture, followed by extraction with chloroform. The organic layer was dried with anhydrous magnesium sulfate, and filtered, and the filtrate was concentrated under reduced pressure. The resulting residue was subjected to silica gel column chromatography to obtain 0.13 g of N-(tetrahydrofuran-3-ylmethyl)-5-(3-phenethyloxypropyl)-4,5-dihydroisoxazole-3-carboxamide (hereinafter, referred to as present amide compound (18)) of following formula:

(18)

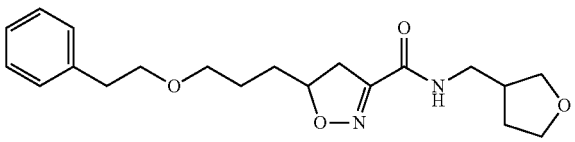

¹H-NMR (CDCl₃) δ: 7.32-7.27 (2H, m), 7.24-7.17 (3H, m), 6.79-6.70 (1H, m, br), 4.79-4.71 (1H, m), 3.90 (1H, td, J=8.3, 5.4 Hz), 3.84 (1H, dd, J=8.7, 6.9 Hz), 3.75 (1H, dd, J=15.2, 8.2 Hz), 3.63 (2H, t, J=7.1 Hz), 3.55 (1H, dd, J=8.8, 5.4 Hz), 3.47 (2H, ddd, J=12.3, 6.2, 3.2 Hz), 3.39-3.35 (2H, m), 3.25 (1H, dd, J=17.8, 10.8 Hz), 2.89-2.81 (3H, m), 2.57-2.46 (1H, m), 2.11-2.01 (1H, m), 1.80-1.57 (5H, m).

Production Example 19

Tetrahydrofuran-3-ylmethylamine hydrochloride (0.33 g, 2.40 mmol) was added to chloroform (Amylene-added product) (5 mL). After to the mixed liquid were added 5-(2-naphthyloxymethyl)-4,5-dihydroisoxazole-3-carboxylic acid (0.57 g, 2.00 mmol), 1-hydroxybenzotriazole (0.03 g, 0.24 mmol) and 1-ethyl-3-(3-dimethylaminopropyl)carbodiimide hydrochloride (0.46 g, 2.4 mmol) at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.49 g of N-(tetrahydrofuran-3-ylmethyl)-5-(2-naphthyloxymethyl)-4,5-dihydroisoxazole-3-carboxamide (hereinafter, referred to as present amide compound (19)) of following formula:

(19)

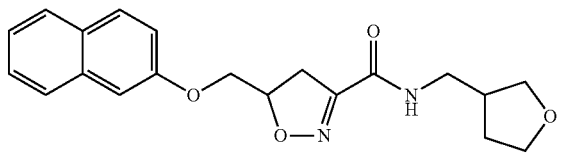

MS (ESI) m/z [M+H]⁺: 355.

Production Example 20

Tetrahydrofuran-3-ylmethylamine hydrochloride (0.33 g, 2.40 mmol) was added to chloroform (Amylene-added product) (5 mL). After to the mixed liquid were added 5-(2-naphthylmethyloxymethyl)-4,5-dihydroisoxazole-3-carboxylic acid (0.57 g, 2.00 mmol), 1-hydroxybenzotriazole (0.03 g, 0.24 mmol) and 1-ethyl-3-(3-dimethylaminopropyl)carbodiimide hydrochloride (0.46 g, 2.4 mmol) at room temperature, the mixture was stirred at room temperature for 5 hours. Dilute hydrochloric acid was added to the reaction mixture, followed by extraction with chloroform two times. The organic layer was washed with an aqueous saturated sodium bicarbonate solution, dried with anhydrous sodium sulfate, and filtered, and the filtrate was concentrated under reduced pressure. The residue was subjected to silica gel column chromatography to obtain 0.53 g of N-(tetrahydrofuran-3-ylmethyl)-5-(2-naphthylmethyloxymethyl)-4,5-dihydroisoxazole-3-carboxamide (hereinafter, referred to as present amide compound (20)) of following formula:

(20)

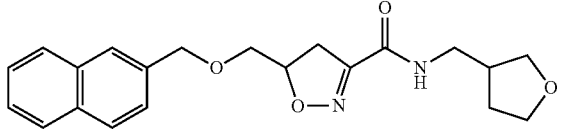

MS (ESI) m/z [M+H]⁺: 369.

Production Example 21

5-(2-Naphthylmethyloxypropyl)-4,5-dihydroisoxazole-3-carboxylic acid (0.57 g, 1.81 mmol) was added to chloroform (Amylene-added product) (4.5 mL). To the mixed liquid were added 1-hydroxybenzotriazole (0.02 g, 0.18 mmol), tetrahydrofuran-3-ylmethylamine hydrochloride (0.300 g, 2.17 mmol) and triethylamine (0.30 ml, 2.17 mmol) at room temperature, and the mixture was stirred at room temperature for 30 minutes. After to the mixed liquid was added 1-ethyl-3-(3-dimethylaminopropyl)carbodiimide hydrochloride (0.42 g, 2.17 mmol) at room temperature, the mixture was stirred at room temperature overnight. Dilute hydrochloric acid was added to the reaction mixture, followed by extraction with chloroform two times. The organic layer was washed with an aqueous saturated sodium bicarbonate solution and an aqueous saturated sodium chloride solution, dried with anhydrous magnesium sulfate, and filtered, and the filtrate was concentrated under reduced pressure. The resulting crystal was washed with isopropyl alcohol, and dried under reduced pressure to obtain 0.58 g of N-(tetrahydrofuran-3-ylmethyl)-5-(2-naphthylmethyloxypropyl)-4,5-dihydroisoxazole-3-carboxamide (hereinafter, referred to as present amide compound (21)) of following formula:

(21)

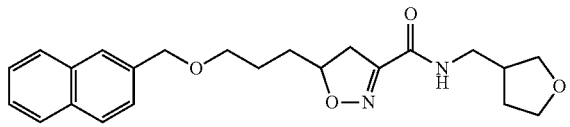

$^1$H-NMR (CDCl$_3$) δ: 7.87-7.80 (3H, m), 7.77 (1H, s), 7.50-7.43 (3H, m), 6.77-6.69 (1H, m), 4.86-4.76 (1H, m), 4.67 (2H, s), 3.89 (1H, td, J=8.3, 5.4 Hz), 3.83 (1H, dd, J=8.8, 7.0 Hz), 3.75 (1H, dd, J=15.5, 7.8 Hz), 3.60-3.50 (3H, m), 3.36 (2H, t, J=6.7 Hz), 3.28 (1H, dd, J=17.8, 10.8 Hz), 2.90 (1H, dd, J=17.9, 8.4 Hz), 2.56-2.46 (1H, m), 2.10-2.01 (1H, m), 1.86-1.69 (4H, m), 1.66-1.54 (1H, m).

Production Example 22

4-Methyl-5-phenoxymethyl-4,5-dihydroisoxazole-3-carboxylic acid (0.300 g, 1.23 mmol) was dissolved in 3.0 mL of chloroform (Amylene-added product), 1-hydroxybenzotriazole (0.02 g, 0.16 mmol) was added, and the mixture was stirred at room temperature for 15 minutes. To the mixed liquid were added tetrahydrofuran-3-ylmethylamine hydrochloride (0.20 g, 1.48 mmol) and triethylamine (0.21 mL, 1.48 mmol) at room temperature, and the mixture was stirred at room temperature for 30 minutes. To the mixed solution was added 1-ethyl-3-(3-dimethylaminopropyl)carbodiimide hydrochloride (0.28 g, 1.48 mmol), and the mixture was stirred at room temperature overnight. Thereafter, 1.5 ml of 1N hydrochloric acid was added to the reaction mixture, followed by extraction with chloroform. The organic layer was dried with anhydrous magnesium sulfate, and filtered, and the filtrate was concentrated under reduced pressure. The resulting residue was subjected to silica gel column chromatography to obtain 0.08 g of N-(tetrahydrofuran-3-ylmethyl)-4-methyl-5-phenoxymethyl-4,5-dihydroisoxazole-3-carboxamide (hereinafter, referred to as present amide compound (22)) of following formula:

(22)

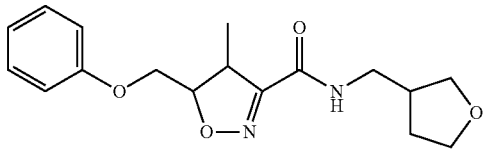

$^1$H-NMR (CDCl$_3$) δ: 7.29 (2H, dd, J=8.8, 7.4 Hz), 6.98 (1H, t, J=7.3 Hz), 6.89 (2H, dd, J=8.8, 1.0 Hz), 6.78-6.70 (1H, m, br), 4.67 (1H, dd, J=11.1, 5.2 Hz), 4.09 (1H, dd, J=10.2, 5.2 Hz), 4.02 (1H, dd, J=10.3, 5.0 Hz), 3.90 (1H, td, J=8.3, 5.3 Hz), 3.85 (1H, ddd, J=9.3, 6.5, 2.5 Hz), 3.76 (1H, q, J=8.0 Hz), 3.66-3.60 (1H, m), 3.55 (1H, dd, J=8.8, 5.4 Hz), 3.44-3.31 (2H, m), 2.56-2.49 (1H, m), 2.13-2.02 (1H, m), 1.69-1.59 (1H, m), 1.43 (3H, d, J=7.1 Hz).

Production Example 23

5-(5-Phenoxypentyl)-4,5-dihydroisoxazole-3-carboxylic acid (0.35 g, 1.26 mmol), 1-ethyl-3-(3-dimethylaminopropyl)carbodiimide hydrochloride (0.29 g, 1.51 mmol) and 1-hydroxybenzotriazole (0.02 g, 0.13 mmol) were dissolved in 3.0 mL of chloroform (Amylene-added product), isobutylamine (0.15 mL, 1.51 mmol) was added, and the mixture was stirred at room temperature overnight. Thereafter, 1N hydrochloric acid was added to the reaction mixture, and chloroform was added, followed by concentration under reduced pressure. The organic layer was extracted with ethyl acetate, washed with an aqueous saturated sodium bicarbonate solution, dried with anhydrous magnesium sulfate, and filtered, and the filtrate was concentrated under reduced pressure. The resulting residue was subjected to silica gel column chromatography to obtain 0.18 g of N-isobutyl-5-(5-phenoxypentyl)-4,5-dihydroisoxazole-3-carboxamide (hereinafter, referred to as present amide compound (23)) of following formula:

(23)

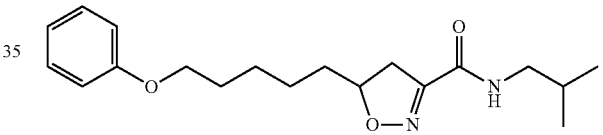

$^1$H-NMR (CDCl$_3$) δ: 7.28 (2H, dd, J=8.7, 7.4 Hz), 6.93 (1H, tt, J=7.4, 1.0 Hz), 6.89 (2H, ddd, J=8.9, 3.3, 2.3 Hz), 6.71-6.62 (1H, m, br), 4.81-4.73 (1H, m), 3.96 (2H, t, J=6.3 Hz), 3.29 (1H, dd, J=17.8, 10.8 Hz), 3.17 (2H, dd, J=6.8, 6.3 Hz), 2.89 (1H, dd, J=17.9, 8.4 Hz), 1.89-1.71 (5H, m), 1.71-1.39 (4H, m), 0.94 (6H, d, J=6.6 Hz).

Production Example 24

6-Phenoxymethyl-5,6-dihydro-4H-[1,2]oxazine-3-carboxylic acid (0.31 g, 1.33 mmol), tetrahydrofuran-3-ylmethylamine hydrochloride (0.22 g, 1.60 mmol), triethylamine (0.22 ml, 1.60 mmol) and 1-hydroxybenzotriazole (0.02 g, 0.1 mmol) were added to chloroform (Amylene-added product) (4.0 mL), and the mixture was stirred at room temperature for 30 minutes. To the mixture was added 1-ethyl-3-(3-dimethylaminopropyl)carbodiimide hydrochloride (0.02 g, 0.13 mmol) at room temperature, followed by stirring overnight. Thereafter, 1N hydrochloric acid was added to the reaction mixture, followed by extraction with ethyl acetate. The organic layer was dried with anhydrous magnesium sulfate, and filtered, and the filtrate was concentrated under reduced pressure. The resulting residue was subjected to silica gel column chromatography to obtain 0.12 g of N-(tetrahydrofuran-3-ylmethyl)-6-phenoxymethyl-5,6-dihydro-4H-[1,2]oxazine-3-carboxamide (hereinafter, referred to as present amide compound (24)) of following formula:

(24)

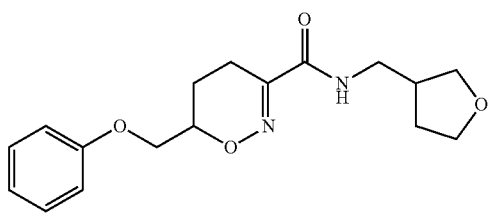

¹H-NMR (CDCl₃) δ: 7.33-7.28 (2H, m), 7.06-6.98 (1H, m, br), 6.99 (1H, t, J=7.4 Hz), 6.94 (2H, dd, J=8.8, 0.9 Hz), 4.23-4.09 (3H, m), 3.89 (1H, td, J=8.2, 5.5 Hz), 3.84 (1H, dd, J=8.8, 7.0 Hz), 3.75 (1H, dd, J=15.3, 8.0 Hz), 3.53 (1H, dd, J=8.8, 5.4 Hz), 3.41-3.29 (2H, m), 2.76 (1H, ddd, J=19.6, 6.2, 1.4 Hz), 2.53-2.39 (2H, m), 2.20-2.14 (1H, m), 2.10-2.01 (1H, m), 1.94-1.82 (1H, m), 1.64 (1H, dd, J=13.1, 7.5 Hz).

Production Example 25

Tetrahydrofuran-3-ylmethylamine hydrochloride (0.45 g, 3.24 mmol) was dissolved in 3.0 mL of chloroform (Amylene-added product), triethylamine (0.45 mL, 3.24 mmol) was added, and the mixture was stirred at room temperature for 30 minutes. To the mixed liquid were added 5.0 mL of a solution of 6-(3-chloro-phenoxymethyl)-5,6-dihydro-4H-[1,2]oxazine-3-carboxylic acid (0.96 g, 2.70 mmol) in chloroform (Amylene-added product), and 1-hydroxybenzotriazole (0.04 g, 0.270 mmol) at room temperature, and the mixture was stirred at room temperature for 30 minutes. To the mixed liquid was added 1-ethyl-3-(3-dimethylaminopropyl)carbodiimide hydrochloride (0.62 g, 3.24 mmol), followed by stirring overnight. Thereafter, 4.0 mL of 1N hydrochloric acid was added to the reaction mixture, followed by extraction with chloroform. The organic layer was washed with water, dried with anhydrous magnesium sulfate, and filtered, and the filtrate was concentrated under reduced pressure. The resulting residue was subjected to silica gel column chromatography to obtain 0.39 g of N-(tetrahydrofuran-3-ylmethyl)-6-(3-chloro-phenoxymethyl)-5,6-dihydro-4H-[1,2]oxazine-3-carboxamide (hereinafter, referred to as present amide compound (25)) of following formula:

(25)

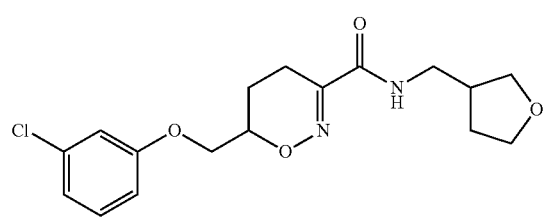

¹H-NMR (CDCl₃) δ: 7.22 (1H, t, J=8.2 Hz), 7.00-6.96 (2H, m), 6.93 (1H, t, J=2.3 Hz), 6.83 (1H, dt, J=8.4, 1.2 Hz), 4.19-4.11 (3H, m), 3.92-3.86 (1H, m), 3.84 (1H, dd, J=8.7, 7.1 Hz), 3.75 (1H, dd, J=15.5, 7.6 Hz), 3.53 (1H, dd, J=8.8, 5.4 Hz), 3.37-3.33 (2H, m), 2.77 (1H, dd, J=20.0, 5.3 Hz), 2.54-2.39 (2H, m), 2.17-2.11 (1H, m), 2.10-2.00 (1H, m), 1.93-1.81 (1H, m), 1.68-1.59 (1H, m).

Production Example 26

Tetrahydrofuran-3-ylmethylamine hydrochloride (0.04 g, 0.260 mmol) was dissolved in 0.2 mL of chloroform (Amylene-added product), triethylamine (0.04 mL, 0.260 mmol) was added, and the mixture was stirred at room temperature for 30 minutes. To the mixed liquid were added 1.0 mL of a solution of 6-benzyloxymethyl-5,6-dihydro-4H-[1,2]oxazine-3-carboxylic acid (0.05 g, 0.217 mmol) in chloroform (Amylene-added product), 1-ethyl-3-(3-dimethylaminopropyl)carbodiimide hydrochloride (0.05 g, 0.260 mmol) and 1-hydroxybenzotriazole (3.0 mg, 0.022 mmol) at room temperature, and the mixture was stirred overnight. Thereafter, 1N hydrochloric acid was added to the reaction mixture, followed by extraction with ethyl acetate. The organic layer was dried with anhydrous magnesium sulfate, and filtered, and the filtrate was concentrated under reduced pressure. The resulting residue was subjected to silica gel column chromatography to obtain 20.0 mg of N-(tetrahydrofuran-3-ylmethyl)-6-benzyloxymethyl-5,6-dihydro-4H-[1,2]oxazine-3-carboxamide (hereinafter, referred to as present amide compound (26)) of following formula:

(26)

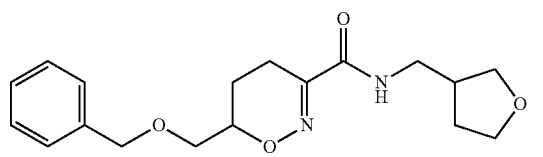

¹H-NMR (CDCl₃) δ: 7.39-7.28 (5H, m), 7.07-6.96 (1H, m, br), 4.61 (2H, s), 3.99-3.94 (1H, m), 3.88 (1H, td, J=8.2, 5.5 Hz), 3.83 (1H, dd, J=8.8, 7.0 Hz), 3.75 (1H, dd, J=15.2, 7.9 Hz), 3.71-3.63 (2H, m), 3.52 (1H, dd, J=8.8, 5.4 Hz), 3.39-3.28 (2H, m), 2.69 (1H, ddd, J=19.7, 6.1, 2.3 Hz), 2.54-2.44 (1H, m), 2.42-2.32 (1H, m), 2.08-2.00 (2H, m), 1.82-1.70 (1H, m), 1.62 (1H, td, J=13.0, 7.4 Hz).

Production Example 27

Oxalyl chloride (0.68 mL, 7.88 mmol) was added dropwise to 2-phenoxymethyl-3,4-dihydro-2H-pyran (1.0 g, 5.26 mmol) slowly under ice-cooling. After stirred at room temperature for 1 hour, the mixed liquid was concentrated under reduced pressure. The concentrated reaction mixture was stirred at 120 degree for 30 minutes, and cooled to room temperature. To the mixed liquid was added 4.0 mL of a solution of tetrahydrofuran-3-ylmethylamine hydrochloride (0.87 g, 6.31 mmol) and triethylamine (1.2 mL, 8.94 mmol) in chloroform (Amylene-added product), followed by stirring overnight. Thereafter, the reaction mixture was concentrated under reduced pressure, and the resulting residue was subjected to silica gel column chromatography to obtain 0.31 g of N-(tetrahydrofuran-3-ylmethyl)-6-phenoxymethyl-5,6-dihydro-4H-pyrane-3-carboxamide (hereinafter, referred to as present amide compound (27)) of following formula:

(27)

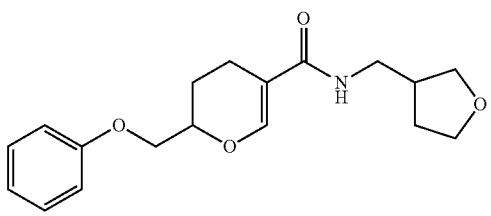

¹H-NMR (CDCl₃) δ: 7.47 (1H, s), 7.32-7.27 (2H, m), 6.98 (1H, t, J=7.3 Hz), 6.93 (2H, dd, J=8.8, 1.0 Hz), 5.70-5.56 (1H, m, br), 4.29-4.23 (1H, m), 4.17-4.11 (1H, m), 4.05 (1H, dd, J=10.0, 4.9 Hz), 3.90 (1H, td, J=8.3, 5.3 Hz), 3.81 (1H, dd, J=8.7, 6.9 Hz), 3.74 (1H, td, J=8.1, 7.1 Hz), 3.58 (1H, dd, J=8.8, 4.9 Hz), 3.41-3.29 (2H, m), 2.59-2.47 (1H, m), 2.36-2.28 (2H, m), 2.16-2.00 (2H, m), 1.91-1.81 (1H, m), 1.68-1.60 (1H, m).

Production Example 28

Oxalyl chloride (0.63 mL, 7.34 mmol) was added dropwise to 2-benzyloxymethyl-3,4-dihydro-2H-pyran (1.0 g, 4.90 mmol) slowly under ice-cooling. After stirred at room temperature for 1 hour, the mixed liquid was concentrated under reduced pressure. The concentrated reaction mixture was stirred at 120 degree for 30 minutes, and cooled to room temperature. To the mixed liquid was added 4.0 mL of a solution of tetrahydrofuran-3-ylmethylamine hydrochloride (0.81 g, 5.88 mmol) and triethylamine (1.1 mL, 8.33 mmol) in chloroform (Amylene-added product), followed by stirring overnight. Thereafter, the reaction mixture was concentrated under reduced pressure, and the resulting residue was subjected to silica gel column chromatography to obtain 0.31 g of N-(tetrahydrofuran-3-ylmethyl)-6-phenoxymethyl-5,6-dihydro-4H-pyran-3-carboxamide (hereinafter, referred to as present amide compound (28)) of following formula:

(28)

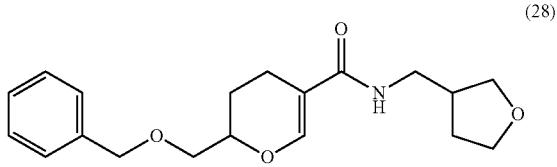 [SMILES: O=C(NCC1CCOC1)C1=COC(COCc2ccccc2)CC1]

¹H-NMR (CDCl₃) δ: 7.45 (1H, s), 7.38-7.28 (5H, m), 5.69-5.54 (1H, m, br), 4.59 (2H, dd, J=15.7, 12.1 Hz), 4.10-4.03 (1H, m), 3.89 (1H, td, J=8.3, 5.4 Hz), 3.80 (1H, dd, J=8.7, 6.9 Hz), 3.73 (1H, dd, J=15.3, 8.0 Hz), 3.63 (1H, dd, J=10.2, 5.9 Hz), 3.57 (2H, dd, J=10.2, 4.5 Hz), 3.42-3.24 (2H, m), 2.57-2.47 (1H, m), 2.27-2.24 (2H, m), 2.10-1.92 (2H, m), 1.80-1.70 (1H, m), 1.70-1.55 (1H, m).

Then, Production Examples of intermediate compounds are shown as Reference Production Examples. Herein, Et represents an ethyl group.

Reference Production Example 1

Ethyl 2-chloro-2-(hydroxyimino)acetate (4.54 g, 30 mmol) and 1-hexene (2.10 g, 25 mmol) were added to N,N-dimethylformamide (50 mL). After to the mixed liquid was added triethylamine (3.03 g, 30 mmol) at room temperature, the mixture was stirred at room temperature overnight. Thereafter, dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The reaction mixture was added to ethanol (12 mL), potassium hydroxide (3.37 g, 60 mmol) and water (6 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 0.98 g of 5-butyl-4,5-dihydroisoxazole-3-carboxylic acid of following formula:

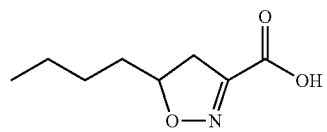

MS (ESI) m/z [M+H]⁺: 172.

Reference Production Example 2

Ethyl 5-pentyl-4,5-dihydroisoxazole-3-carboxylate (7.47 g, 35.0 mmol) was added to ethanol (140 mL), potassium hydroxide (3.93 g, 70.0 mmol) and water (70 mL) were added, and the mixture was stirred at room temperature for 2 hours. Thereafter, 42 mL of 2N hydrochloric acid was added to the reaction mixture, followed by extraction with ethyl acetate. The organic layer was washed with water, dried with anhydrous magnesium sulfate, and filtered, and the filtrate was concentrated under reduced pressure to obtain 6.15 g of 5-pentyl-4,5-dihydroisoxazole-3-carboxylic acid of following formula:

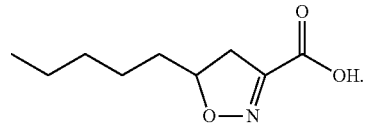

This was subjected to a next reaction without purification.
¹H-NMR (CDCl₃) δ: 6.24-5.64 (1H, m, br), 4.95-4.81 (1H, m), 3.26 (1H, dd, J=17.6, 11.0 Hz), 2.85 (1H, dd, J=17.6, 8.7 Hz), 1.84-1.73 (1H, m), 1.68-1.56 (1H, m), 1.50-1.22 (6H, m), 0.90 (3H, t, J=6.6 Hz).

Reference Production Example 3

1-Heptene (17.0 g, 201 mmol) and ethyl 2-chloro-2-(hydroxyimino)acetate (7.6 g, 50.0 mmol) were dissolved in dimethylformamide (100 mL), and the solution was ice-cooled to 15 degree or lower. A solution of triethylamine (7.7 mL, 55.0 mmol) in dimethylformamide (100 mL) was added dropwise to the mixed liquid over 30 minutes. After stirred at room temperature overnight, water was added to the reaction mixture, followed by extraction with methyl tertiary-butyl ether. The organic layer was washed with water, dried with anhydrous magnesium sulfate, and filtered, and the filtrate was concentrated under reduced pressure. The resulting residue was subjected to silica gel column chromatography to obtain 7.47 g of ethyl 5-pentyl-4,5-dihydroisoxazole-3-carboxylate of following formula:

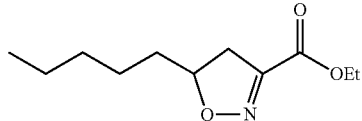

$^1$H-NMR (CDCl$_3$) δ: 4.84-4.75 (1H, m), 4.34 (2H, ddd, J=14.3, 7.1, 2.2 Hz), 3.25 (1H, ddd, J=17.4, 10.9, 1.8 Hz), 2.84 (1H, ddd, J=17.5, 8.6, 2.0 Hz), 1.79-1.72 (1H, m), 1.37 (3H, td, J=7.1, 2.1 Hz), 1.32-1.22 (7H, m), 0.91-0.88 (3H, m).

Reference Production Example 4

Ethyl 5-benzyl-4,5-dihydroisoxazole-3-carboxylate (1.28 g, 5.5 mmol) was added to ethanol (20 mL), potassium hydroxide (0.61 g, 11 mmol) and water (10 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 0.98 g of 5-propyl-4,5-dihydroisoxazole-3-carboxylic acid of following formula:

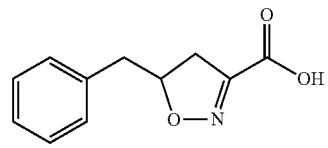 [SMILES: O=C(O)C1=NOC(Cc2ccccc2)C1]

MS (ESI) m/z [M+H]$^+$: 206.

Reference Production Example 5

Ethyl nitroacetate (1.49 g, 12.5 mmol), 3-phenyl-1-propene (1.18 g, 10 mmol) and 1,4-diazabicyclo[2.2.2]octane (0.22 g, 2 mmol) were added to chloroform (Amylene-added product) (3 mL). The mixed liquid was heated to reflux for 24 hours. Thereafter, the resultant was cooled to room temperature, and dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 1.28 g of ethyl 5-benzyl-4,5-dihydroisoxazole-3-carboxylate of following formula:

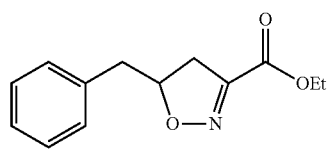 [SMILES: CCOC(=O)C1=NOC(Cc2ccccc2)C1]

MS (ESI) m/z [M+H]$^+$: 234.

Reference Production Example 6

Ethyl 5-phenethyl-4,5-dihydroisoxazole-3-carboxylate (7.46 g, 30.2 mmol) was added to ethanol (120 mL), potassium hydroxide (3.4 g, 60.4 mmol) and water (60 mL) were added, and the mixture was stirred at room temperature for 1.5 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 6.01 g of 5-phenethyl-4,5-dihydroisoxazole-3-carboxylic acid of following formula:

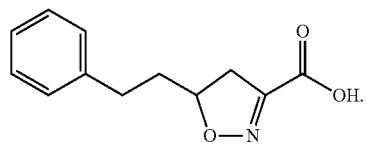

This was subjected to a next reaction without purification.

$^1$H-NMR (CDCl$_3$) δ: 7.33-7.28 (2H, m), 7.25-7.17 (3H, m), 4.91-4.83 (1H, m), 3.27 (1H, dd, J=17.7, 11.1 Hz), 2.86 (1H, dd, J=17.7, 8.4 Hz), 2.81-2.69 (2H, m), 2.19-2.07 (1H, m), 2.00-1.88 (1H, m).

Reference Production Example 7

Ethyl nitroacetate (6.21 mL, 56.0 mmol), 4-phenyl-1-butene (4.93 g, 37.3 mmol) and 1,4-diazabicyclo[2.2.2]octane (836 mg, 7.46 mmol) were added to chloroform (Amylene-added product) (12 mL), and the mixture was stirred at 90 degree for 2 hours. Thereafter, the resultant was stirred at 100 degree for 2 hours, and cooled to room temperature, and the reaction liquid was concentrated under reduced pressure. The resulting residue was subjected to silica gel column chromatography to obtain 7.41 g of ethyl 5-phenethyl-4,5-dihydroisoxazole-3-carboxylate of following formula:

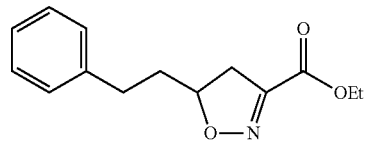 [SMILES: O=C(O)C1=NOC(CCc2ccccc2)C1]

$^1$H-NMR (CDCl$_3$) δ: 7.33-7.27 (2H, m), 7.24-7.17 (3H, m), 4.84-4.76 (1H, m), 4.35 (2H, q, J=7.1 Hz), 3.26 (1H, dd, J=17.6, 11.0 Hz), 2.86 (1H, dd, J=17.7, 8.4 Hz), 2.80-2.69 (2H, m), 2.14-2.06 (1H, m), 1.96-1.86 (1H, m), 1.37 (3H, t, J=7.1 Hz).

Reference Production Example 8

Ethyl 5-(phenoxymethyl)-4,5-dihydroisoxazole-3-carboxylate (2.49 g, 10 mmol) was added to ethanol (20 mL), potassium hydroxide (1.12 g, 20 mmol) and water (10 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 2.00 g of 5-(phenoxymethyl)-4,5-dihydroisoxazole-3-carboxylic acid of following formula:

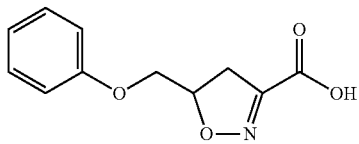 [SMILES: O=C(O)C1=NOC(COc2ccccc2)C1]

MS (ESI) m/z [M+H]$^+$: 222.

Reference Production Example 9

Ethyl nitroacetate (3.76 g, 25.3 mmol), 3-phenoxy-1-propene (3.39 g, 25.3 mmol) and 1,4-diazabicyclo[2.2.2]octane (0.57 g, 5.1 mmol) were added to chloroform (Amylene-added product) (7 mL). The mixed liquid was heated to reflux for 24 hours. Thereafter, the resultant was cooled to room temperature, and dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 2.50 g of ethyl 5-(phenoxymethyl)-4,5-dihydroisoxazole-3-carboxylate of following formula:

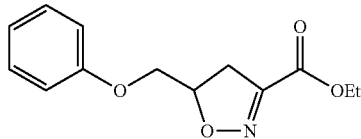 [SMILES: CCOC(=O)C1=NOC(COc2ccccc2)C1]

MS (ESI) m/z [M+H]$^+$: 250.

Reference Production Example 10

Ethyl 5-(2-phenoxyethyl)-4,5-dihydroisoxazole-3-carboxylate (520 mg, 1.98 mmol) was added to ethanol (8.0 mL), potassium hydroxide (224 mg, 3.96 mmol) and water (4.0 mL) were added, and the mixture was stirred at room temperature for 2.5 hours. Thereafter, 2N hydrochloric acid was added to the reaction mixture, followed by extraction with ethyl acetate. The organic layer was washed with an aqueous sodium chloride solution, dried with anhydrous magnesium sulfate, and filtered, and the filtrate was concentrated under reduced pressure to obtain 440 mg of 5-(2-phenoxyethyl)-4, 5-dihydroisoxazole-3-carboxylic acid of following formula:

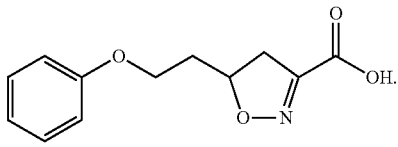 [SMILES: O=C(O)C1=NOC(CCOc2ccccc2)C1]

This was subjected to a next reaction without purification.
$^1$H-NMR (CDCl$_3$) δ: 7.30 (2H, dd, J=8.7, 7.4 Hz), 6.97 (1H, tt, J=7.4, 1.0 Hz), 6.90 (2H, dq, J=8.4, 1.5 Hz), 5.21-5.13 (1H, m), 4.19-4.06 (2H, m), 3.38 (1H, dd, J=17.7, 11.1 Hz), 3.06 (1H, dd, J=17.7, 8.2 Hz), 2.28-2.08 (2H, m).

Reference Production Example 11

Ethyl nitroacetate (350 μL, 3.16 mmol), 4-phenoxy-1-butene (376 mg, 2.53 mmol) and 1,4-diazabicyclo[2.2.2]octane (57 mg, 0.506 mmol) were added to chloroform (Amylene-added product) (780 μL), and the mixture was stirred at 60 degree for 1 hour. Thereafter, the resultant was stirred at 90 degree for 1 hour, and cooled to room temperature, and the reaction liquid was concentrated under reduced pressure. The resulting residue was subjected to silica gel column chromatography to obtain 541 mg of ethyl 5-(2-phenoxyethyl)-4,5-dihydroisoxazole-3-carboxylate of following formula:

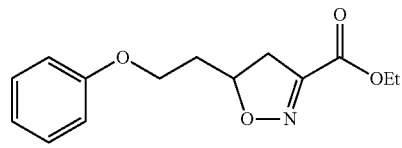 [SMILES: CCOC(=O)C1=NOC(CCOc2ccccc2)C1]

$^1$H-NMR (CDCl$_3$) δ: 7.29 (2H, tt, J=7.0, 2.2 Hz), 6.96 (1H, t, J=7.4 Hz), 6.89 (2H, dd, J=8.6, 0.9 Hz), 5.12-5.04 (1H, m), 4.34 (2H, q, J=7.1 Hz), 4.17-4.02 (2H, m), 3.36 (1H, dd, J=17.7, 11.1 Hz), 3.04 (1H, dd, J=17.7, 7.9 Hz), 2.25-2.03 (2H, m), 1.36 (3H, t, J=7.1 Hz).

Reference Production Example 12

Ethyl 5-(3-phenoxypropyl)-4,5-dihydroisoxazole-3-carboxylate (400 mg, 1.44 mmol) was added to ethanol (5.8 mL), potassium hydroxide (162 mg, 2.88 mmol) and water (2.9 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 350 mg of 5-(3-phenoxypropyl)-4,5-dihydroisoxazole-3-carboxylic acid of following formula:

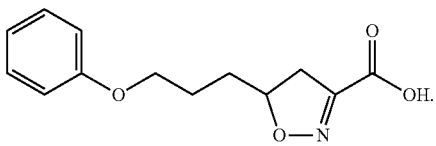

This was subjected to a next reaction without purification.
$^1$H-NMR (CDCl$_3$) δ: 7.29 (2H, td, J=7.0, 1.8 Hz), 6.95 (1H, t, J=7.3 Hz), 6.92-6.85 (2H, m), 5.05-4.94 (1H, m), 4.07-3.96 (2H, m), 3.33 (1H, dd, J=17.6, 11.0 Hz), 2.91 (1H, dd, J=17.6, 8.5 Hz), 2.03-1.84 (4H, m).

Reference Production Example 13

Ethyl nitroacetate (880 μL, 7.93 mmol), 5-phenoxy-1-pentene (1.03 g, 6.34 mmol) and 1,4-diazabicyclo[2.2.2]octane (142 mg, 1.27 mmol) were added to chloroform (Amylene-added product) (2.1 mL), and the mixture was stirred at 90 degree for 4 hours. Thereafter, ethyl nitroacetate (440 μL, 3.97 mmol) and 1,4-diazabicyclo[2.2.2]octane (142 mg, 1.27 mmol) were added, the mixture was stirred at 90 degree for 1 hour, and cooled to room temperature, and the reaction liquid was concentrated under reduced pressure. The resulting residue was subjected to silica gel column chromatography to obtain 1.34 g of ethyl 5-(3-phenoxypropyl)-4,5-dihydroisoxazole-3-carboxylate of following formula:

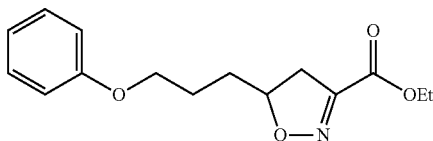 [SMILES: CCOC(=O)C1=NOC(CCCOc2ccccc2)C1]

¹H-NMR (CDCl₃) δ: 7.32-7.27 (2H, m), 6.97-6.93 (1H, m), 6.89 (2H, dd, J=8.7, 1.0 Hz), 4.95-4.84 (1H, m), 4.35 (2H, q, J=7.1 Hz), 4.05-3.96 (2H, m), 3.31 (1H, dd, J=17.6, 11.0 Hz), 2.90 (1H, dd, J=17.6, 8.3 Hz), 1.99-1.81 (4H, m), 1.37 (3H, t, J=7.1 Hz).

Reference Production Example 14

Ethyl 5-(4-phenoxybutyl)-4,5-dihydroisoxazole-3-carboxylate (400 mg, 1.37 mmol) was added to ethanol (5.5 mL), potassium hydroxide (154 mg, 2.75 mmol) and water (2.7 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 350 mg of 5-(4-phenoxybutyl)-4, 5-dihydroisoxazole-3-carboxylic acid of following formula:

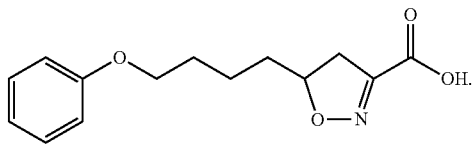 [SMILES: O=C(O)C1=NOC(CCCCOc2ccccc2)C1]

This was subjected to a next reaction without purification.
¹H-NMR (CDCl₃) δ: 7.29 (2H, d, J=8.5 Hz), 6.94 (1H, t, J=7.3 Hz), 6.89 (2H, d, J=8.2 Hz), 4.96-4.88 (1H, m), 3.98 (2H, t, J=6.2 Hz), 3.29 (1H, dd, J=17.6, 11.0 Hz), 2.88 (1H, dd, J=17.6, 8.7 Hz), 1.91-1.81 (3H, m), 1.77-1.52 (3H, m).

Reference Production Example 15

Ethyl nitroacetate (1.3 mL, 11.3 mmol), 6-phenoxy-1-hexene (1.33 g, 7.55 mmol) and 1,4-diazabicyclo[2.2.2]octane (169 mg, 1.51 mmol) were added to chloroform (Amylene-added product) (2.5 mL), and the mixture was stirred at 90 degree for 2.5 hours. Thereafter, after cooled to room temperature, the reaction liquid was concentrated under reduced pressure. The resulting residue was subjected to silica gel column chromatography to obtain 1.95 g of ethyl 5-(4-phenoxybutyl)-4,5-dihydroisoxazole-3-carboxylate of following formula:

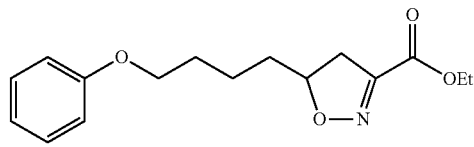 [SMILES: CCOC(=O)C1=NOC(CCCCOc2ccccc2)C1]

¹H-NMR (CDCl₃) δ: 7.31-7.25 (2H, m), 6.94 (1H, tt, J=7.2, 1.0 Hz), 6.89 (2H, dq, J=8.7, 1.7 Hz), 4.90-4.79 (1H, m), 4.35 (2H, q, J=7.1 Hz), 3.97 (2H, t, J=6.2 Hz), 3.27 (1H, dd, J=17.6, 11.0 Hz), 2.87 (1H, dd, J=17.7, 8.4 Hz), 1.94-1.79 (3H, m), 1.74-1.47 (3H, m), 1.37 (3H, t, J=7.1 Hz).

Reference Production Example 16

Ethyl 5-(5-phenoxypentyl)-4,5-dihydroisoxazole-3-carboxylate (1.97 g, 6.45 mmol) was added to ethanol (25 mL), potassium hydroxide (723 mg, 12.9 mmol) and water (13 mL) were added, and the mixture was stirred at room temperature for 3.5 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 1.28 g of 5-(5-phenoxypentyl)-4,5-dihydroisoxazole-3-carboxylic acid of following formula:

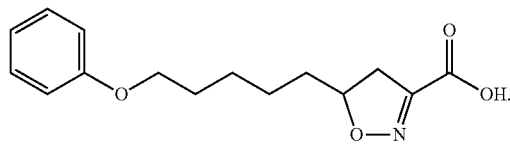 [SMILES: O=C(O)C1=NOC(CCCCCOc2ccccc2)C1]

This was subjected to a next reaction without purification.
¹H-NMR (CDCl₃) δ: 7.31-7.27 (2H, m), 6.94 (1H, t, J=7.4 Hz), 6.89 (2H, dd, J=8.7, 0.8 Hz), 4.94-4.86 (1H, m), 3.96 (2H, t, J=6.3 Hz), 3.28 (1H, dd, J=17.7, 11.1 Hz), 2.86 (1H, dd, J=17.7, 8.6 Hz), 1.88-1.74 (3H, m), 1.75-1.61 (1H, m), 1.61-1.42 (4H, m).

Reference Production Example 17

Ethyl nitroacetate (1.2 mL, 10.9 mmol), 7-phenoxy-1-heptene (1.38 g, 7.25 mmol) and 1,4-diazabicyclo[2.2.2]octane (162 mg, 1.45 mmol) were added to chloroform (Amylene-added product) (2.4 mL), and the mixture was stirred at 90 degree for 2.5 hours. Thereafter, ethyl nitroacetate (0.4 mL, 3.63 mmol) and 1,4-diazabicyclo[2.2.2]octane (162 mg, 1.45 mmol) were added, the mixture was stirred at 90 degree for 1 hour, and cooled to room temperature, and the reaction liquid was concentrated under reduced pressure. The resulting residue was subjected to silica gel column chromatography to obtain 1.97 g of ethyl 5-(5-phenoxypentyl)-4,5-dihydroisoxazole-3-carboxylate of following formula:

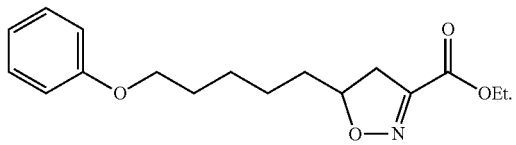 [SMILES: CCOC(=O)C1=NOC(CCCCCOc2ccccc2)C1]

¹H-NMR (CDCl₃) δ: 7.31-7.25 (2H, m), 6.94 (1H, tt, J=7.4, 1.0 Hz), 6.89 (2H, ddd, J=8.8, 3.3, 2.3 Hz), 4.86-4.78 (1H, m), 4.35 (2H, q, J=7.1 Hz), 3.96 (2H, t, J=6.3 Hz), 3.26 (1H, dd, J=17.6, 11.0 Hz), 2.85 (1H, dd, J=17.4, 8.4 Hz), 1.87-1.75 (3H, m), 1.70-1.60 (1H, m), 1.56-1.41 (4H, m), 1.37 (3H, t, J=7.1 Hz).

Reference Production Example 18

Ethyl 5-(6-phenoxyhexyl)-4,5-dihydroisoxazole-3-carboxylate (769 mg, 2.41 mmol) was added to ethanol (9.6 mL), potassium hydroxide (270 mg, 4.82 mmol) and water (2.9 mL) were added, and the mixture was stirred at room temperature for 9 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 632 mg of 5-(6-phenoxyhexyl)-4,5-dihydroisoxazole-3-carboxylic acid of following formula:

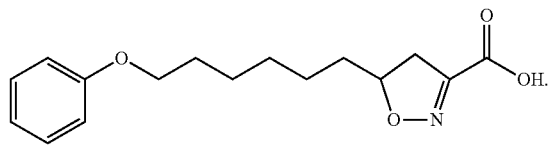 [SMILES: O=C(O)C1=NOC(CCCCCCOc2ccccc2)C1]

This was subjected to a next reaction without purification.
¹H-NMR (CDCl₃) δ: 7.31-7.25 (2H, m), 6.93 (1H, tt, J=7.3, 1.0 Hz), 6.89 (2H, ddd, J=9.0, 3.3, 2.2 Hz), 4.93-4.85 (1H, m), 3.96 (2H, t, J=6.4 Hz), 3.27 (1H, dd, J=17.6, 11.0 Hz), 2.86 (1H, dd, J=17.6, 8.7 Hz), 1.82-1.76 (3H, m), 1.71-1.59 (1H, m), 1.54-1.36 (7H, m).

Reference Production Example 19

Ethyl nitroacetate (512 μL, 4.62 mmol), 8-phenoxy-1-octene (630 mg, 3.08 mmol) and 1,4-diazabicyclo[2.2.2]octane (69 mg, 0.616 mmol) were added to chloroform (Amylene-added product) (1 mL), and the mixture was stirred at 90 degree for 2 hours. Thereafter, ethyl nitroacetate (400 μL, 3.60 mmol) and 1,4-diazabicyclo[2.2.2]octane (69 mg, 0.616 mmol) were added, and the mixture was stirred at 90 degree for 2 hours. Thereafter, the reaction liquid was cooled to room temperature, and concentrated under reduced pressure. The resulting residue was subjected to silica gel column chromatography to obtain 769 mg of ethyl 5-(6-phenoxyhexyl)-4,5-dihydroisoxazole-3-carboxylate of following formula:

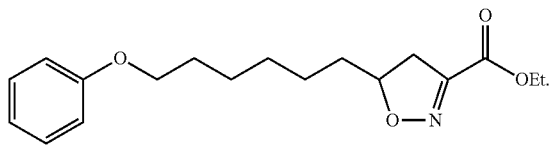 [SMILES: CCOC(=O)C1=NOC(CCCCCCOc2ccccc2)C1]

¹H-NMR (CDCl₃) δ: 7.31-7.25 (2H, m), 6.96-6.91 (1H, m), 6.91-6.87 (2H, m), 4.85-4.76 (1H, m), 4.35 (2H, q, J=7.2 Hz), 3.95 (2H, t, J=6.5 Hz), 3.25 (1H, dd, J=17.4, 10.9 Hz), 2.84 (1H, dd, J=17.4, 8.6 Hz), 1.84-1.73 (3H, m), 1.67-1.59 (1H, m), 1.50-1.41 (6H, m), 1.37 (3H, t, J=7.1 Hz).

Reference Production Example 20

Ethyl 5-(benzyloxymethyl)-4,5-dihydroisoxazole-3-carboxylate (3.45 g, 13.1 mmol) was added to ethanol (20 mL), potassium hydroxide (1.47 g, 26.2 mmol) and water (10 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 1.93 g of 5-(benzyloxymethyl)-4,5-dihydroisoxazole-3-carboxylic acid of following formula:

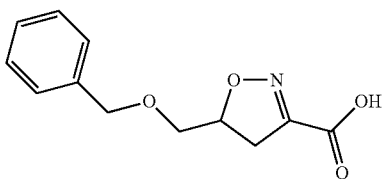 [SMILES: O=C(O)C1=NOC(COCc2ccccc2)C1]

MS (ESI) m/z [M+H]⁺: 236.

Reference Production Example 21

Ethyl 2-chloro-2-(hydroxyimino)acetate (3.57 g, 23.6 mmol), and 3-(benzyloxy)-1-propene (12.3 g, 82 mmol) were added to N,N-dimethylformamide (80 mL). Triethylamine (2.38 g, 23.6 mmol) was added to the mixed liquid at room temperature, and the mixture was stirred at room temperature overnight. Thereafter, dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 3.45 g of ethyl 5-(benzyloxymethyl)-4,5-dihydroisoxazole-3-carboxylate of following formula:

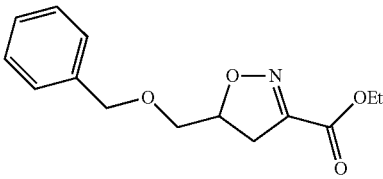 [SMILES: CCOC(=O)C1=NOC(COCc2ccccc2)C1]

MS (ESI) m/z [M+H]⁺: 264.

Reference Production Example 22

Ethyl 5-(2-benzyloxyethyl)-4,5-dihydroisoxazole-3-carboxylate (1.10 g, 4.97 mmol) was added to ethanol (16 mL), potassium hydroxide (445 mg, 7.94 mmol) and water (8 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 1.05 g of 5-(2-benzyloxyethyl)-4,5-dihydroisoxazole-3-carboxylic acid of following formula:

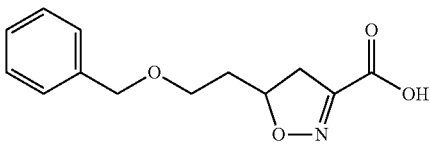 [SMILES: O=C(O)C1=NOC(CCOCc2ccccc2)C1]

This was subjected to a next reaction without purification.
¹H-NMR (CDCl₃) δ: 7.39-7.27 (5H, m), 5.11-5.01 (1H, m), 4.51 (2H, dd, J=16.3, 11.9 Hz), 3.69-3.53 (2H, m), 3.28 (1H, dd, J=17.6, 11.0 Hz), 2.96 (1H, dd, J=17.6, 8.2 Hz), 2.11-2.02 (1H, m), 2.00-1.89 (1H, m).

Reference Production Example 23

Ethyl nitroacetate (923 μL, 8.25 mmol), 4-benzyloxy-1-butene (892 mg, 5.50 mmol) and 1,4-diazabicyclo[2.2.2]octane (123 mg, 1.10 mmol) were added to chloroform (Amylene-added product) (1.8 mL), and the mixture was stirred at 90 degree for 2.5 hours. Thereafter, the mixture was stirred at 110 degree for 1 hour, and the reaction liquid was cooled to room temperature, and concentrated under reduced pressure. The resulting residue was subjected to silica gel column chromatography to obtain 1.10 g of ethyl 5-(2-benzyloxyethyl)-4,5-dihydroisoxazole-3-carboxylate of following formula:

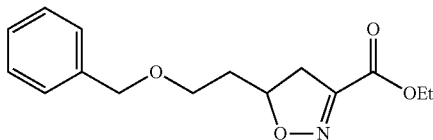 [SMILES: CCOC(=O)C1=NOC(CCOCc2ccccc2)C1]

¹H-NMR (CDCl₃) δ: 7.39-7.28 (5H, m), 5.03-4.95 (1H, m), 4.51 (2H, dd, J=16.3, 11.7 Hz), 4.33 (2H, q, J=7.2 Hz), 3.67-3.53 (2H, m), 3.28 (1H, dd, J=17.6, 11.0 Hz), 2.95 (1H, dd, J=17.6, 8.2 Hz), 2.10-1.99 (1H, m), 1.97-1.87 (1H, m), 1.36 (3H, t, J=7.1 Hz).

Reference Production Example 24

Ethyl 5-(3-benzyloxypropyl)-4,5-dihydroisoxazole-3-carboxylate (661 mg, 2.27 mmol) was added to ethanol (90 mL), potassium hydroxide (255 mg, 4.54 mmol) and water (4.5 mL) were added, and the mixture was stirred at room temperature for 1.5 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 615 mg of 5-(3-benzyloxypropyl)-4,5-dihydroisoxazole-3-carboxylic acid of following formula:

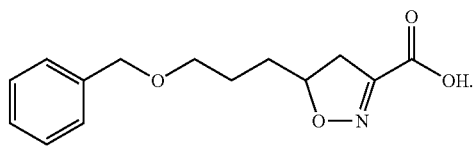

This was subjected to a next reaction without purification.
¹H-NMR (CDCl₃) δ: 7.39-7.28 (5H, m), 4.97-4.85 (1H, m), 4.51 (2H, s), 3.58-3.47 (2H, m), 3.27 (1H, dd, J=17.5, 11.1 Hz), 2.86 (1H, dd, J=17.6, 8.5 Hz), 1.92-1.62 (4H, m).

Reference Production Example 25

Ethyl nitroacetate (495 μL, 4.46 mmol), 5-benzyloxy-1-pentene (524 mg, 2.97 mmol) and 1,4-diazabicyclo[2.2.2]octane (67 mg, mmol) were added to chloroform (Amylene-added product) (1 mL), and the mixture was stirred at 90 degree for 2.5 hours. Thereafter, the mixture was stirred at 110 degree for 1.5 hours, and the reaction liquid was cooled to room temperature, and concentrated under reduced pressure. The resulting residue was subjected to silica gel column chromatography to obtain 661 mg of ethyl 5-(3-benzyloxypropyl)-4,5-dihydroisoxazole-3-carboxylate of following formula:

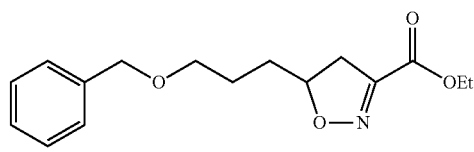 [SMILES: CCOC(=O)C1=NOC(CCCOCc2ccccc2)C1]

¹H-NMR (CDCl₃) δ: 7.38-7.28 (5H, m), 4.90-4.78 (1H, m), 4.50 (2H, s), 4.34 (2H, q, J=7.2 Hz), 3.58-3.45 (2H, m), 3.26 (1H, dd, J=17.6, 11.0 Hz), 2.86 (1H, dd, J=17.7, 8.4 Hz), 1.89-1.65 (4H, m), 1.37 (3H, t, J=7.1 Hz).

Reference Production Example 26

Ethyl 5-(4-benzyloxybutyl)-4,5-dihydroisoxazole-3-carboxylate (954 mg, 3.12 mmol) was added to ethanol (12 mL), potassium hydroxide (350 mg, 6.24 mmol) and water (6.2 mL) were added, and the mixture was stirred at room temperature for 1.5 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 928 mg of 5-(4-benzyloxybutyl)-4,5-dihydroisoxazole-3-carboxylic acid of following formula:

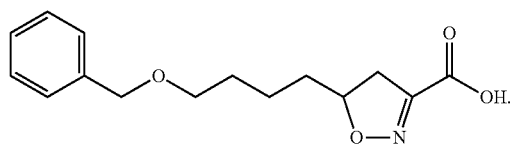

This was subjected to a next reaction without purification.
¹H-NMR (CDCl₃) δ: 7.39-7.28 (5H, m), 4.93-4.81 (1H, m), 4.51 (2H, s), 3.49 (2H, t, J=6.3 Hz), 3.26 (1H, dd, J=17.6, 11.0 Hz), 2.84 (1H, dd, J=17.6, 8.7 Hz), 1.86-1.73 (1H, m), 1.72-1.60 (3H, m), 1.58-1.42 (2H, m).

Reference Production Example 27

Ethyl nitroacetate (830 μL, 7.46 mmol), 6-benzyloxy-1-hexyne (946 mg, 4.97 mmol) and 1,4-diazabicyclo[2.2.2]octane (111 mg, 0.994 mmol) were added to chloroform (Amylene-added product) (1.7 mL), and the mixture was stirred at 90 degree for 3 hours. Thereafter, the mixture was stirred at 110 degree for 2 hours, and the reaction liquid was cooled to room temperature, and concentrated under reduced pressure. The resulting residue was subjected to silica gel column chromatography to obtain 954 mg of ethyl 5-(4-benzyloxybutyl)-4,5-dihydroisoxazole-3-carboxylate of following formula:

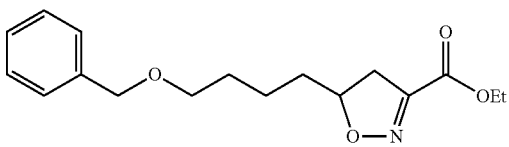 [SMILES: O=C(O)C1=NOC(CCCCOCc2ccccc2)C1]

¹H-NMR (CDCl₃) δ: 7.39-7.27 (5H, m), 4.86-4.73 (1H, m), 4.50 (2H, s), 4.35 (2H, q, J=7.2 Hz), 3.48 (2H, t, J=6.3 Hz), 3.25 (1H, dd, J=17.6, 11.0 Hz), 2.84 (1H, dd, J=17.6, 8.5 Hz), 1.84-1.73 (1H, m), 1.71-1.60 (3H, m), 1.56-1.42 (2H, m), 1.37 (3H, t, J=7.1 Hz).

Reference Production Example 28

Ethyl 5-(5-benzyloxypentyl)-4,5-dihydroisoxazole-3-carboxylate (368 mg, 1.15 mmol) was added to ethanol (4.6 mL), potassium hydroxide (129 mg, 2.30 mmol) and water (2.3 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 346 mg of 5-(5-benzyloxypentyl)-4,5-dihydroisoxazole-3-carboxylic acid of following formula:

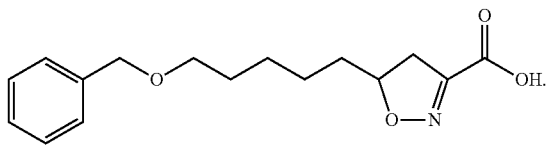 [SMILES: O=C(O)C1=NOC(CCCCCOCc2ccccc2)C1]

This was subjected to a next reaction without purification.
¹H-NMR (CDCl₃) δ: 7.37-7.27 (5H, m), 4.91-4.80 (1H, m), 4.51 (2H, s), 3.47 (2H, t, J=6.6 Hz), 3.25 (1H, dd, J=17.6, 11.0 Hz), 2.83 (1H, dd, J=17.7, 8.6 Hz), 1.83-1.72 (1H, m), 1.65-1.56 (3H, m), 1.48-1.30 (4H, m).

Reference Production Example 29

Ethyl nitroacetate (283 μL, 2.54 mmol), 7-benzyloxy-1-hexene (346 mg, 1.69 mmol) and 1,4-diazabicyclo[2.2.2]octane (38 mg, mmol) were added to chloroform (Amylene-added product) (560 μL), and the mixture was stirred at 90 degree for 3.5 hours. Thereafter, the mixture was stirred at 110 degree for 3 hours, and the reaction liquid was cooled to room temperature, and concentrated under reduced pressure. The resulting residue was subjected to silica gel column chromatography to obtain 368 mg of ethyl 5-(5-benzyloxypentyl)-4,5-dihydroisoxazole-3-carboxylate of following formula:

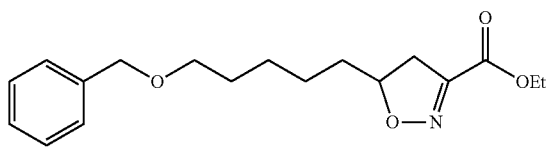 [SMILES: CCOC(=O)C1=NOC(CCCCCOCc2ccccc2)C1]

¹H-NMR (CDCl₃) δ: 7.38-7.27 (5H, m), 4.84-4.74 (1H, m), 4.50 (2H, s), 4.35 (2H, q, J=7.1 Hz), 3.47 (2H, t, J=6.5 Hz), 3.24 (1H, dd, J=17.5, 10.9 Hz), 2.83 (1H, dd, J=17.4, 8.5 Hz), 1.84-1.71 (1H, m), 1.68-1.58 (3H, m), 1.50-1.40 (3H, m), 1.37 (4H, t, J=7.1 Hz).

Reference Production Example 30

Ethyl 5-(6-benzyloxyhexyl)-4,5-dihydroisoxazole-3-carboxylate (350 mg, 1.05 mmol) was added to ethanol (4.2 mL), potassium hydroxide (117 mg, 2.10 mmol) and water (2.1 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 324 mg of 5-(6-benzyloxyhexyl)-4,5-dihydroisoxazole-3-carboxylic acid of following formula:

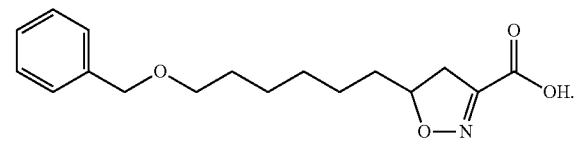 [SMILES: CCOC(=O)C1=NOC(CCCCCCOCc2ccccc2)C1]

This was subjected to a next reaction without purification.
¹H-NMR (CDCl₃) δ: 7.38-7.27 (5H, m), 4.91-4.80 (1H, m), 4.51 (2H, s), 3.47 (2H, t, J=6.6 Hz), 3.25 (1H, dd, J=17.6, 11.0 Hz), 2.83 (1H, dd, J=17.7, 8.6 Hz), 1.83-1.72 (1H, m), 1.67-1.57 (3H, m), 1.49-1.32 (6H, m).

Reference Production Example 31

Ethyl nitroacetate (251 μL, mmol), 8-benzyloxy-1-octene (330 mg, 1.51 mmol) and 1,4-diazabicyclo[2.2.2]octane (34 mg, 0.30 mmol) were added to chloroform (Amylene-added product) (0.5 mL), and the mixture was stirred at 90 degree for 3.5 hours. Thereafter, the mixture was stirred at 110 degree for 3 hours, and the reaction liquid was cooled to room temperature, and concentrated under reduced pressure. The resulting residue was subjected to silica gel column chromatography to obtain 350 mg of ethyl 5-(6-benzyloxyhexyl)-4,5-dihydroisoxazole-3-carboxylate of following formula:

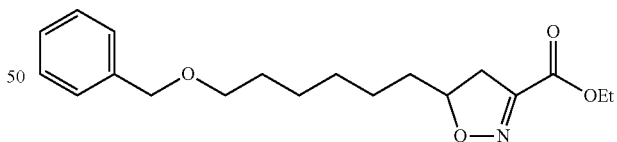

¹H-NMR (CDCl₃) δ: 7.37-7.27 (5H, m), 4.83-4.74 (1H, m), 4.50 (2H, s), 4.34 (2H, q, J=7.2 Hz), 3.46 (2H, t, J=6.5 Hz), 3.24 (1H, dd, J=17.5, 10.9 Hz), 2.83 (1H, dd, J=17.4, 8.5 Hz), 1.79-1.48 (10H, m), 1.37 (3H, t, J=7.1 Hz).

Reference Production Example 32

Ethyl 5-phenethyloxymethyl-4,5-dihydroisoxazole-3-carboxylate (1.52 g, 5.48 mmol) was added to ethanol (22 mL), potassium hydroxide (615 mg, 11.0 mmol) and water (11 mL) were added, and the mixture was stirred at room temperature for 3.5 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 1.39 g of 5-phenethyloxymethyl-4,5-dihydroisoxazole-3-carboxylic acid of following formula:

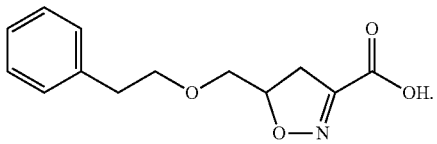

This was subjected to a next reaction without purification.
¹H-NMR (CDCl₃) δ: 7.28 (2H, tt, J=7.2, 1.9 Hz), 7.24-7.17 (3H, m), 5.02-4.93 (1H, m), 3.78-3.67 (2H, m), 3.61 (2H, ddd, J=25.9, 11.0, 4.1 Hz), 3.19 (1H, dd, J=17.6, 11.4 Hz), 3.08 (1H, dd, J=17.6, 8.2 Hz), 2.88 (2H, t, J=6.9 Hz).

Reference Production Example 33

Ethyl nitroacetate (1.3 mL, 11.9 mmol), 3-phenethyloxy-1-propene (1.29 g, 7.95 mmol) and 1,4-diazabicyclo[2.2.2]octane (178 mg, 1.59 mmol) were added to chloroform (Amylene-added product) (2.6 mL), and the mixture was stirred at 90 degree for 3 hours. Thereafter, the reaction liquid was cooled to room temperature, and concentrated under reduced pressure. The resulting residue was subjected to silica gel column chromatography to obtain 1.52 g of ethyl 5-phenethyloxymethyl-4,5-dihydroisoxazole-3-carboxylate of following formula:

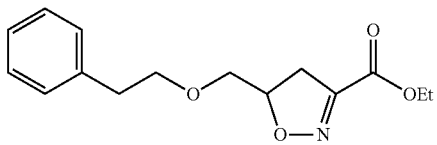 [SMILES: CCOC(=O)C1=NOC(COCCc2ccccc2)C1]

¹H-NMR (CDCl₃) δ: 7.31-7.27 (2H, m), 7.24-7.17 (3H, m), 4.96-4.87 (1H, m), 4.35 (2H, q, J=7.2 Hz), 3.78-3.65 (2H, m), 3.64-3.54 (2H, m), 3.19 (1H, dd, J=17.7, 11.3 Hz), 3.07 (1H, dd, J=17.7, 8.2 Hz), 2.88 (2H, t, J=6.9 Hz), 1.38 (3H, t, J=7.1 Hz).

Reference Production Example 34

Ethyl 5-(3-phenethyloxypropyl)-4,5-dihydroisoxazole-3-carboxylate (976 mg, 3.20 mmol) was added to ethanol (13 mL), potassium hydroxide (360 mg, 6.40 mmol) and water (6 mL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 1.07 g of 5-(3-phenethyloxypropyl)-4,5-dihydroisoxazole-3-carboxylic acid of following formula:

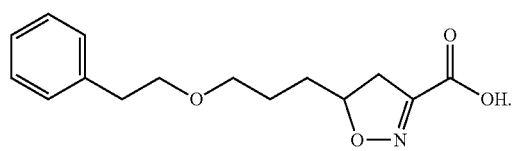 [SMILES: CCOC(=O)C1=NOC(CCCOCCc2ccccc2)C1]

This was subjected to a next reaction without purification.
¹H-NMR (CDCl₃) δ: 7.31-7.27 (2H, m), 7.24-7.18 (3H, m), 4.90-4.79 (1H, m), 3.64 (2H, t, J=7.1 Hz), 3.53-3.42 (2H, m), 3.22 (2H, dd, J=17.7, 11.1 Hz), 2.88 (2H, t, J=7.1 Hz), 2.81 (1H, dd, J=17.7, 8.6 Hz), 1.85-1.59 (4H, m).

Reference Production Example 35

Ethyl nitroacetate (875 μL, 7.88 mmol), 5-phenethyloxy-1-pentene (1.0 g, 5.26 mmol) and 1,4-diazabicyclo[2.2.2]octane (118 mg, 1.05 mmol) were added to chloroform (Amylene-added product) (1.8 mL), and the mixture was stirred at 90 degree for 4 hours. Thereafter, the reaction liquid was cooled to room temperature, and concentrated under reduced pressure. The resulting residue was subjected to silica gel column chromatography to obtain 976 mg of ethyl 5-(3-phenethyloxypropyl)-4,5-dihydroisoxazole-3-carboxylate having the following formula:

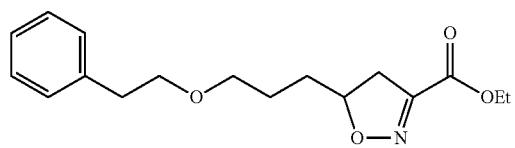

¹H-NMR (CDCl₃) δ: 7.31-7.27 (2H, m), 7.25-7.18 (3H, m), 4.84-4.73 (1H, m), 4.35 (2H, q, J=7.1 Hz), 3.63 (2H, t, J=7.1 Hz), 3.51-3.42 (2H, m), 3.21 (1H, dd, J=17.4, 10.9 Hz), 2.87 (2H, t, J=7.0 Hz), 2.81 (1H, dd, J=17.4, 8.4 Hz), 1.80-1.62 (4H, m), 1.37 (3H, t, J=7.1 Hz).

Reference Production Example 36

Ethyl 5-(2-naphthyloxymethyl)-4,5-dihydroisoxazole-3-carboxylate (3.65 g, 12.2 mmol) was added to ethanol (20 mL), potassium hydroxide (1.37 g, 24.4 mmol) and water (10 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 2.11 g of 5-(2-naphthyloxymethyl)-4,5-dihydroisoxazole-3-carboxylic acid of following formula:

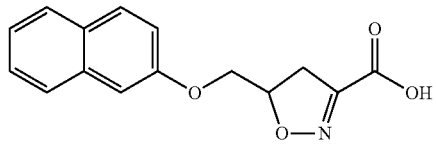 [SMILES: O=C(O)C1=NOC(COc2ccc3ccccc3c2)C1]

MS (ESI) m/z [M+H]⁺: 272.

Reference Production Example 37

Ethyl nitroacetate (4.02 g, 33.7 mmol), 3-(2-naphthyloxy)-1-propene (4.97 g, 27.0 mmol) and 1,4-diazabicyclo[2.2.2]octane (0.61 g, 5.4 mmol) were added to chloroform (Amylene-added product) (7 mL). The mixed liquid was heated to reflux for 24 hours. Thereafter, the resultant was cooled to room temperature, and dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 3.50 g of ethyl 5-(2-naphthyloxymethyl)-4,5-dihydroisoxazole-3-carboxylate of following formula:

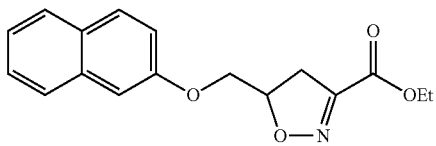 [SMILES: CCOC(=O)C1=NOC(COc2ccc3ccccc3c2)C1]

MS (ESI) m/z [M+H]$^+$: 300.

Reference Production Example 38

Ethyl 5-[(2-naphthylmethyl)oxymethyl]-4,5-dihydroisoxazole-3-carboxylate (3.30 g, 10.5 mmol) was added to ethanol (20 mL), potassium hydroxide (1.18 g, 21.1 mmol) and water (10 mL) were added, and the mixture was stirred at room temperature overnight. Thereafter, the resultant was concentrated under reduced pressure. Dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 1.89 g of 5-[(2-naphthylmethyl)oxymethyl]-4,5-dihydroisoxazole-3-carb oxylic acid of following formula:

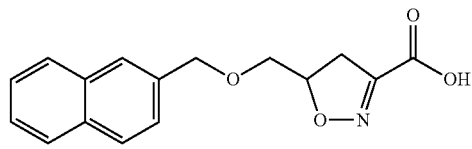 [SMILES: O=C(O)C1=NOC(COCc2ccc3ccccc3c2)C1]

MS (ESI) m/z [M+H]$^+$: 286.

Reference Production Example 39

Ethyl 2-chloro-2-(hydroxyimino)acetate (5.93 g, 39.1 mmol) and 3-(2-naphthylmethyloxy)-1-propene (4.97 g, 32.6 mmol) were added to N,N-dimethylformamide (80 mL). Triethylamine (3.95 g, 39.1 mmol) was added to the mixed liquid at room temperature, and the mixture was stirred at room temperature overnight. Thereafter, dilute hydrochloric acid was added to the reaction mixture, followed by extraction with ethyl acetate two times. The organic layer was washed with an aqueous saturated sodium chloride solution, dried with anhydrous sodium sulfate, and filtered, and the filtrate was concentrated under reduced pressure. The residue was subjected to silica gel column chromatography to obtain 3.30 g of ethyl 5-[(2-naphthylmethyl)oxymethyl]-4,5-dihydroisoxazole-3-carboxylate of following formula:

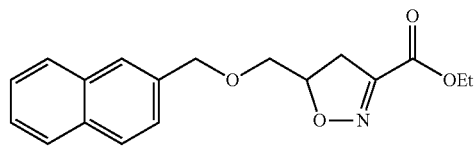 [SMILES: CCOC(=O)C1=NOC(COCc2ccc3ccccc3c2)C1]

MS (ESI) m/z [M+H]$^+$: 314.

Reference Production Example 40

Ethyl 5-[(2-naphthylmethyl)oxypropyl]-4,5-dihydroisoxazole-3-carboxylate (2.21 g, 6.47 mmol) was added to ethanol (25 mL), potassium hydroxide (726 mg, 12.9 mmol) and water (13 mL) were added, and the mixture was stirred at room temperature for 2 hours. Thereafter, 1N hydrochloric acid was added to the reaction mixture, followed by extraction with ethyl acetate. The organic layer was dried with anhydrous magnesium sulfate, and filtered, and the filtrate was concentrated under reduced pressure to obtain 1.29 g of 5-[(2-naphthylmethyl)oxypropyl]-4,5-dihydroisoxazole-3-carb oxylic acid of following formula:

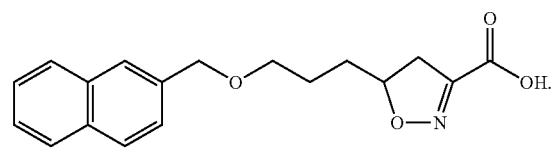

This was subjected to a next reaction without purification.
$^1$H-NMR (CDCl$_3$) δ: 7.86-7.80 (3H, m), 7.77 (1H, br), 7.53-7.43 (3H, m), 4.98-4.88 (1H, m), 4.67 (2H, s), 3.61-3.51 (2H, m), 3.27 (1H, dd, J=17.6, 11.0 Hz), 2.87 (1H, dd, J=17.7, 8.6 Hz), 1.94-1.64 (5H, m).

Reference Production Example 41

Ethyl nitroacetate (1.1 mL, 10.3 mmol), 5-(2-naphthylmethyloxy)-1-pentene (1.55 g, 6.85 mmol) and 1,4-diazabicyclo[2.2.2.]octane (154 mg, 1.37 mmol) were added to chloroform (Amylene-added product) (2.3 mL), and the mixture was stirred at 90 degree for 3 hours. Thereafter, ethyl nitroacetate (380 μL, 3.42 mmol) and 1,4-diazabicyclo[2.2.2]octane (154 mg, 1.37 mmol) were added, and the mixture was stirred at 90 degree for 7 hours. Thereafter, the reaction liquid was cooled to room temperature, and concentrated under reduced pressure. The resulting residue was subjected to silica gel column chromatography to obtain 2.21 g of ethyl 5-[(2-naphthylmethyl)oxypropyl]-4,5-dihydroisoxazole-3-carboxylate of following formula:

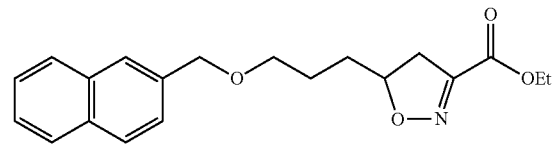 [SMILES: O=C(O)C1=NOC(CCCOCc2ccc3ccccc3c2)C1]

$^1$H-NMR (CDCl$_3$) δ: 7.85-7.82 (3H, m), 7.77 (1H, br), 7.50-7.44 (3H, m), 4.89-4.80 (1H, m), 4.67 (2H, s), 4.34 (2H, q, J=7.1 Hz), 3.61-3.50 (2H, m), 3.26 (1H, dd, J=17.4, 10.9 Hz), 2.86 (1H, dd, J=17.4, 8.4 Hz), 1.88-1.68 (4H, m), 1.36 (3H, t, J=7.1 Hz).

Reference Production Example 42

Ethyl 4-methyl-5-phenoxymethyl-4,5-dihydroisoxazole-3-carboxylate (325 mg, 1.23 mmol) was added to ethanol (5 mL), potassium hydroxide (139 mg, 2.47 mmol) and water (2.5 mL) were added, and the mixture was stirred at room temperature for 5.5 hours. Thereafter, 1N hydrochloric acid was added to the reaction mixture, followed by extraction with ethyl acetate. The organic layer was dried with anhydrous magnesium sulfate, and filtered, and the filtrate was concentrated under reduced pressure to obtain 300 mg of 4-methyl-5-phenoxymethyl-4,5-dihydroisoxazole-3-carboxylic acid of following formula:

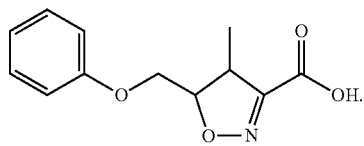

This was subjected to a next reaction without purification.
$^1$H-NMR (CDCl$_3$) δ: 7.32-7.27 (2H, m), 7.01-6.96 (1H, m), 6.91-6.87 (2H, m), 5.05 (1H, dt, J=13.7, 6.5 Hz), 4.29-4.19 (2H, m), 4.16-4.08 (1H, m), 3.56-3.51 (1H, m), 1.50 (3H, d, J=6.3 Hz).

Reference Production Example 43

Ethyl nitroacetate (2.8 mL, 24.9 mmol), 4-benzyloxy-1-butene (2.46 g, 16.6 mmol) and 1,4-diazabicyclo[2.2.2]octane (372 mg, 3.32 mmol) were added to chloroform (Amylene-added product) (5.5 mL), and the mixture was stirred at 90 degree for 7 hours. Thereafter, the mixture was stirred at 100 degree for 2 hours, and the reaction liquid was cooled to room temperature, and concentrated under reduced pressure. The resulting residue was subjected to silica gel column chromatography to obtain 1.40 g of ethyl 4-methyl-5-phenoxymethyl-4,5-dihydroisoxazole-3-carboxylate of following formula:

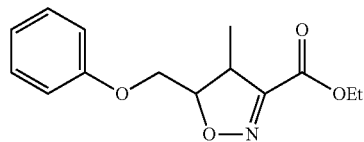 [SMILES: CC1C(C(=O)O)=NOC1COc1ccccc1]

$^1$H-NMR (CDCl$_3$) δ: 7.32-7.27 (2H, m), 7.01-6.96 (1H, m), 6.93-6.87 (2H, m), 4.99-4.92 (1H, m), 4.40-4.31 (2H, m), 4.27 (1H, dd, J=9.3, 3.4 Hz), 4.16 (1H, dd, J=9.4, 7.4 Hz), 3.53 (1H, td, J=7.2, 3.4 Hz), 1.46 (3H, d, J=6.3 Hz), 1.37 (3H, t, J=7.1 Hz).

Reference Production Example 44

Ethyl 6-phenoxymethyl-5,6-dihydro-4H-[1,2]oxazine-3-carboxylate (350 mg, 1.33 mmol) was added to ethanol (5.3 mL), potassium hydroxide (150 mg, 2.65 mmol) and water (2.7 mL) were added, and the mixture was stirred at room temperature overnight. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 218 mg of 6-phenoxymethyl-5,6-dihydro-4H-[1,2]oxazine-3-carboxylic acid of following formula:

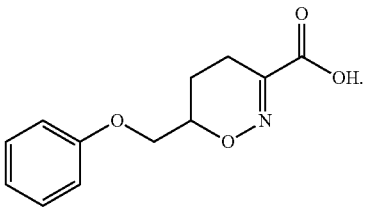

This was subjected to a next reaction without purification.
$^1$H-NMR (CDCl$_3$) δ: 7.35-7.28 (2H, m), 7.00 (1H, t, J=7.3 Hz), 6.93 (2H, dd, J=8.7, 0.9 Hz), 4.25-4.17 (1H, m), 4.12 (2H, q, J=7.1 Hz), 2.76 (1H, ddd, J=19.4, 6.1, 2.5 Hz), 2.54-2.45 (1H, m), 2.26-2.17 (1H, m), 2.02-1.88 (1H, m).

Reference Production Example 45

Ethyl 6-hydroxymethyl-5,6-dihydro-4H-[1,2]oxazine-3-carboxylate (360 mg, 1.92 mmol) synthesized by the method known in the reference was added to tetrahydrofuran (19 mL), phenol (271 mg, 2.88 mmol) and triphenylphosphine (755 mg, 2.88 mmol) were added, and diisopropyl azodicarboxylate (40% toluene solution) (1.4 mL, 2.88 mmol) was added dropwise slowly at room temperature. Thereafter, the mixture was stirred at room temperature for 4 hours, and phenol (271 mg, 2.88 mmol), triphenylphosphine (755 mg, 2.88 mmol) and diisopropyl azodicarboxylate (40% toluene solution) (1.4 mL, 2.88 mmol) were added. After the mixture was stirred at room temperature for 2 hours, the reaction mixture was concentrated under reduced pressure. The resulting residue was subjected to silica gel column chromatography to obtain 340 mg of ethyl 6-phenoxymethyl-5,6-dihydro-4H-[1,2]oxazine-3-carboxylate of following formula:

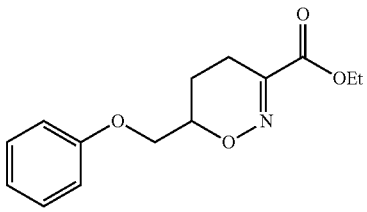 [SMILES: O=C(O)C1=NOC(COc2ccccc2)CC1]

$^1$H-NMR (CDCl$_3$) δ: 7.30 (2H, t, J=7.9 Hz), 6.98 (1H, t, J=7.5 Hz), 6.93 (2H, d, J=8.4 Hz), 4.34 (2H, q, J=7.1 Hz), 4.24 (1H, dd, J=9.6, 4.6 Hz), 4.21-4.15 (1H, m), 4.11 (1H, dd, J=8.9, 5.5 Hz), 2.69 (1H, dq, J=19.3, 2.9 Hz), 2.50-2.41 (1H, m), 2.25-2.15 (1H, m), 1.97-1.84 (1H, m), 1.37 (3H, t, J=7.1 Hz).

Reference Production Example 46

Ethyl 6-(3-chloro-phenoxymethyl)-5,6-dihydro-4H-[1,2]oxazine-3-carboxylate (804 mg, 2.70 mmol) was added to ethanol (10.8 mL), potassium hydroxide (303 mg, 5.40 mmol) and water (5.4 mL) were added, and the mixture was stirred at room temperature for 1.5 hours. Thereafter, 1N hydrochloric acid was added to the reaction mixture, followed by extraction with ethyl acetate. The organic layer was dried with anhydrous magnesium sulfate, and filtered, and the filtrate was concentrated under reduced pressure to obtain 960 mg of 6-(3-chloro-phenoxymethyl)-5,6-dihydro-4H-[1,2]oxazine-3-carboxylic acid of following formula:

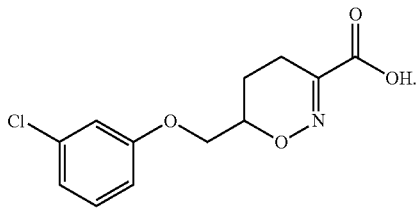 [SMILES: O=C(O)C1=NOC(COc2cccc(Cl)c2)CC1]

This was subjected to a next reaction without purification.
$^1$H-NMR (CDCl$_3$) δ: 7.23 (1H, t, J=8.2 Hz), 7.00-6.97 (1H, m), 6.94 (1H, t, J=2.2 Hz), 6.84-6.81 (1H, m), 4.27-4.16 (1H, m), 4.12 (2H, q, J=7.2 Hz), 2.77 (1H, ddd, J=19.7, 6.1, 2.3 Hz), 2.55-2.45 (1H, m), 2.25-2.16 (1H, m), 2.01-1.87 (1H, m).

Reference Production Example 47

Ethyl 6-hydroxymethyl-5,6-dihydro-4H-[1,2]oxazine-3-carboxylate (374 mg, 2.0 mmol) synthesized by the method known in the reference was added to tetrahydrofuran (20 mL), metachlorophenol (386 mg, 3.0 mmol) and triphenylphosphine (787 mg, 3.0 mmol) were added, diisopropyl azodicarboxylate (40% toluene solution) (1.4 mL, 3.0 mmol) was added dropwise slowly at room temperature. Thereafter, the mixture was stirred at room temperature for 3 hours, and metachlorophenol (386 mg, 3.0 mmol), triphenylphosphine (787 mg, 3.0 mmol) and diisopropyl azodicarboxylate (40% toluene solution) (1.4 mL, 3.0 mmol) were added. After the mixture was stirred at room temperature for 2 hours, the reaction mixture was concentrated under reduced pressure. The resulting residue was subjected to silica gel column chromatography to obtain 804 mg of ethyl 6-(3-chloro-phenoxymethyl)-5,6-dihydro-4H-[1,2]oxazine-3-carboxylate of following formula:

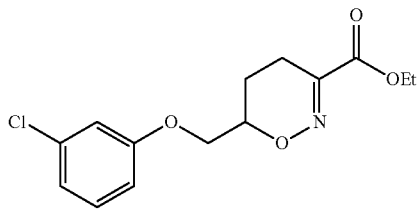

$^1$H-NMR (CDCl$_3$) δ: 7.21 (1H, t, J=8.1 Hz), 6.96 (1H, t, J=4.8 Hz), 6.93 (1H, t, J=2.2 Hz), 6.82 (1H, dd, J=8.4, 2.4 Hz), 4.34 (2H, q, J=7.2 Hz), 4.21 (1H, dd, J=9.0, 4.5 Hz), 4.19-4.13 (1H, m), 4.11 (1H, dd, J=8.9, 4.4 Hz), 2.70 (1H, ddd, J=19.4, 6.2, 2.7 Hz), 2.51-2.41 (1H, m), 2.21-2.14 (1H, m), 1.95-1.85 (1H, m), 1.37 (3H, t, J=7.1 Hz).

Reference Production Example 48

Ethyl 6-benzyloxymethyl-5,6-dihydro-4H-[1,2]oxazine-3-carboxylate (87 mg, 0.314 mmol) was added to ethanol (1.2 mL), potassium hydroxide (35 mg, 0.628 mmol) and water (630 μL) were added, and the mixture was stirred at room temperature for 2 hours. Thereafter, 2N hydrochloric acid was added to the reaction mixture, followed by extraction with ethyl acetate. The organic layer was dried with anhydrous magnesium sulfate, and filtered, and the filtrate was concentrated under reduced pressure to obtain 54 mg of 6-benzyloxymethyl-5,6-dihydro-4H-[1,2]oxazine-3-carboxylic acid of following formula:

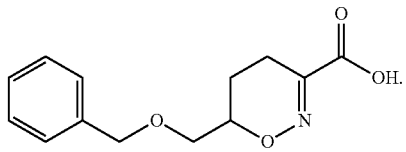

This was subjected to a next reaction without purification.
$^1$H-NMR (CDCl$_3$) δ: 7.42-7.29 (5H, m), 4.61 (2H, s), 4.08-4.02 (1H, m), 3.70 (2H, dd, J=4.8, 2.5 Hz), 2.68 (1H, ddd, J=19.5, 6.1, 2.3 Hz), 2.47-2.37 (1H, m), 2.11-2.03 (1H, m), 1.90-1.76 (1H, m).

Reference Production Example 49

Ethyl 6-hydroxymethyl-5,6-dihydro-4H-[1,2]oxazine-3-carboxylate (570 mg, 3.05 mmol) synthesized by the method known in the reference was added to tetrahydrofuran (20 mL), the system was replaced with nitrogen, and cooled to 0 degree, sodium hydride (60%) (134 mg, 3.36 mmol) was added, and the mixture was stirred at room temperature for 1 hour. Thereafter, benzyl bromide (362 μL, 3.05 mmol) was added, and the mixture was stirred at room temperature for 5.5 hours. An aqueous saturated solution of ammonium chloride was added to the reaction mixture, followed by extraction with ethyl acetate. The organic layer was washed with water and an aqueous saturated sodium chloride solution, dried with anhydrous magnesium sulfate, and filtered, and the filtrate was concentrated under reduced pressure. The resulting residue was subjected to silica gel column chromatography to obtain 87 mg of ethyl 6-benzyloxymethyl-5,6-dihydro-4H-[1,2]oxazine-3-carboxylate of following formula:

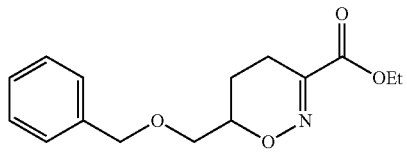 [SMILES: CCOC(=O)C1=NOC(COCc2ccccc2)CC1]

$^1$H-NMR (CDCl$_3$) δ: 7.41-7.28 (5H, m), 4.61 (2H, s), 4.32 (2H, q, J=7.1 Hz), 4.06-3.94 (1H, m), 3.74-3.64 (2H, m), 2.62 (1H, dt, J=19.3, 2.9 Hz), 2.44-2.34 (1H, m), 2.10-2.02 (1H, m), 1.88-1.71 (1H, m), 1.36 (3H, t, J=7.1 Hz).

Reference Production Example 50

Commercially available 3,4-dihydro-2H-pyran-2-methanol (1.0 mL, 9.64 mmol) was added to tetrahydrofuran (50 mL), phenol (1.4 g, 14.5 mmol) and triphenylphosphine (3.8 g, 14.5 mmol) were added, and diisopropyl azodicarboxylate (about 1.9 mol/L toluene solution) (7.6 mL, 14.5 mmol) was added dropwise slowly at room temperature. Thereafter, the mixture was stirred at room temperature overnight, and the reaction mixture was concentrated under reduced pressure. The resulting residue was subjected to silica gel column chromatography to obtain 1.31 g of 2-phenoxymethyl-3,4-dihydro-2H-pyran of following formula:

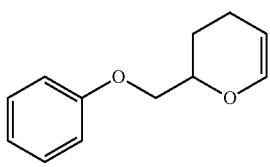 [SMILES: C1=COC(COc2ccccc2)CC1]

$^1$H-NMR (CDCl$_3$) δ: 7.32-7.26 (2H, m), 6.98-6.92 (3H, m), 6.43 (1H, dt, J=6.2, 1.8 Hz), 4.76-4.72 (1H, m), 4.25-4.18 (1H, m), 4.11 (1H, dd, J=9.9, 6.0 Hz), 4.01 (1H, dd, J=9.7, 4.8 Hz), 2.21-2.11 (1H, m), 2.08-2.04 (1H, m), 2.03-1.96 (1H, m), 1.87-1.75 (1H, m).

Reference Production Example 51

Commercially available 3,4-dihydro-2H-pyran-2-methanol (1.0 mL, 9.64 mmol) was added to tetrahydrofuran (50 mL), the system was replaced with nitrogen, and sodium hydride (424 mg, 10.6 mmol) was added in portions under ice-cooling. After the mixture was stirred at room temperature for 40 minutes, benzyl bromide (1.1 mL, 9.64 mmol) was added dropwise slowly. Thereafter, the mixture was stirred at room temperature for 1 hour, and an aqueous saturated ammonium chloride solution was added to the reaction mixture. After extraction with methyl tertiary-butyl ether, and washing with an aqueous saturated sodium chloride solution, the resultant was dried using anhydrous magnesium sulfate. The organic layer was concentrated under reduced pressure, and the resulting residue was subjected to silica gel column chromatography to obtain 1.73 g of 2-benzyloxymethyl-3,4-dihydro-2H-pyran of following formula:

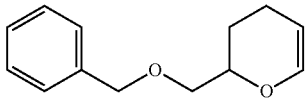

$^1$H-NMR (CDCl$_3$) δ: 7.41-7.27 (5H, m), 6.40 (1H, dt, J=4.0, 2.0 Hz), 4.71-4.67 (1H, m), 4.62 (1H, d, J=12.2 Hz), 4.57 (1H, d, J=12.2 Hz), 4.03 (1H, tdd, J=8.3, 4.2, 2.0 Hz), 3.59 (1H, dd, J=10.2, 6.3 Hz), 3.52 (1H, dd, J=10.0, 4.3 Hz), 2.15-2.05 (1H, m), 2.01-1.93 (1H, m), 1.87-1.82 (1H, m), 1.76-1.63 (1H, m).

Then, specific examples of the present amide compound are shown below.

An amide compound of formula (Y-1):

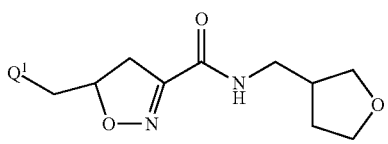

wherein Q$^1$ represents any group selected from the following Group (Q-1).

An amide compound of formula (Y-2):

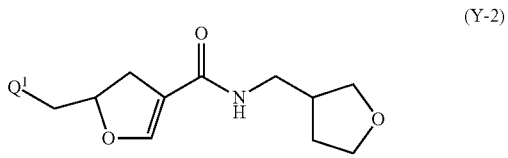

wherein Q$^1$ represents any group selected from the following Group (Q-1).

An amide compound of formula (Y-3):

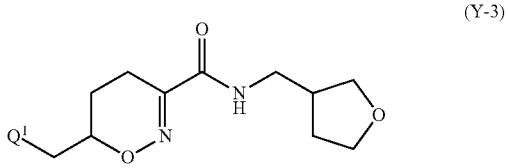

wherein Q$^1$ represents any group selected from the following Group (Q-1).

An amide compound of formula (Y-4):

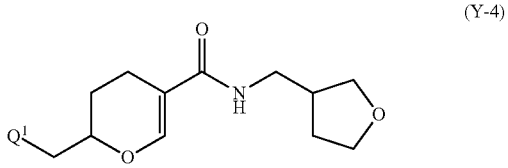

wherein Q$^1$ represents any group selected from the following Group (Q-1).
(Group Q-1)
an ethyl group, a propyl group, a butyl group, a pentyl group,
a 2,2,2-trifluoroethyl group, a 3,3,3-trifluoropropyl group,
a 4,4,4-trifluorobutyl group, a 5,5,5-trifluoropentyl group,
a phenyl group, a benzyl group, a 2-phenylethyl group,
a 3-phenylpropyl group, a 4-phenylbutyl group,
a 2-fluorophenyl group, a 2-fluorobenzyl group,
a 2-(2-fluorophenyl)ethyl group,
a 3-(2-fluorophenyl)propyl group,
a 4-(2-fluorophenyl)butyl group, a 3-fluorophenyl group,
a 3-fluorobenzyl group, a 2-(3-fluorophenyl)ethyl group,
a 3-(3-fluorophenyl)propyl group,
a 4-(3-fluorophenyl)butyl group, a 4-fluorophenyl group,
a 4-fluorobenzyl group, a 2-(4-fluorophenyl)ethyl group,
a 3-(4-fluorophenyl)propyl group,
a 4-(4-fluorophenyl)butyl group, a 2-chlorophenyl group,
a 2-chlorobenzyl group, a 2-(2-chlorophenyl)ethyl group,
a 3-(2-chlorophenyl)propyl group,
a 4-(2-chlorophenyl)butyl group, a 3-chlorophenyl group,
a 3-chlorobenzyl group, a 2-(3-chlorophenyl)ethyl group,
a 3-(3-chlorophenyl)propyl group,
a 4-(3-chlorophenyl)butyl group, a 4-chlorophenyl group,
a 4-chlorobenzyl group, a 2-(4-chlorophenyl)ethyl group,
a 3-(4-chlorophenyl)propyl group,
a 4-(4-chlorophenyl)butyl group, a 2-bromophenyl group,
a 2-bromobenzyl group, a 2-(2-bromophenyl)ethyl group,
a 3-(2-bromophenyl)propyl group,
a 4-(2-bromophenyl)butyl group, a 3-bromophenyl group,
a 3-bromobenzyl group, a 2-(3-bromophenyl)ethyl group, a 3-(3-bromophenyl)propyl group,
a 4-(3-bromophenyl)butyl group, a 4-bromophenyl group,
a 4-bromobenzyl group, a 2-(4-bromophenyl)ethyl group,
a 3-(4-bromophenyl)propyl group,
a 4-(4-bromophenyl)butyl group,
a 3-bromo-5-fluorophenyl group,
a 3-bromo-5-fluorobenzyl group,
a 2-(3-bromo-5-fluorophenyl)ethyl group,
a 3-(3-bromo-5-fluorophenyl)propyl group,
a 4-(3-bromo-5-fluorophenyl)butyl group,
a 2-trifluoromethylphenyl group,
a 2-trifluoromethylbenzyl group,
a 2-(2-trifluoromethylphenyl)ethyl group,
a 3-(2-trifluoromethylphenyl)propyl group,
a 4-(2-trifluoromethylphenyl)butyl group,
a 3-trifluoromethylphenyl group,
a 3-trifluoromethylbenzyl group,
a 2-(3-trifluoromethylphenyl)ethyl group,
a 3-(3-trifluoromethylphenyl)propyl group,
a 4-(3-trifluoromethylphenyl)butyl group,
a 4-trifluoromethylphenyl group,
a 4-trifluoromethylbenzyl group,
a 2-(4-trifluoromethylphenyl)ethyl group,
a 3-(4-trifluoromethylphenyl)propyl group,
a 4-(4-trifluoromethylphenyl)butyl group,
a 2-trifluoromethoxyphenyl group,
a 2-trifluoromethoxybenzyl group,
a 2-(2-trifluoromethoxyphenyl)ethyl group,
a 3-(2-trifluoromethoxyphenyl)propyl group,
a 4-(2-trifluoromethoxyphenyl)butyl group,
a 3-trifluoromethoxyphenyl group,
a 3-trifluoromethoxybenzyl group,
a 2-(3-trifluoromethoxyphenyl)ethyl group,
a 3-(3-trifluoromethoxyphenyl)propyl group,
a 4-(3-trifluoromethoxyphenyl)butyl group,
a 4-trifluoromethoxyphenyl group,
a 4-trifluoromethoxybenzyl group,
a 2-(4-trifluoromethoxyphenyl)ethyl group,
a 3-(4-trifluoromethoxyphenyl)propyl group,
a 4-(4-trifluoromethoxyphenyl)butyl group,
a 2-trifluoromethylsulfanylphenyl group,
a 2-trifluoromethylsulfanylbenzyl group,
a 2-(2-trifluoromethylsulfanylphenyl)ethyl group,
a 3-(2-trifluoromethylsulfanylphenyl)propyl group,
a 4-(2-trifluoromethylsulfanylphenyl)butyl group,
a 3-trifluoromethylsulfanylphenyl group,
a 3-trifluoromethylsulfanylbenzyl group,
a 2-(3-trifluoromethylsulfanylphenyl)ethyl group,
a 3-(3-trifluoromethylsulfanylphenyl)propyl group,
a 4-(3-trifluoromethylsulfanylphenyl)butyl group,
a 4-trifluoromethylsulfanylphenyl group,
a 4-trifluoromethylsulfanylbenzyl group,
a 2-(4-trifluoromethylsulfanylphenyl)ethyl group,
a 3-(4-trifluoromethylsulfanylphenyl)propyl group,
a 4-(4-trifluoromethylsulfanylphenyl)butyl group,
a 1-naphthyl group, a 1-naphthylmethyl group,
a 2-(1-naphthyl)ethyl group,
a 3-(1-naphthyl)propyl group,
a 4-(1-naphthyl)butyl group, a 2-naphthyl group,
a 2-naphthylmethyl group, a 2-(2-naphthyl)ethyl group,
a 3-(2-naphthyl)propyl group, a 8-fluoro-2-naphthyl group,
a (8-fluoro-2-naphthyl)methyl group,
a 2-(8-fluoro-2-naphthyl)ethyl group,
a 3-(8-fluoro-2-naphthyl)propyl group,
a 8-chloro-2-naphthyl group,
a (8-chloro-2-naphthyl)methyl group,
a 2-(8-chloro-2-naphthyl)ethyl group, a 3-(8-chloro-2-naphthyl)propyl group,
a 8-bromo-2-naphthyl group,
a (8-bromo-2-naphthyl)methyl group,
a 2-(8-bromo-2-naphthyl)ethyl group,
a 3-(8-bromo-2-naphthyl)propyl group.

An amide compound of formula (Y-5):

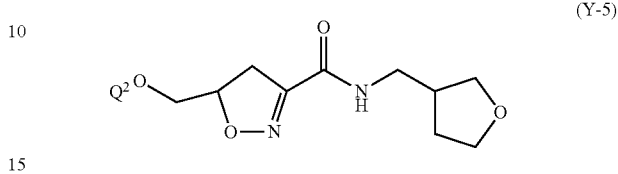

(Y-5)

wherein $Q^2$ represents any group selected from the following Group (Q-2).

An amide compound of formula (Y-6):

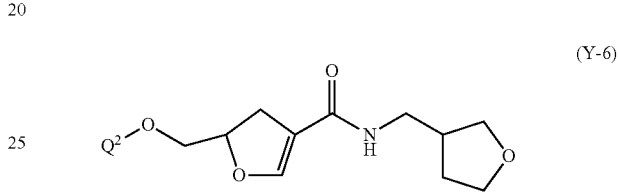

(Y-6)

wherein $Q^2$ represents any group selected from the following Group (Q-2).

An amide compound of formula (Y-7):

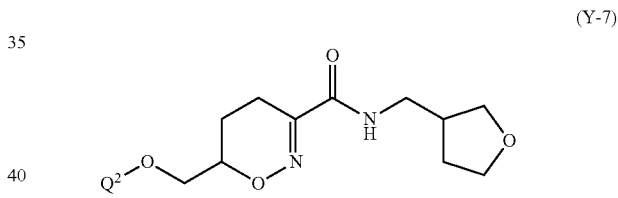

(Y-7)

wherein $Q^2$ represents any group selected from the following Group (Q-2).

An amide compound of formula (Y-8):

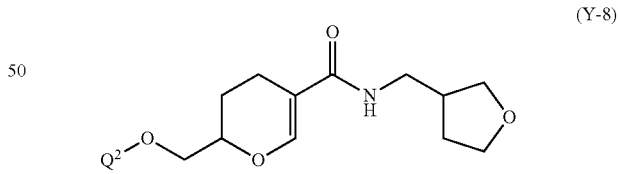

(Y-8)

wherein $Q^2$ represents any group selected from the following Group (Q-2).
(Group Q-2)
an ethyl group, a propyl group, a butyl group,
a 2,2,2-trifluoroethyl group,
a 3,3,3-trifluoropropyl group, a 4,4,4-trifluorobutyl group,
a phenyl group, a benzyl group, a 2-phenylethyl group,
a 3-phenylpropyl group, a 2-fluorophenyl group,
a 2-fluorobenzyl group, a 2-(2-fluorophenyl)ethyl group,
a 3-(2-fluorophenyl)propyl group, a 3-fluorophenyl group,
a 3-fluorobenzyl group, a 2-(3-fluorophenyl)ethyl group,
a 3-(3-fluorophenyl)propyl group, a 4-fluorophenyl group, a 4-fluorobenzyl group, a 2-(4-fluorophenyl)ethyl group,
a 3-(4-fluorophenyl)propyl group, a 2-chlorophenyl group,
a 2-chlorobenzyl group, a 2-(2-chlorophenyl)ethyl group,
a 3-(2-chlorophenyl)propyl group, a 3-chlorophenyl group,
a 3-chlorobenzyl group, a 2-(3-chlorophenyl)ethyl group,
a 3-(3-chlorophenyl)propyl group, a 4-chlorophenyl group,
a 4-chlorobenzyl group, a 2-(4-chlorophenyl)ethyl group,
a 3-(4-chlorophenyl)propyl group, a 2-bromophenyl group,
a 2-bromobenzyl group, a 2-(2-bromophenyl)ethyl group,
a 3-(2-bromophenyl)propyl group, a 3-bromophenyl group,
a 3-bromobenzyl group, a 2-(3-bromophenyl)ethyl group,
a 3-(3-bromophenyl)propyl group, a 4-bromophenyl group,
a 4-bromobenzyl group, a 2-(4-bromophenyl)ethyl group,
a 3-(4-bromophenyl)propyl group,
a 3-bromo-5-fluorophenyl group,
a 3-bromo-5-fluorobenzyl group,
a 2-(3-bromo-5-fluorophenyl)ethyl group,
a 3-(3-bromo-5-fluorophenyl)propyl group,
a 2-trifluoromethylphenyl group,
a 2-trifluoromethylbenzyl group,
a 2-(2-trifluoromethylphenyl)ethyl group,
a 3-(2-trifluoromethylphenyl)propyl group,
a 3-trifluoromethylphenyl group,
a 3-trifluoromethylbenzyl group,
a 2-(3-trifluoromethylphenyl)ethyl group,
a 3-(3-trifluoromethylphenyl)propyl group,
a 4-trifluoromethylphenyl group,
a 4-trifluoromethylbenzyl group,
a 2-(4-trifluoromethylphenyl)ethyl group,
a 3-(4-trifluoromethylphenyl)propyl group,
a 2-trifluoromethoxyphenyl group,
a 2-trifluoromethoxybenzyl group,
a 2-(2-trifluoromethoxyphenyl)ethyl group,
a 3-(2-trifluoromethoxyphenyl)propyl group,
a 3-trifluoromethoxyphenyl group,
a 3-trifluoromethoxybenzyl group,
a 2-(3-trifluoromethoxyphenyl)ethyl group,
a 3-(3-trifluoromethoxyphenyl)propyl group,
a 4-trifluoromethoxyphenyl group,
a 4-trifluoromethoxybenzyl group,
a 2-(4-trifluoromethoxyphenyl)ethyl group,
a 3-(4-trifluoromethoxyphenyl)propyl group,
a 2-trifluoromethylsulfanylphenyl group,
a 2-trifluoromethylsulfanylbenzyl group,
a 2-(2-trifluoromethylsulfanylphenyl)ethyl group,
a 3-(2-trifluoromethylsulfanylphenyl)propyl group,
a 3-trifluoromethylsulfanylphenyl group,
a 3-trifluoromethylsulfanylbenzyl group,
a 2-(3-trifluoromethylsulfanylphenyl)ethyl group,
a 3-(3-trifluoromethylsulfanylphenyl)propyl group,
a 4-trifluoromethylsulfanylphenyl group,
a 4-trifluoromethylsulfanylbenzyl group,
a 2-(4-trifluoromethylsulfanylphenyl)ethyl group,
a 3-(4-trifluoromethylsulfanylphenyl)propyl group,
a 1-naphthyl group, a 1-naphthylmethyl group,
a 2-(1-naphthyl)ethyl group, a 3-(1-naphthyl)propyl group,
2-naphthyl group, a 2-naphthylmethyl group,
a 2-(2-naphthyl)ethyl group, a 3-(2-naphthyl)propyl group,
a 8-fluoro-2-naphthyl group,
a (8-fluoro-2-naphthyl)methyl group,
a 2-(8-fluoro-2-naphthyl)ethyl group,
a 3-(8-fluoro-2-naphthyl)propyl group,
a 8-chloro-2-naphthyl group,
a (8-chloro-2-naphthyl)methyl group,
a 2-(8-chloro-2-naphthyl)ethyl group,
a 3-(8-chloro-2-naphthyl)propyl group,
a 8-bromo-2-naphthyl group,
a (8-bromo-2-naphthyl)methyl group,
a 2-(8-bromo-2-naphthyl)ethyl group,
a 3-(8-bromo-2-naphthyl)propyl group.

Then, Formulation Examples will be shown. In addition, part indicates part by weight.

Formulation Example 1

20 parts of any one of the present amide compounds (1) to (28) is dissolved in 65 parts of xylene, and 15 parts of SORPOL 3005X (registered trade name of TOHO Chemical Industry Co., Ltd.) is added thereto. The mixture is well stirred and mixed to obtain an emulsifiable concentrate.

Formulation Example 2

40 parts of any one of the present amide compounds (1) to (28) and 5 parts of SORPOL 3005X are well mixed, and then 32 parts of Carplex #80 (synthetic hydrous silicon oxide, registered trade name of Shionogi & Co., Ltd.), and 23 parts of 300-mesh diatomaceous earth are added thereto. The mixture is stirred and mixed with a juice mixer to obtain a wettable powder.

Formulation Example 3

1.5 parts of any one of the present amide compounds (1) to (28), 1 part of Tokuseal GUN (synthetic hydrous silicon oxide, manufactured by Tokuyama corporation), 2 parts of Reax 85A (sodium ligninsulfonate, manufactured by West vaco chemicals), 30 parts of Bentonite Fuji (bentonite, manufactured by HOJUN Co., Ltd.), and 65.5 parts of Shokozan A clay (kaolin clay, manufactured by SHOKOZAN MINING Co., Ltd.) are well pulverized and mixed, and water is added thereto. The mixture is then kneaded well, granulated with an extrusion granulator, and dried to obtain 1.5% granules.

Formulation Example 4

10 parts of any one of the present amide compounds (1) to (28), 10 parts of phenylxylylethane, and 0.5 part of Sumijule L-75 (tolylene diisocyanate, manufactured by Sumitomo Bayer Urethane Co., Ltd.) are mixed, and then the mixture is added to 20 parts of a 10% aqueous solution of arabic gum, followed by stirring the resulting mixture with a homomixer to obtain an emulsion having an average particle diameter of 20 Thereto is added 2 parts of ethylene glycol, and the mixture is further stirred in a warm bath at 60° C. for 24 hours to obtain a microcapsule slurry. Separately, 0.2 parts of xanthan gum and 1.0 part of Veegum R (aluminum magnesium silicate, registered trade name of Vanderbilt Company) are dispersed in 56.3 parts of ion-exchanged water to obtain a thickening agent solution. 42.5 parts of the microcapsule slurry and 57.5 parts of the thickening agent solution are mixed to obtain a microcapsule formulation.

Formulation Example 5

10 parts of any one of the present amide compounds (1) to (28) and 10 parts of phenylxylylethane are mixed, and then the mixture is added to 20 parts of 10% aqueous solution of polyethylene glycol, followed by stirring the resulting mixture with a homomixer to obtain an emulsion having an average particle diameter of 3 μm. Separately, 0.2 parts of xanthan gum and 1.0 part of Veegum R (aluminum magnesium silicate, registered trade name of Vanderbilt Company) are dispersed in 58.8 parts of ion-exchanged water to obtain a thickening agent solution. 40 parts of the emulsion solution and 60 parts of the thickening agent solution are mixed to obtain a flowable.

Formulation Example 6

5 parts of any one of the present amide compounds (1) to (28), 3 parts of Carplex #80 (a fine powder of synthetic hydrous silicon oxide, registered trade name of Shionogi & Co., Ltd.), 0.3 parts of PAP (a mixture of monoisopropyl phosphate and diisopropyl phosphate) and 91.7 parts of talc (300 mesh) are stirred and mixed with a juice mixer to obtain a dust formulation.

Formulation Example 7

0.1 parts of any one of the present amide compounds (1) to (28) is dissolved in 10 parts of isopropyl alcohol, and the mixture is mixed with 89.9 parts of deodorized kerosene to obtain an oil solution.

Formulation Example 8

1 part of any one of the present amide compounds (1) to (28), 5 parts of dichloromethane and 34 parts of deodorized kerosene are mixed and dissolved. The resulting solution is filled into an aerosol container, and a valve part is attached to the container, then 60 parts of a propellant (liquefied petroleum gas) is filled under pressure into the container through the valve part to obtain an oil-based aerosol.

Formulation Example 9

0.6 parts of any one of the present amide compounds (1) to (28), 5 parts of xylene, 3.4 parts of deodorized kerosene and 1 part of ATMOS 300 (emulsifier, registered trade name of Atlas Chemical Company) are mixed and dissolved, and the resulting solution and 50 parts of water are filled into an aerosol container, and 40 parts of a propellant (liquefied petroleum gas) is filled under pressure into the container through the valve part to obtain an aqueous aerosol.

Formulation Example 10

0.3 g of any one of the present amide compounds (1) to (28) is dissolved in 20 ml of acetone. The resulting solution is uniformly stirred and mixed with 99.7 g of a base material for an insecticidal coil (a mixture of Tabu powder, Pyrethrum marc and wood powder in a ratio of 4:3:3). Thereafter, 100 ml of water is added to the mixture, and the resulting mixture is sufficiently kneaded, and molded and dried to obtain an insecticidal coil.

Formulation Example 11

0.8 g of any one of the present amide compounds (1) to (28) and 0.4 g of piperonyl butoxide are dissolved in acetone to have a total amount of 10 ml. A base material for an insecticidal mat for electric heating with a size of 2.5 cm×1.5 cm, 0.3 cm in thickness (a plate of compacted fibrils of a mixture of cotton linter and pulp) is uniformly impregnated with 0.5 ml of this solution to obtain an insecticidal mat for electric heating.

Formulation Example 12

3 parts of any one of the present amide compounds (1) to (28) is dissolved in 97 parts of deodorized kerosene to obtain a solution, and this solution is put in a container made of polyvinyl chloride. Into the container is inserted an absorptive wick (which is prepared by solidifying powders of an inorganic powder with a binder followed by sintering them) whose upper portion can be heated by a heater, to obtain a part to be used for an absorptive wick type electric heating vaporizer.

Formulation Example 13

100 mg of any one of the present amide compounds (1) to (28) is dissolved in an appropriate amount of acetone, and a porous ceramic plate with a size of 4.0 cm×4.0 cm, 1.2 cm in thickness is impregnated with the solution to obtain a fumigant for heating.

Formulation Example 14

100 µg of any one of the present amide compounds (1) to (28) is dissolved in an appropriate amount of acetone, and the solution is uniformly applied on a filter paper of 2 cm×2 cm, 0.3 mm in thickness. Then, the filter paper is air-dried to remove acetone to obtain a formulation vaporizable at room temperature.

Formulation Example 15

10 parts of any one of the present amide compounds (1) to (28), 35 parts of white carbon containing 50 parts of polyoxyethylene alkyl ether sulfate ammonium salt and 55 parts of water are mixed, and the mixture is finely pulverized by wet grinding method to obtain a formulation.

Next, the noxious arthropod controlling effect of the present amide compound is shown as test examples.

Test Example 1

A formulation containing each of the present amide compounds (1), (2), (4), (8), (12), (13), (14), (15), (16), (18), (20), (24), (25), (27) and (28) prepared in accordance with Formulation Example 7 was diluted with an isopropyl alcohol/deodorized kerosine=1/9 mixed liquid so that the active ingredient concentration became 2.0% w/v, to prepare a drug solution for a test.

Ten vermin of *Blattella germanica* (male female each five vermin) were allowed to release in a container for a test in which a butter was applied on an inner wall (diameter 8.75 cm, height 7.5 cm, bottom face covered with 16 mesh wire net), and the container was arranged on a bottom of a chamber for a test (bottom surface: 46 cm×46 cm, height: 70 cm). From a height of 60 cm from an upper side of the container, 1.5 ml of the drug solution for a test was sprayed using a spray gun (spraying pressure 0.42 kg/cm$^2$). Thirty seconds after spraying, the container was taken out from the chamber for a test, the number of vermin which had been knocked down was counted for 15 minutes with time, and a knockdown ratio was obtained. The knockdown ratio was calculated by the following expression.

Knockdown ratio (%)=(number of knocked down vermin/number of test vermin)×100

As a result, the knockdown ratio of test vermin within 15 minutes was 80% or more, in treatment with present amide compounds (1), (2), (4), (8), (12), (13), (14), (15), (16), (18), (20), (24), (25), (27) and (28).

Test Example 2

A formulation containing each of the present amide compounds (1), (2), (4), (13), (15), (16) and (25) prepared in accordance with Formulation Example 7 was diluted with an isopropyl alcohol/deodorized kerosine=1/9 mixed liquid so that the active ingredient concentration became 2.0% w/v, to prepare a drug solution for a test.

Ten imagoes of *Musca domestica* (male female each five vermin) were allowed to release in a polyethylene cup (bottom surface diameter 10.6 cm), and the cup was covered with a 16 mesh nylon gauze. The polyethylene cup was arranged on a bottom of a chamber for a test (bottom surface: 46 cm×46 cm, height: 70 cm). From a height of 30 cm from an upper surface of the polyethylene cup, 0.5 ml of a drug solution for a test was sprayed using a spray gun (spraying pressure 0.9 kg/cm$^2$). After spraying, the cup was immediately taken out from the chamber for a test, and the number of knocked down vermin was counted for 15 minutes with time, and a knockdown ratio was obtained. The knockdown ratio was calculated by the following expression.

Knockdown ratio (%)=(number of knocked down vermin/number of test vermin)×100

As a result, in treatment with the present amide compounds (1), (2), (4), (13), (15), (16) and (25), the knockdown ratio of the test vermin within 15 minutes was 80% or more.

Test Example 3

A formulation containing each of the present amide compounds (1), (2), (4), (5), (6), (7), (8), (9), (10), (12), (13), (14), (15), (16), (18), (19), (21), (22), (24), (25), (26) and (27) prepared in accordance with Formulation Example 7 was diluted with an isopropyl alcohol/deodorized kerosine=1/9 mixed liquid so that the active ingredient concentration became 0.1% w/v, to prepare a drug solution for a test.

Ten imagoes of Culexpipienspallens were allowed to release in a polyethylene cup (bottom surface diameter 10.6 cm), and the cup was covered with a 16 mesh nylon gauze. The polyethylene cup was arranged on a bottom of a chamber for a test (bottom surface: 46 cm×46 cm, height: 70 cm). From a height of 30 cm from an upper surface of the polyethylene cup, 0.5 ml of the drug solution for a test was sprayed using a spray gun (spraying pressure 0.4 kg/cm$^2$). After spraying, the cup was immediately taken out from the chamber for a test, the number of knocked down vermin was counted for 15 minutes with time, and a knockdown ratio was obtained. The knockdown ratio was calculated by the following expression.

Knockdown ratio (%)=(number of knocked down vermin/number of test vermin)×100

As a result, in treatment with the present amide compounds (1), (2), (4), (5), (6), (7), (8), (9), (10), (12), (13), (14), (15), (16), (18), (19), (21), (22), (24), (25), (26) and (27), the knockdown ratio of the test vermin within 15 minutes was 80% or more.

Test Example 4

A formulation containing each of the present amide compounds (10), (15), (18) and (19) prepared in accordance with Formulation Example 15 was diluted with water so that the active ingredient concentration became 500 ppm, to prepare a drug solution for a test.

To 100 ml of ion-exchanged water was added 0.7 ml of the drug solution for a test (active ingredient concentration 3.5 ppm). Twenty last instar larvae of Culexpipienspallens were released in the solution, the life or death thereof was investigated after 8 days, and a dead vermin ratio was obtained. The dead vermin ratio was calculated by the following expression.

Dead vermin ratio (%)=(number of dead vermin/number of test vermin)×100

As a result, in treatment with the present amide compounds (10), (15), (18) and (19), the dead vermin ratio was 90% or more.

Test Example 5

A formulation containing each of the present amide compounds (4), (15), (22), (25) and (27) prepared in accordance with Formulation Example 15 was diluted with water so that the active ingredient concentration became 500 ppm, to prepare a drug solution for a test.

On a bottom of a polyethylene cup of a diameter of 5.5 cm, a filter paper having the same size was spread, 0.7 ml of the drug solution for a test was dropped on the filter paper, and 30 mg of a sugar as a bait was placed therein uniformly. Ten female imagoes of Muscadomestica were released in the polyethylene cup, and the cup was closed with a lid. After 24 hours, the life or death of Muscadomestica was investigated, and a dead vermin ratio was obtained. The dead vermin ratio was calculated by the following expression.

Dead vermin ratio (%)=(number of dead vermin/number of test vermin)×100

As a result, in treatment with the present amide compounds (4), (15), (22), (25) and (27), the dead vermin ratio was 100% or more.

Test Example 6

A formulation of each of the present amide compounds (2), (9), (10) and (15) prepared in accordance with Formulation Example 15 was diluted with water so that the active ingredient concentration became 500 ppm, to prepare a spray solution for a test.

On the other hand, a cabbage was planted in a polyethylene cup, and grown until a third true leaf or a fourth true leaf developed. To the cabbage, the spray solution for a test was sprayed at a rate of 20 ml/cup.

After the drug solution which had been spraying-treated on the cabbage was dried, 10 third instar larvae of Plutellaxylostella were parasitized, the number of Plutellaxylostella was investigated after 5 days, and a controlling value was obtained based on the following criteria.

Controlling value (%)={1−($Cb$×$Tai$)/($Cai$×$Tb$)}×100

In addition, letters in the expression indicate the following meanings.
Cb: Number of vermin before treatment of non-treated section
Cai: Number of vermin at observation of non-treated section
Tb: Number of vermin before treatment of treated-section
Tai: Number of vermin at observation of treated-section As a result, in treatment with the present amide compounds (2), (9), (10) and (15), the controlling value was 100% or more.

Test Example 7

A formulation containing the present amide compound (25) prepared in accordance with Formulation Example 15 was diluted with water so that active ingredient concentration became 500 ppm, to preparer a spray solution for a test.

81

On the other hand, a cabbage was planted in a polyethylene cup, and grown until a third true leaf or a fourth true leaf developed. On the cabbage, the spray solution for a test was sprayed at a rate of 20 ml/cup. After the drug solution which had been spraying-treated on the cabbage was dried, ten fourth instar larvae of Spodopteralitura were parasitized. The number of live vermin of Spodopteralitura on a cabbage leaf was investigated after 4 days, and a controlling value was obtained according to the following expression.

Controlling value (%)={1−(Cb×Tai)/(Cai×Tb)}×100

In addition, letters in the equation represent the following meanings.
Cb: Number of vermin before treatment of non-treated section
Cai: Number of vermin at observation of non-treated section
Tb: Number of vermin before treatment of treated-section
Tai: Number of vermin at observation of treated-section
As a result, the treated-section of the present amide compound (25) showed a controlling value of 80% or more.

Test Example 8

A formulation of the present amide compound (9) prepared in accordance with Formulation Example 15 was diluted with water so that the active ingredient concentration became 500 ppm, to prepare a spray solution for a test.

On the other hand, 20 ml of the spray solution for a test was spraying-treated on each of apple seedlings (28 days after seeding, tree height about 15 cm) planted in a plastic cup. After the drug solution which had spray-treated on the apple was air-dried to an extent that the drug solution was dried, about 30 first instar larvae of Adoxophyesoranafasciata were released. Seven days after spraying, the number of live vermin on an apple seedling was investigated, and a controlling value was obtained according to the following expression.

Controlling value (%)={1−(Cb×Tai)/(Cai×Tb)}×100

In addition, letters in the expression indicate the following meanings.
Cb: Number of vermin before treatment of non-treated section
Cai: Number of vermin at observation of non-treated section
Tb: Number of vermin before treatment of treated-section
Tai: Number of vermin at observation of treated-section
As a result, in treatment with the present amide compound (9), the controlling value of 100% was shown.

INDUSTRIAL APPLICABILITY

The present amide compound has controlling efficacy on a noxious arthropod, and is useful as an active ingredient of a noxious arthropod controlling agent.

The invention claimed is:

1. A method for controlling a noxious arthropod comprising applying an effective amount of an amide compound of formula (I) to a noxious arthropod or a habitat of a noxious arthropod:

(I)

wherein
X represents a nitrogen atom or a CH group,
p represents 0 or 1,
A represents a phenyl group optionally having one or more atoms or groups selected from Group F,
a C3-C6 cycloalkyl group optionally having one or more atoms or groups selected from Group F,
a pyridyl group optionally having one or more atoms or groups selected from Group F,
a 3 to 7-membered saturated heterocyclic group optionally having one or more atoms or groups selected from Group F, wherein a hetero atom or atoms constituting the heterocycle is one or more atoms selected from the group consisting of an oxygen atom and a sulfur atom, and the hetero atoms are not adjacent to each other, or
a C1-C5 alkyl group optionally having one or more groups selected from the group consisting of a hydroxyl group and a C1-C3 alkoxy group, provided that when A is a C1-C5 alkyl group optionally having one or more groups selected from the group consisting of a hydroxyl group and a C1-C3 alkoxy group, p is 1,
$R^1$ and $R^2$ are the same or different, and independently represent a C1-C3 alkyl group or a hydrogen group,
$R^3$ and $R^4$ are the same or different, and independently represent a C1-C3 alkyl group optionally having one or more halogen atoms, or
a hydrogen atom,
n represents 1 or 2,
$R^5$ and $R^6$ are the same or different, and independently represent
a C1-C4 alkyl group optionally having one or more halogen atoms, a halogen atom or a hydrogen atom,
Y represents a single bond, or an oxygen atom, wherein when Y represents a single bond, m represents 0, and
Q represents a C1-C8 chain hydrocarbon group having one or more atoms or groups selected from Group C, or a C3-C8 chain hydrocarbon group, and wherein
when Y represents an oxygen atom, m represents any integer of 0 to 7, and Q represents a C1-8 chain hydrocarbon group optionally having one or more atoms or groups selected from Group D, or one group selected from Group E,
Group C consisting of a C3-C8 cycloalkyl group optionally having one or more atoms or groups selected from Group B,
an indanyl group optionally having one or more atoms or groups selected from Group B,
a 1,2,3,4-tetrahydronaphthyl group optionally having one or more atoms or groups selected from Group B,
a phenyl group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B,
a benzothienyl group optionally having one or more atoms or groups selected from Group B,
a 1,3-benzodioxolyl group optionally having one or more atoms or groups selected from Group B, a 1,4-benzodioxanyl group optionally having one or more atoms or groups selected from Group B, a halogen atom, a C1-C4 alkoxycarbonyl group optionally having one or more halogen atoms, a cyano group, a nitro group, a carboxyl group, a hydroxyl group, and a —CONR$^9$R$^{10}$ group;

Group D consisting of a C3-C8 cycloalkyl group optionally having one or more atoms or groups selected from Group B, an indanyl group optionally having one or more atoms or groups selected from Group B, a 1,2,3,4-tetrahydronaphthyl group optionally having one or more atoms or groups selected from Group B, a phenyl group optionally having one or more atoms or groups selected from Group B, a naphthyl group optionally having one or more atoms or groups selected from Group B, a pyridyl group optionally having one or more atoms or groups selected from Group B, a quinolyl group optionally having one or more atoms or groups selected from Group B, a furyl group optionally having one or more atoms or groups selected from Group B, a thienyl group optionally having one or more atoms or groups selected from Group B, a benzofuranyl group optionally having one or more atoms or groups selected from Group B, a benzothienyl group optionally having one or more atoms or groups selected from Group B, a 1,3-benzodioxolyl group optionally having one or more atoms or groups selected from Group B, a 1,4-benzodioxanyl group optionally having one or more atoms or groups selected from Group B, a phenoxy group optionally having one or more atoms or groups selected from Group B, a halogen atom, a C1-C4 alkoxycarbonyl group optionally having one or more halogen atoms, a cyano group, a nitro group, a carboxyl group, a hydroxyl group, and a —CONR$^9$R$^{10}$ group, Group E consisting of a C3-C8 cycloalkyl group optionally having one or more atoms or groups selected from Group B, an indanyl group optionally having one or more atoms or groups selected from Group B, a 1,2,3,4-tetrahydronaphthyl group optionally having one or more atoms or groups selected from Group B, a phenyl group optionally having one or more atoms or groups selected from Group B, a naphthyl group optionally having one or more atoms or groups selected from Group B, a pyridyl group optionally having one or more atoms or groups selected from Group B, a quinolyl group optionally having one or more atoms or groups selected from Group B, a furyl group optionally having one or more atoms or groups selected from Group B, a thienyl group optionally having one or more atoms or groups selected from Group B, a benzofuranyl group optionally having one or more atoms or groups selected from Group B, and a benzothienyl group optionally having one or more atoms or groups selected from Group B, Group B consisting of a C1-C4 alkyl group optionally having one or more halogen atoms, a C1-C4 alkyl group having one or more benzyloxy groups, a C1-C4 alkoxy group optionally having one or more halogen atoms, a C1-C4 alkylthio group optionally having one or more halogen atoms, a C1-C4 alkylsulfinyl group optionally having one or more halogen atoms, a C1-C4 alkylsulfonyl group optionally having one or more halogen atoms, a C1-C4 alkoxycarbonyl group optionally having one or more halogen atoms, a vinyl group optionally having one or more atoms or groups selected from Group F, an ethynyl group optionally having an atom or a group selected from Group F, a phenyl group, a phenoxy group, a cyano group, a nitro group, a carboxyl group, a hydroxyl group, a —CONR$^9$R$^{10}$ group, a methoxymethyl group, and a halogen atom, R$^9$ and R$^{10}$ are the same or different, and independently represent a C1-C4 alkyl group optionally having one or more halogen atoms, or a hydrogen atom, and Group F consisting of a C1-C4 alkyl group optionally having one or more halogen atoms, a C1-C4 alkoxy group optionally having one or more halogen atoms, and a halogen atom.

2. The method for controlling a noxious arthropod according to claim 1, wherein in the formula (I), p is 1, A is a phenyl group optionally having one or more atoms or groups selected from Group F, a pyridyl group optionally having one or more atoms or groups selected from Group F, a tetrahydrofuranyl group optionally having one or more atoms or groups selected from Group F, a tetrahydropyranyl group optionally having one or more atoms or groups selected from Group F, or a C1-C5 alkyl group optionally having one or more groups selected from the group consisting of a hydroxyl group and a C1-C3 alkoxy group, R$^1$ is a hydrogen atom, R$^2$ is a methyl group or a hydrogen atom, R$^3$ and R$^4$ are a hydrogen atom, R$^5$ and R$^6$ are a hydrogen atom, wherein when Y is a single bond, m is 0, and Q is a C1-C8 alkyl group having one or more groups selected from Group G, or a C3-C8 alkyl group, and wherein when Y is an oxygen atom, m is any integer of 1 to 7, and Q is a C1-C8 alkyl group having one or more groups selected from Group G, or one group selected from Group G, Group G consisting of a phenyl group optionally having one or more atoms or groups selected from Group H, and a naphthyl group optionally having one or more atoms or groups selected from Group H, Group H consisting of a C1-C4 alkyl group, a C1-C4 alkoxy group, and a halogen atom.

3. The method for controlling a noxious arthropod according to claim 2, wherein in the formula (I), X is a nitrogen atom, and n is 1.

4. The method for controlling a noxious arthropod according to claim 2, wherein in the formula (I), X is a nitrogen atom, and n is 2.

5. The method for controlling a noxious arthropod according to claim 2, wherein in the formula (I), X is a CH group, and n is 2.

6. The method for controlling a noxious arthropod according to claim 1, wherein in the formula (I), $R^1$ is a hydrogen atom,
$R^2$ is a methyl group or a hydrogen atom,
$R^3$ and $R^4$ are a hydrogen atom,
the group represented by Q-Y—$(CR^5R^6)_m$ is a $Q^a$-$CH_2$—O—$CH_2$ group, a $Q^a$-$CH_2$—$CH_2$—$CH_2$ group, a $Q^a$-O—$CH_2$ group or a $Q^a$-$CH_2$ group,
$Q^a$ is a phenyl group optionally having one or more atoms or groups selected from Group H or a naphthyl group optionally having one or more atoms or groups selected from Group H,
Group H consisting of a C1-C4 alkyl group, a C1-C4 alkoxy group, and a halogen atom.

* * * * *